United States Patent
Singh et al.

(10) Patent No.: US 10,925,858 B2
(45) Date of Patent: Feb. 23, 2021

(54) S-NITROSOGLUTATHIONE (GSNO) AND GSNO REDUCTASE INHIBITORS FOR USE IN THERAPY

(71) Applicants: MUSC FOUNDATION FOR RESEARCH DEVELOPMENT, Charleston, SC (US); THE US GOVERNMENT AS REPRESENTED BY THE DEPARTMENT OF VETERANS AFFAIRS, Washington, DC (US)

(72) Inventors: Inderjit Singh, Mt. Pleasant, SC (US); Avtar K. Singh, Mt. Pleasant, SC (US)

(73) Assignees: The US Government as Represented by the Department of Veterans Affairs, Washington, DC (US); MUSC Foundation for Research Development, Charleston, SC (US)

(*) Notice: Subject to any disclaimer, the term of this patent is extended or adjusted under 35 U.S.C. 154(b) by 0 days.

(21) Appl. No.: 16/336,984

(22) PCT Filed: May 8, 2018

(86) PCT No.: PCT/US2018/031622
§ 371 (c)(1),
(2) Date: Mar. 27, 2019

(87) PCT Pub. No.: WO2018/208793
PCT Pub. Date: Nov. 15, 2018

(65) Prior Publication Data
US 2020/0054610 A1 Feb. 20, 2020

Related U.S. Application Data

(60) Provisional application No. 62/503,108, filed on May 8, 2017.

(51) Int. Cl.
| A61K 31/4178 | (2006.01) |
| A61K 38/06 | (2006.01) |
| A61K 45/06 | (2006.01) |

(52) U.S. Cl.
CPC ........ *A61K 31/4178* (2013.01); *A61K 38/063* (2013.01); *A61K 45/06* (2013.01)

(58) Field of Classification Search
CPC ............. A61K 2300/00; A61K 31/198; A61K 31/4178; A61K 38/02; A61K 38/06;
(Continued)

(56) References Cited

U.S. PATENT DOCUMENTS

| 9,180,119 B2 | 11/2015 | Wasley et al. |
| 9,198,909 B1 | 12/2015 | Sanghani |

(Continued)

FOREIGN PATENT DOCUMENTS

| WO | WO 2005/063275 | 7/2005 |
| WO | WO 2009/076665 | 6/2009 |

(Continued)

OTHER PUBLICATIONS

Green et al., "Mechanism of inhibition for N6022, a first-in-class drug targeting S-nitrosoglutathione reductase," *Biochemistry*, 51910):2157-68, 2012.
(Continued)

*Primary Examiner* — Savitha M Rao
(74) *Attorney, Agent, or Firm* — Parker Highlander PLLC

(57) ABSTRACT

The present disclosure provides methods for the treatment of neurological deficits by the administration of GSNO or GSNO reductase inhibitor. Further provided herein are methods of treating autoimmune diseases by administering GSNO or GSNO reductase inhibitor.

22 Claims, 23 Drawing Sheets
Specification includes a Sequence Listing.

(58) Field of Classification Search
CPC .... A61K 38/215; A61K 38/28; A61K 38/063; A61K 45/06
See application file for complete search history.

(56) References Cited

U.S. PATENT DOCUMENTS

| | | |
|---|---|---|
| 2008/0227846 A1 | 9/2008 | Singh et al. |
| 2011/0245188 A1 | 10/2011 | Singh |

FOREIGN PATENT DOCUMENTS

| | | |
|---|---|---|
| WO | WO 2012/170371 | 12/2012 |
| WO | WO 2014/058974 | 4/2014 |

OTHER PUBLICATIONS

Khan et al., "Administration of S-nitrosoglutathione after traumatic brain injury protects the neurovascular unit and reduces secondary injury in a rat model of controlled cortical impact," *Journal of Neuroinflammation*, 6(32):1-12, 2009.

Khan et al., "The inhibitory effect of S-nitrosoglutathione on blood-brain barrier disruption and peroxynitrite formation in a rat model of experimental stroke," *Journal of Neurochemistry*, 123(Suppl. 2):86-97, 2012.

Nath et al., "S-nitrosoglutathione a physiologic nitric oxide carrier attenuates experimental autoimmune encephalomyelitis," *Journal of Neuroimmune Pharmacology*, 5(2):240-251, 2010.

Niedbala et al., "Nitric oxide-induced regulatory T cells inhibit Th17 but not Th1 cell differentiation and function," *Journal of Immunology*, 191(1):164-170, 2013.

PCT International Search Report and Written Opinion issued in International Application No. PCT/US2018/031622, dated Sep. 11, 2018.

Shunmugavel et al., "S-Nitrosoglutathione administration ameliorates cauda equina compression injury in rats," *Neuroscience & Medicine*, 3(3):294-305, 2012.

Singh, "Immunomodulation and Neuroprotection in Multiple Sclerosis," National Institutes of Health Grant Project No. 1I01BX002829-01A1, 2015.

Sun et al., "Discovery of s-nitrosoglutathione reductase inhibitors: potential agents for the treatment of asthma and other inflammatory diseases," *ACS Medicinal Chemistry Letters*, 2(5):402-406, 2011.

Won et al., "S-nitrosoglutathione reduces tau hyper-phosphorylation and provides neuroprotection in rat model of chronic cerebral hypoperfusion," *Brain Research*, 1624:359-369, 2015.

S-NITROSOGLUTATHIONE (GSNO) AND GSNO REDUCTASE INHIBITORS FOR USE IN THERAPY

This application is a national phase application under 35 U.S.C. § 371 of International Application No. PCT/US2018/031622, filed May 8, 2018, which claims the benefit of U.S. Provisional Patent Application No. 62/503,108, filed May 8, 2017, the entirety of each of which is incorporated herein by reference.

The invention was made with government support under Grant No. Grant No. NS72511 awarded by the National Institutes of Health and Grant Nos. BX002829, RX001257 and RX2090 awarded by the U.S. Department of Veterans Affairs. The government has certain rights in the invention.

Pursuant to 37 C.F.R. 1.821(c), a sequence listing is submitted herewith as an ASCII compliant text file named "MESCP0106US_ST25.txt", created on Feb. 19, 2019 and having a size of ~3 kilobytes. The content of the aforementioned file is hereby incorporated by reference in its entirety.

BACKGROUND OF THE INVENTION

1. Field of the Invention

The present invention relates generally to the field of medicine. More particularly, it concerns methods of treating diseases by administering S-nitrosoglutathione (GSNO) and/or a GSNO reductase inhibitor.

2. Description of Related Art

The blood brain barrier (BBB) segregates the central nervous system (CNS) from systemic circulation and protects it from toxic agents in blood (Abbott et al., 2010). It consists of specialized endothelial cells that are characterized by the presence of tight junctions composed of membrane proteins: occludin, claudins and junctional adhesion molecules involved in intercellular contacts forming interactions with cytoplasmic scaffolding proteins zonula occludens (ZO) proteins (Citi et al., 2012). BBB disruption compromises synaptic and neuronal functions playing important roles in CNS disorders (Zlokovic 2008). Reduced BBB function contributes to cognitive dysfunctions associated with diabetes (Mogi & Horiuchi 2011). Diabetes induces microvascular complications in the brain by altering blood flow, BBB permeability and abnormal endothelial proliferation, thereby affecting cognitive functions in diabetic individuals (Dandona et al., 1978, Hammes et al., 2002, Hawkins et al., 2007). Increased BBB permeability and white matter hyperintensities have been detected in diabetic subjects by gadolinium magnetic resonance imaging, suggesting alterations in BBB integrity (Starr et al., 2003). Hyperglycemia associated with diabetes alters the brain microvasculature resulting in increased BBB permeability and brain edema leading to neurological deficits (Aggarwal et al., 2015).

Studies found that hyperglycemia leads to increased BBB permeability via modulating MMP9/TIMP-1 expression (Aggarwal et al., 2015). However, diabetes induced BBB dysfunction involved interplay of many other molecules. Many studies have also suggested that hyperglycemia increases BBB permeability via loss of tight junction proteins (ZO-1, occludin, Claudin-5) (Hawkins et al., 2007). Occludin (60 kDa) is a tetraspan integral membrane protein, functionally important for barrier function and its domain contain cysteine residues which have been found to be redox-sensitive (Furuse et al., 1993). Claudins constitute a large family of 20-27 kDa membrane proteins with brain endothelial cells predominantly expressing claudin-3 and claudin-5 (Ohtsuki et al., 2007). Exogenous expression of claudin-5 strengthens barrier properties and its depletion induces BBB disruption (Nitta et al. 2003) as they support tight junction integrity via cis- and trans-homodimerization and heterodimerization (Morita et al., 2003). On the other hand, ZO proteins (ZO-1, ZO-2 and ZO-3) associate with tight junction transmembrane proteins and contribute to tight junction integrity in brain endothelial cells (Bauer et al., 2010). They are essential for the assembly of claudins and occludin at tight junctions, thereby anchoring them to the actin cytoskeleton (Fanning & Anderson, 2009). Loss of occludin, ZO-1 and claudin-5 expression from the tight junction assembly has been associated with increased BBB permeability in many neurodegenerative diseases (Zlokovic, 2008). Occludin and ZO-1 has also been found to be decreased in both cerebral and retinal microvasculature in animal model of diabetes (Harhaj & Antonetti, 2004). Decreased occludin content in diabetic retinopathy may result from degradation by matrix metalloproteinases (MMPs) (Giebel et al., 2005). It is therefore possible that diabetes leads to compromise of BBB tight junction assembly via stimulation of MMP activity which has been found to be considerably activated in the diabetic brain as suggested in previous studies (Aggarwal et al., 2015).

Other molecules that play important roles in BBB maintenance and functioning are cell adhesion molecules. Interstitial cell adhesion molecule-1 (ICAM-1) and vascular cell adhesion molecule-1 (VCAM-1), present on the endothelial surface of the BBB plays an important role in leucocyte trafficking through vascular endothelium into CNS (Elices et al., 1990). In a diseased condition, upregulation of ICAM-1 and VCAM-1 allows intense leukocyte infiltration across the BBB thereby aggravating BBB dysfunction (Greenwood et al., 2002). Upregulation of ICAM-1 has been observed during hyperglycemia followed by ischemia reperfusion with significant impact on BBB integrity (Ennis & Keep, 2007). Subsequent studies also showed a marked increase of ICAM-1 in diabetic rats after reperfusion paralleled by increase in IL-Ip expression (Ding et al., 2005). Also, increased VCAM-1 expression has been noted in many diabetic tissues like heart, retina, and kidneys (Altannavch et al., 2004, Joussen et al., 2002). Thus, studying the role of these cell adhesion molecules in brain microvasculature of diabetic animals may provide useful insights in understanding the mechanism of BBB disruption.

Hyperglycemia has also been found to be accompanied by reduced nitric oxide bioavailability and increased nitrosative stress that appear to be involved in impaired vascular remodeling affecting BBB permeability (Phillips et al., 2005). S-nitrosoglutathione (GSNO), an S-nitrosated derivative of glutathione acts as a reservoir of nitric oxide and NO dependent signal transduction. It has been found to be protective against oxidative/nitrosative stress and inflammation in many diseases (Rauhala et al., 2005). GSNO has been reported to regulate BBB permeability, angiogenic, and neurorepair mechanisms in experimental models of stroke and traumatic brain injury (Khan et al., 2011, Khan et al., 2005). It has also been found to reduce endothelial cell activation and prevent loss of tight junctions, suggesting the potential of GSNO as a neuroprotective agent (Zampolli et al., 2000, Khan et al., 2009). Also, a previous study indicates that GSNO lowers the activation of MMPs preventing cognitive dysfunction in diabetic rodent model (Aggarwal et al., 2015). Therefore, there is an unmet need to evaluate the role of GSNO as a potential protective agent that prevents BBB disruption via modulating tight junction proteins and cell adhesion molecules thereby improving cognitive functions in experimental hyperglycemic conditions.

SUMMARY OF THE INVENTION

Embodiments of the present disclosure concern methods of treating diseases by administering an effective amount of GSNO and/or one or more GSNO reductase inhibitors to the subject. In one embodiment, the present disclosure provides a method of treating neurological deficits in a subject comprising administering an effective amount of S-nitrosoglutathione (GSNO) and/or a GSNO reductase inhibitor to the subject. In particular aspects, the GSNO reductase inhibitor is N6022. In particular aspects, the subject is human.

In some aspects, treating neurological deficits comprises restoring blood brain barrier (BBB) integrity, decreasing neurological inflammation, decreasing brain edema, improving ultrastructure of microvessels, and/or improving cognition. Thus, methods of the embodiments (e.g., administration of GSNO reductase inhibitors such as N6022), can, in some aspects, be used to treat BBB disruption, dementia (e.g., vascular dementia) or trauma that leads to BBB disruption. In certain aspects, restoring BBB integrity is further defined as increasing expression of a tight junction protein and/or decreasing expression of a cell adhesion molecule. In some aspects, the tight junction protein is ZO-1 and/or occludin. In certain aspects, cell adhesion molecule is ICAM-1 and/or VCAM-1. In some aspects, the increase or decrease in expression is at least 2-fold as compared to expression before administering the GSNO and/or GSNO reductase inhibitor. In particular aspects, the expression is measured in the cortex and/or hippocampus.

In some aspects, the subject has diabetes. In particular aspects, the subject has hyperglycemia associated with diabetes. In other aspects, the subject has an autoimmune disease, such as multiple sclerosis (MS) or rheumatoid arthritis.

In certain aspects, the GSNO and/or GSNO reductase inhibitor is administered orally, intravenously, intraperitoneally, intratracheally, intratumorally, intramuscularly, endoscopically, intralesionally, percutaneously, subcutaneously, regionally, or by direct injection or perfusion. In particular aspects, the GSNO and/or GSNO reductase inhibitor is administered orally.

In another embodiment, there is provided a method of treating an autoimmune disease in a subject comprising administering an effective amount of GSNO and/or at least one GSNO reductase inhibitor to the subject. In some aspects, the GSNO reductase inhibitor is N6022. In particular aspects, the subject is human.

In some aspects, the GSNO reductase inhibitor is administered orally, intravenously, intraperitoneally, intratracheally, intratumorally, intramuscularly, endoscopically, intralesionally, percutaneously, subcutaneously, regionally, or by direct injection or perfusion. In particular aspects, the GSNO reductase inhibitor is administered orally.

In certain aspects, the autoimmune disease is multiple sclerosis, rheumatoid arthritis, systemic lupus erythematosis, type 1 diabetes mellitus, or Crohn's disease. In particular aspects, the autoimmune disease is multiple sclerosis or rheumatoid arthritis.

In some aspects, the GSNO reductase inhibitor protects against myelin loss in spinal cord and/or selectively modulates CD4+ T cells subsets. In certain aspects, the GSNO reductase inhibitor reduces CNS infiltration of Th17 cells and/or increases CNS infiltration of regulatory T cells (Tregs), such as CD4+CD25+ FOXP3− T cells.

In aspects of the above embodiments, the method further comprises administering at least a second therapy. In some aspects, the second therapy is GSNO. In certain aspects, the second therapy is an anti-inflammatory, inhibitor of HMG-CoA reductase, immunosuppressive agent, or immunomodulatory agent. In particular aspects, the second therapy is interferon-β, glatiramer acetate, teriflunomide, dimethyl fumarate, natalizumab, fingolimod, alemtuzumab, simvastatin, and/or mitoxantrone. In some aspects, the second therapy is insulin or metformin.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figures 1A, 1B, 1C:
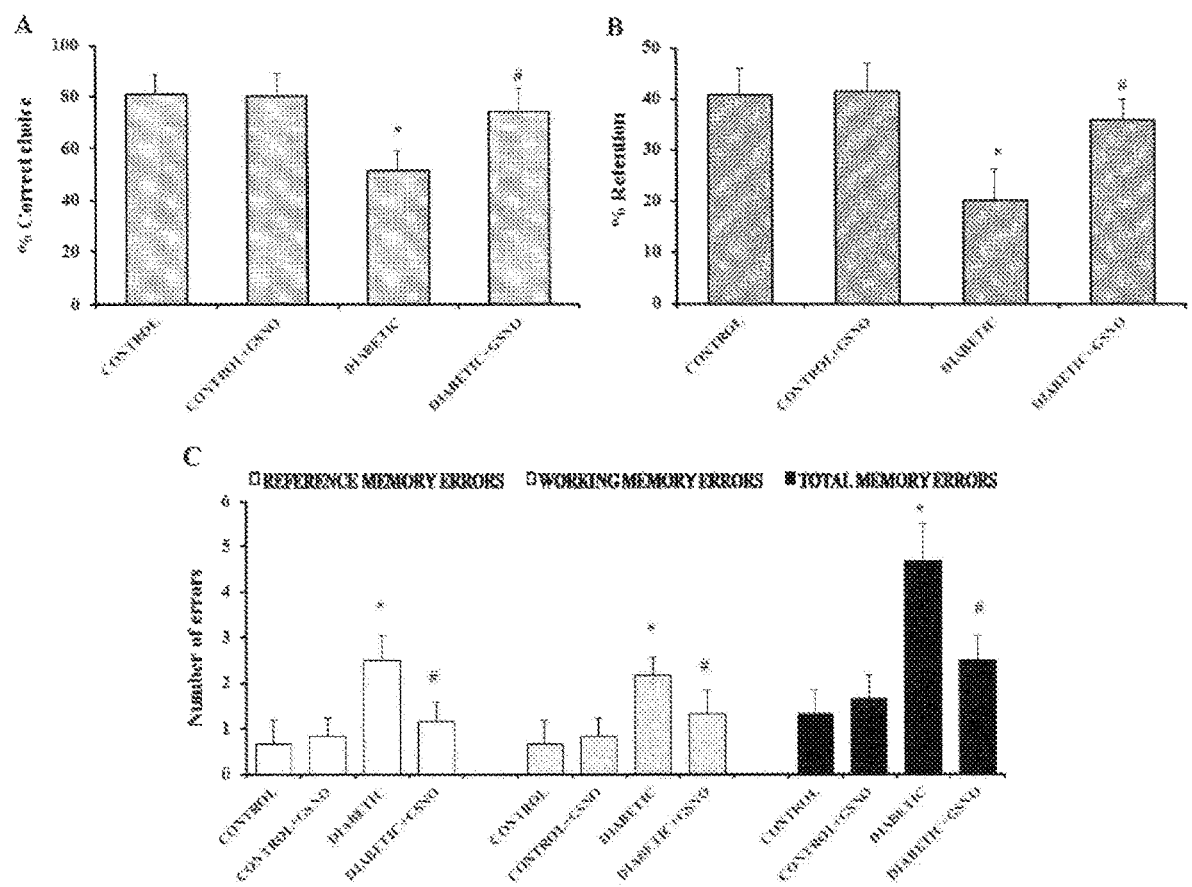
FIGS. 1A-1C: Effect of GSNO administration on (A) Percentage correct choice; (B) Percentage retention; (C) Reference, working and total memory errors in Radial arm maze after 8 weeks of induction of diabetes. * Significantly different from control group ($p<0.05$). # significantly different from diabetic group ($p<0.05$). Values are expressed as mean±SD; n=6/group.

Diabetes is associated with increased blood brain barrier (BBB) permeability causing neurological deficits. The present studies investigated the role of tight junction proteins [Zona occludens-1 (ZO-1), occludin, claudin-5] and cell adhesion molecules [intercellular cell adhesion molecule (ICAM)-1, vascular cell adhesion molecule (VCAM)-1] in aberrated BBB permeability and assessed the effect of S-nitrosoglutathione (GSNO) in a diabetic model. Diabetes was induced by intraperitoneal injection of streptozotocin (40 mg/kg body weight) for 5 days in mice. GSNO was administered orally (100 μg/kg body weight) daily for 8 weeks after the induction of diabetes. A significant decline in learning and memory was observed in diabetic mice gauged by the radial arm maze test. Relative mRNA and protein expression of ZO-1 and occludin were found to be significantly lowered in isolated microvessels obtained from diabetic cortex and hippocampus while claudin-5 remained unchanged.

Furthermore, immunofluorescence of tight junction proteins suggested that the fluorescent intensity for both ZO-1 and occludin appeared to be reduced in the diabetic brain. In addition, a significant upregulation was observed in mRNA and protein expression of ICAM-1 and VCAM-1 in diabetic animals. Also, ultrastructure of microvessels from diabetic brain was found to be aberrant suggesting BBB damage. However, GSNO administration to diabetic animals was able to ameliorate loss of ZO-1 and occludin as well as the upregulation of ICAM-1 and VCAM-1, restoring BBB integrity and improving cognition. These findings clearly suggest that GSNO may present a therapeutic potential by protecting BBB, thus preventing neurological complications in diabetes.

Accordingly, the present disclosure provides methods of treating neurological deficits by administering GSNO and/or a GSNO reductase inhibitor. Administration of GSNO and/or the reductase inhibitor may restore BBB integrity by decreasing BBB permeability. In addition, the therapy may decrease inflammation and/or edema in the brain as well as improve cognition. Subjects that may benefit from the therapy include patients with diabetes and multiple sclerosis (MS).

Further embodiments of the present disclosure concern methods of treating immune-related diseases, particularly autoimmune disorders with the administration of GSNO and/or one or more GSNO reductase inhibitors. The present studies showed that adoptive transfer of both TH1 and TH17 skewed T cells from GSNO treated EAE mice, as compared to T cells from untreated EAE mice, produced milder EAE disease, thus suggesting the role of IL-10 and IL-17 mediated mechanisms in GSNO mediated immunomodulation. Further, the mice adoptively immunized with T cells from GSNO treated EAE mice or untreated EAE mice were treated with GSNO during the course of the disease to investigate the role of GSNO in regulation of effector function of T cells. GSNO treatment decreased the passive EAE disease induced by adoptive transfer of both T cells from GSNO treated EAE mice and those from untreated EAE mice. These studies describe, for the first time, the GSNO mediated mechanisms in induction of IL-10 by TH1 and TH17 polarized cells and in turn attenuate the EAE disease.

Further studies involved N6022, a first-in-class compound that is a very potent, specific, and reversible inhibitor of GSNOR. GSNO and N6022 treatments selectively inhibited EAE-induced differentiation, expansion, and CNS infiltration of pro-inflammatory TH17 and induced that of anti-inflammatory CD4+CD25+ FOXP3- Treg, one of subtypes of regulatory T cells (Treg). Moreover, N6022 treatment, but not GSNO treatment, additionally inhibited pro-inflammatory TH1 and induced CD4+CD25+ FOXP3+ Treg, another subtype of Treg. In conclusion, the data in this study suggest that N6022 as a novel drug for MS/EAE that provides selective modulation of pro- and anti-inflammatory subsets of CD4+ cells (TH1/TH17 vs. TH21 Treg) without causing a lymphopenic effect. Overall, these data document a role of GSNO mediated mechanisms in lineage specific modulation of T cell polarization and effector function (e.g. IL-17 and IL-10). Thus, certain embodiments of the present disclosure provide the use of GSNO and/or GSNO reductase inhibitor as a potential prophylactic and therapeutic intervention for multiple sclerosis (MS) and other autoimmune diseases, such as rheumatoid arthritis, type 1 diabetes mellitus, dermatitis, eczema, and psoriasis.

I. Methods of Use

Embodiments of the present disclosure concern methods of treating diseases by administering an effective amount of GSNO and/or one or more GSNO reductase inhibitors to the subject.

S-Nitrosoglutathione (GSNO) is an endogenous S-nitrosothiol (SNO) that plays a critical role in nitric oxide (NO) signaling and is a source of bioavailable NO. The enzyme GSNO reductase (GSNOR) reduces S-nitrosoglutathione (GSNO) to an unstable intermediate, S-hydroxylaminoglutathione, which then rearranges to form glutathione sulfonamide, or in the presence of GSH, forms oxidized glutathione (GSSG) and hydroxylamine. Through this catabolic process, GSNOR regulates the cellular concentrations of GSNO and plays a central role in regulating the levels of endogenous S-nitrosothiols and controlling protein S-nitrosylation-based signaling. S-Nitrosoglutathione reductase (GSNOR) regulates S-nitrosothiols (SNOs) and nitric oxide (NO) in vivo through catabolism of S-nitrosoglutathione (GSNO). GSNOR and the anti-inflammatory and smooth muscle relaxant activities of SNOs, GSNO, and NO play significant roles in pulmonary, cardiovascular, and gastrointestinal function.

In some aspects, a subject is administered an inhibitor of GSNO reductase (GSNOR). For example, N6022 is a potent and reversible GSNO reductase inhibitor that may be used in the methods of the present disclosure (Sun et al., 2011; Green et al., 2012; both incorporated herein by reference). Further GSNO reductase inhibitors that may be used in the present disclosure include, but are not limited to, substituted pyrrole analogs (e.g., described in U.S. Pat. No. 8,642,628; incorporated herein by reference) and chromone inhibitors of GSNOR, such as 4-(2-(difluoromethyl)-7-hydroxy-4-oxo-4H-chromen-3-yl)benzoic acid, as disclosed in U.S. Pat. No. 8,669,381; incorporated herein by reference.

In some embodiments, the GSNO and/or one or more GSNO reductase inhibitors are used to treat neurological deficits, neurological inflammation, brain edema, damaged ultrastructure of microvessels, and/or cognition. The neurological deficits may be the result of increased permeability of the blood brain barrier, such as resulting from hyperglycemia associated with diabetes. In some aspects, the neurological inflammation may be associated with immune-related disorders, such as autoimmune disorders including multiple sclerosis and rheumatoid arthritis.

An "immune disorder," "immune-related disorder," or "immune-mediated disorder" refers to a disorder in which the immune response plays a key role in the development or progression of the disease. Immune-mediated disorders include autoimmune disorders, allograft rejection, graft versus host disease and inflammatory and allergic conditions.

An "autoimmune disease" or "autoimmune disorder" refers to a disease in which the immune system produces an immune response (for example, a B-cell or a T-cell response) against an antigen that is part of the normal host (that is, an autoantigen), with consequent injury to tissues. An autoantigen may be derived from a host cell, or may be derived from a commensal organism such as the micro-organisms (known as commensal organisms) that normally colonize mucosal surfaces.

The disorders can include pulmonary disorders associated with hypoxemia and/or smooth muscle constriction in the lungs and/or lung infection and/or lung injury (e.g., pulmonary hypertension, ARDS, asthma, pneumonia, pulmonary fibrosis/interstitial lung diseases, cystic fibrosis COPD) cardiovascular disease and heart disease, including conditions such as hypertension, ischemic coronary syndromes, atherosclerosis, heart failure, glaucoma, diseases characterized by angiogenesis (e.g., coronary artery disease), disorders where there is risk of thrombosis occurring, disorders where there is risk of restenosis occurring, chronic inflammatory diseases (e.g., AID dementia and psoriasis), diseases where there is risk of apoptosis occurring (e.g., heart failure, atherosclerosis, degenerative neurologic disorders, arthritis and liver injury (ischemic or alcoholic)), impotence, obesity caused by eating in response to craving for food, stroke, reperfusion injury (e.g., traumatic muscle injury in heart or lung, crush injury, spinal cord injury, or traumatic brain injury), and disorders where preconditioning of heart or brain for NO protection against subsequent ischemic events is beneficial.

Certain embodiments of the present disclosure provide methods for treating or preventing an immune-mediated disorder. In one embodiment, the subject has an autoimmune disease. Non-limiting examples of autoimmune diseases include: alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac spate-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, nephrotic syndrome (such as minimal change disease, focal glomerulosclerosis, or mebranous nephropathy), pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomenon, Reiter's syndrome, Rheumatoid arthritis, sarcoidosis, scleroderma, Sjogren's syndrome, stiff-man syndrome, systemic lupus erythematosus, lupus erythematosus, ulcerative colitis, uveitis, vasculitides (such as polyarteritis nodosa, takayasu arteritis, temporal arteritis/giant cell arteritis, or dermatitis herpetiformis vasculitis), vitiligo, and Wegener's granulomatosis. Thus, some examples of an autoimmune disease that can be treated using the methods disclosed herein include, but are not limited to, multiple sclerosis, rheumatoid arthritis, systemic lupus erythematosis, type 1 diabetes mellitus, Crohn's disease; ulcerative colitis, myasthenia gravis, glomerulonephritis, ankylosing spondylitis, vasculitis, or psoriasis. The subject can also have an allergic disorder such as Asthma.

It is contemplated that the GSNO and/or at least one GSNO reductase inhibitor may be administered in combination with one or more additional therapies. The additional therapies may comprise anti-inflammatories, immune-modulating agents, and/or immunosuppressive therapies. The additional therapy may be a therapy known in the art for the treatment of diabetes or an autoimmune disease, such as multiple sclerosis.

As used herein, "treating" describes the management and care of a patient for the purpose of combating a disease, condition, or disorder and includes the administration of a compound of the present invention to prevent the onset of the symptoms or complications, alleviating the symptoms or complications, or eliminating the disease, condition or disorder. More specifically, "treating" includes reversing, attenuating, alleviating, minimizing, suppressing or halting at least one deleterious symptom or effect of a disease (disorder) state, disease progression, disease causative agent (e.g., bacteria or viruses), or other abnormal condition. Treatment is continued as long as symptoms and/or pathology ameliorate.

The patient can be any animal, domestic, livestock or wild, including, but not limited to cats, dogs, horses, pigs and cattle, and preferably human patients. As used herein, the terms patient and subject may be used interchangeably.

The GSNO or GSNO reductase inhibitors can be utilized in any pharmaceutically acceptable dosage form, including but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc. Specifically, the GSNO reductase inhibitors described herein can be formulated: (a) for administration selected from the group consisting of oral, pulmonary, intravenous, intra-arterial, intrathecal, intra-articular, rectal, ophthalmic, colonic, parenteral, intracisternal, intravaginal, intraperitoneal, local, buccal, nasal, and topical administration; (b) into a dosage form selected from the group consisting of liquid dispersions, gels, aerosols, ointments, creams, tablets, sachets and capsules; (c) into a dosage form selected from the group consisting of lyophilized formulations, dry powders, fast melt formulations, controlled release formulations, delayed release formulations, extended release formulations, pulsatile release formulations, and mixed immediate release and controlled release formulations; or (d) any combination thereof.

Oral compositions generally include an inert diluent or an edible carrier. They can be enclosed, for example, in gelatin capsules or compressed into tablets. For the purpose of oral therapeutic administration, the GSNOR inhibitor can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of GSNO or GSNOR inhibitor calculated to produce the desired therapeutic effect in association with the required pharmaceutical carrier. The specification for the dosage unit forms of the invention are dictated by and directly dependent on the unique characteristics of the GSNO or GSNOR inhibitor and the particular therapeutic effect to be achieved, and the limitations inherent in the art of compounding such an active agent for the treatment of individuals.

Pharmaceutical compositions according to the present disclosure comprising GSNO and/or at least one GSNOR inhibitor can comprise one or more pharmaceutical excipients. Examples of such excipients include, but are not limited to binding agents, filling agents, lubricating agents, suspending agents, sweeteners, flavoring agents, preservatives, buffers, wetting agents, disintegrants, effervescent agents, and other excipients. Such excipients are known in the art. Exemplary excipients include: (1) binding agents which include various celluloses and cross-linked polyvinylpyrrolidone, microcrystalline cellulose, such as Avicel® PH101 and Avicel® PH102, silicified microcrystalline cellulose (ProSolv SMCC™), gum tragacanth and gelatin; (2) filling agents such as various starches, lactose, lactose monohydrate, and lactose anhydrous; (3) disintegrating agents such as alginic acid, Primogel, corn starch, lightly crosslinked polyvinyl pyrrolidone, potato starch, maize starch, and modified starches, croscarmellose sodium, crospovidone, sodium starch glycolate, and mixtures thereof; (4) lubricants, including agents that act on the flowability of a powder to be compressed, include magnesium stearate, colloidal silicon dioxide, such as Aerosil® 200, talc, stearic acid, calcium stearate, and silica gel; (5) glidants such as colloidal silicon dioxide; (6) preservatives, such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride; (7) diluents such as pharmaceutically acceptable inert fillers, such as microcrystalline cellulose, lactose, dibasic calcium phosphate, saccharides, and/or mixtures of any of the foregoing; examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose; (8) sweetening agents, including any natural or artificial sweetener, such as sucrose, saccharin sucrose, xylitol, sodium saccharin, cyclamate, aspartame, and acesulfame; (9) flavoring agents, such as peppermint, methyl salicylate, orange flavoring, Magnasweet® (trademark of MAFCO), bubble gum flavor, fruit flavors, and the like; and (10) effervescent agents, including effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease.

II. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Effect of GSNO

Effect of GSNO Supplementation on Cognitive Behavior:

Radial arm maze was used to assess special memory and learning. Diabetic mice showed a significant deficit in spatial cognition in the radial eight-arm maze task, as indicated by a lower percentage of correct choices (25%), lower percentage retention and a higher number of working and reference memory errors (nearly 2 fold) compared to control group (FIG. 1). GSNO at a dose of 100 µg/kg body weight caused a significant increase in the percentage of correct choices (30%) and significantly lowered the number of errors (44%) thereby suggesting improvement in cognition. The parameters for GSNO-treated control mice were not significantly different from control mice.

Figure 2A:
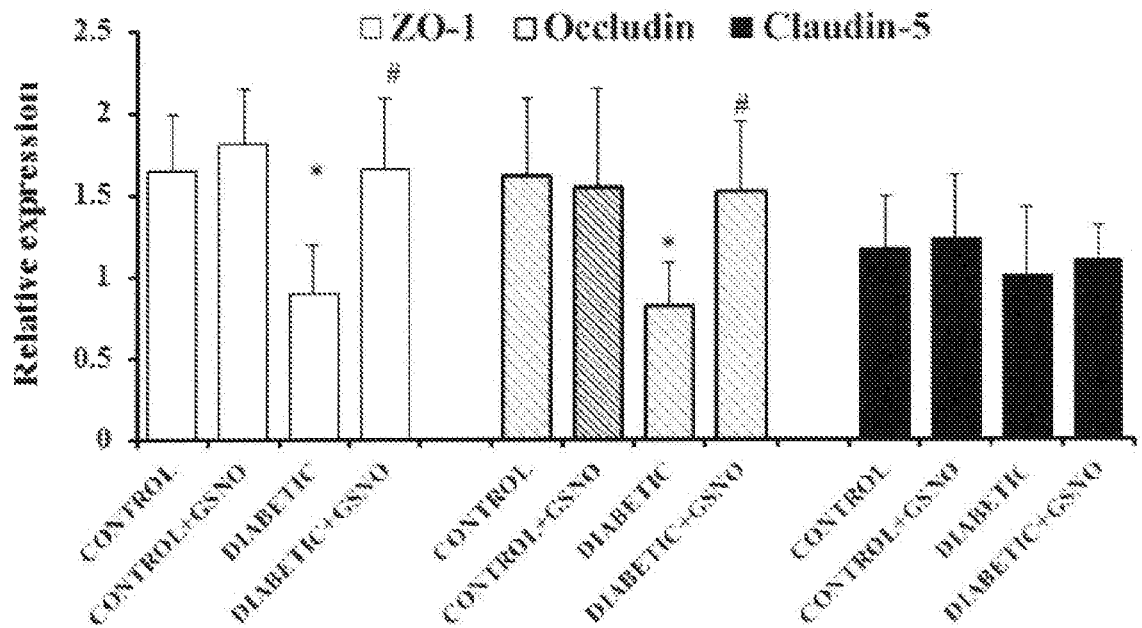
FIGS. 2A-2B: Effect of GSNO administration on ZO-1, occludin, claudin-5 relative mRNA expression in (A) Cortex and (B) Hippocampus after 8 weeks of induction of diabetes. * Significantly different from control group ($p<0.05$). # Significantly different from diabetic group ($p<0.05$). Values are expressed as mean±SD; n=6/group.
Figure 2B:
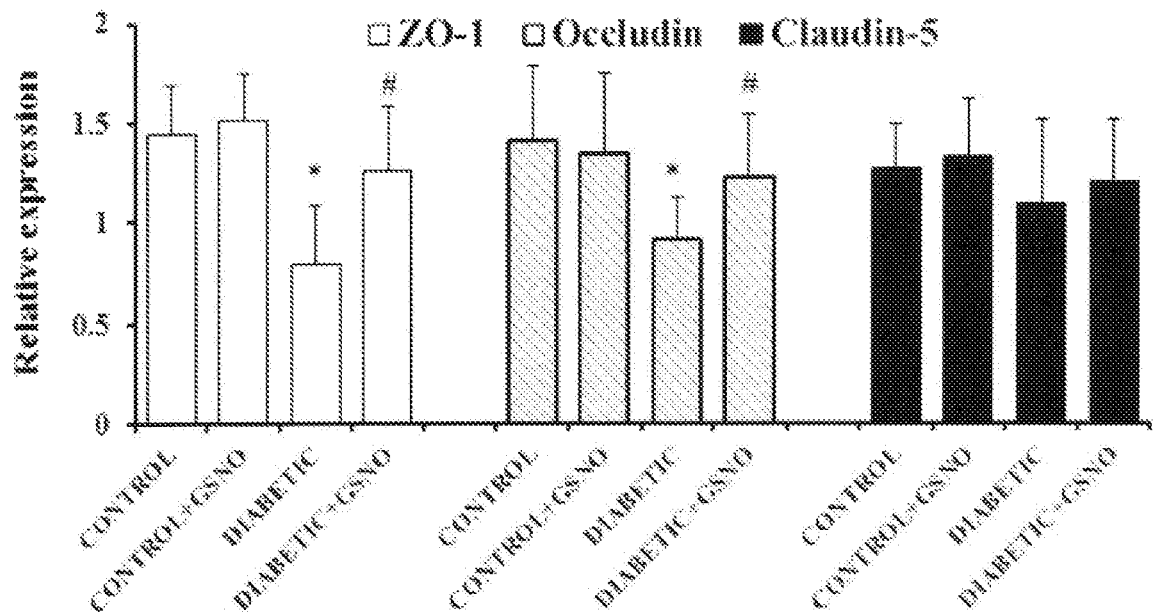

Effect of GSNO Supplementation on mRNA Expression of Tight Junction Proteins (ZO-1, Occludin, Claudin-5):

The role of tight junction proteins (ZO-1, Occludin, Claudin-5) in diabetic brain was investigated in terms of their mRNA expression to determine the changes at transcriptional level that may account for increased BBB permeability. Relative mRNA expression of ZO-1 and occludin was found to be significantly decreased in cortex and hippocampus by nearly 2-fold in diabetic animals as compared to control group. On the other hand, GSNO supplementation to diabetic animals was able to significantly normalize the mRNA expression of ZO-1 and occludin (2-fold) in both the regions almost comparable to control levels. However, there was no significant change observed in the mRNA expression of claudin-5 in diabetic and GSNO treated diabetic animals (FIG. 2).

Figures 3A, 3B:
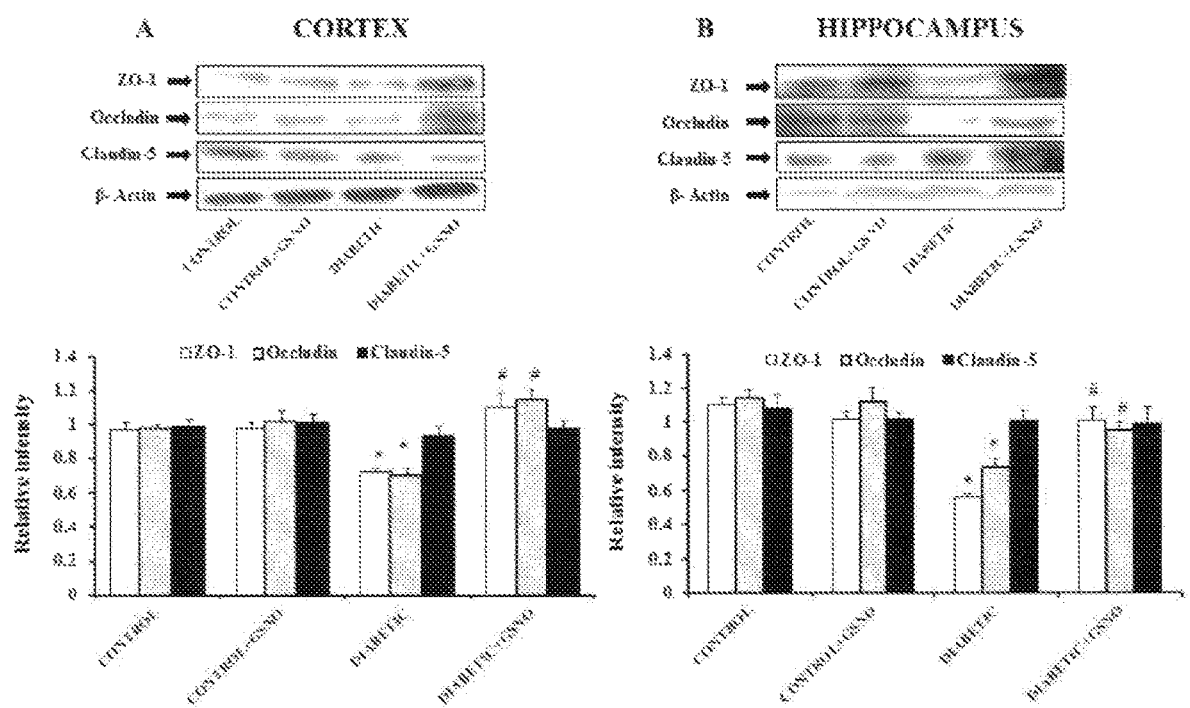
FIGS. 3A-3B: Effect of GSNO administration on relative protein expression of ZO-1, occludin, claudin-5 in (A) Cortex and (B) Hippocampus after 8 weeks of induction of diabetes. (i) Bands depict ZO-1, Occludin, Claudin-5 protein expression; (ii) Densitometric analysis of ZO-1, Occludin, Claudin-5 relative protein expression. Values are expressed as mean±SD: n=3. *Significantly different from control group ($p<0.05$); # Significantly different from diabetic group ($p<0.05$).

Effect of GSNO Supplementation on Protein Expression of Tight Junction Proteins (ZO-1, Occludin, Claudin-5):

To study changes in tight junction proteins associated with assembly of BBB, protein expression of ZO-1, Occludin, Claudin-5 has been determined in isolated microvessels from cortex and hippocampus of diabetic mice by western blotting. Expression of ZO-1 and occludin were significantly decreased in cortex (30%, 36% respectively) and hippocampus of STZ induced diabetic animals as compared to control group. Whereas, GSNO administration was able to significantly accentuate the protein expression of ZO-1 and occludin in both the regions by nearly 70% and 60%. However, there was no significant change in the protein expression of claudin-5 in diabetic and GSNO treated diabetic animals (FIG. 3).

Figures 4A, 4B, 4C:
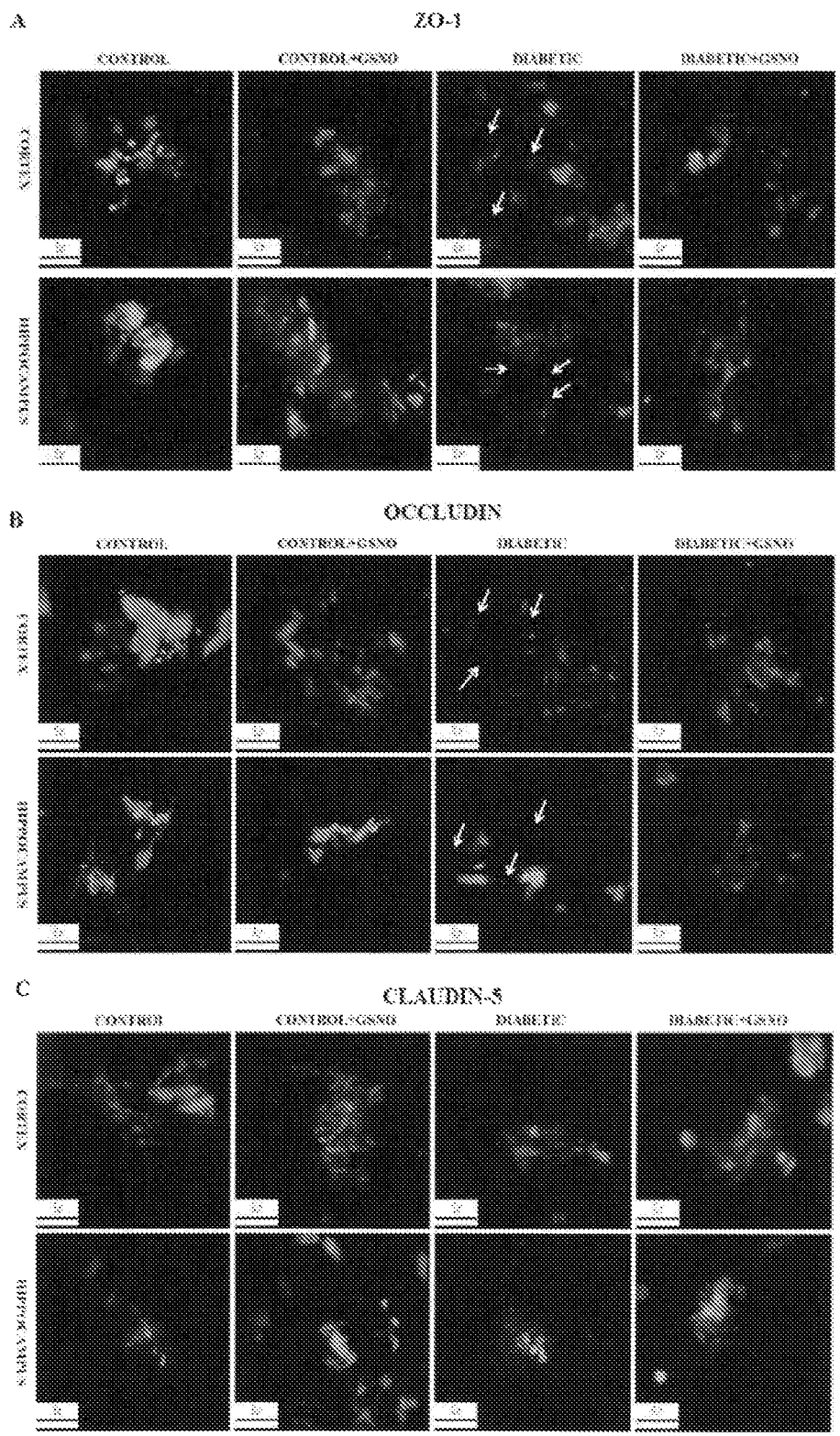
FIGS. 4A-4C: Images representing the effect of GSNO administration on expression of (A) ZO-1; (B) Occludin and (C) Claudin-5 in isolated microvessels obtained from cortex and hippocampus subjected to immunofluorescence after 8 weeks of induction of diabetes. (Magnification=40×; Scale bar=50 µm).

Effect of GSNO Supplementation on Immunofluorescence of Tight Junction Proteins (ZO-1, Occludin, Claudin-5):

Immunofluorescence of tight junction proteins was carried out to study the regional localization of tight junction proteins in isolated microvessels from the cortex and hippocampus of diabetic animals and to determine the changes associated with BBB. Isolated microvessels stained for ZO-1, occludin and claudin-5 showed distinct pattern of fluorescence in brain microvessels indicative of concentration of these proteins at the junctions of the endothelial cells (FIG. 4). No changes in junctional localization were observed for ZO-1, occludin or claudin-5 in microvessels of cortex and hippocampus obtained from diabetic animals. However, the fluorescent intensity for both ZO-1 and occludin appeared to be reduced, consistent with western blot data. In contrast, microvessels obtained from brain tissue of GSNO supplemented diabetic animals showed an increased fluorescent intensity for both ZO-1 and occludin as compared to untreated diabetic group (FIG. 4A, B). No change was observed in claudin-5 fluorescent intensity in both diabetic and GSNO treated diabetic animals (FIG. 4C).

Figures 5A, 5B:
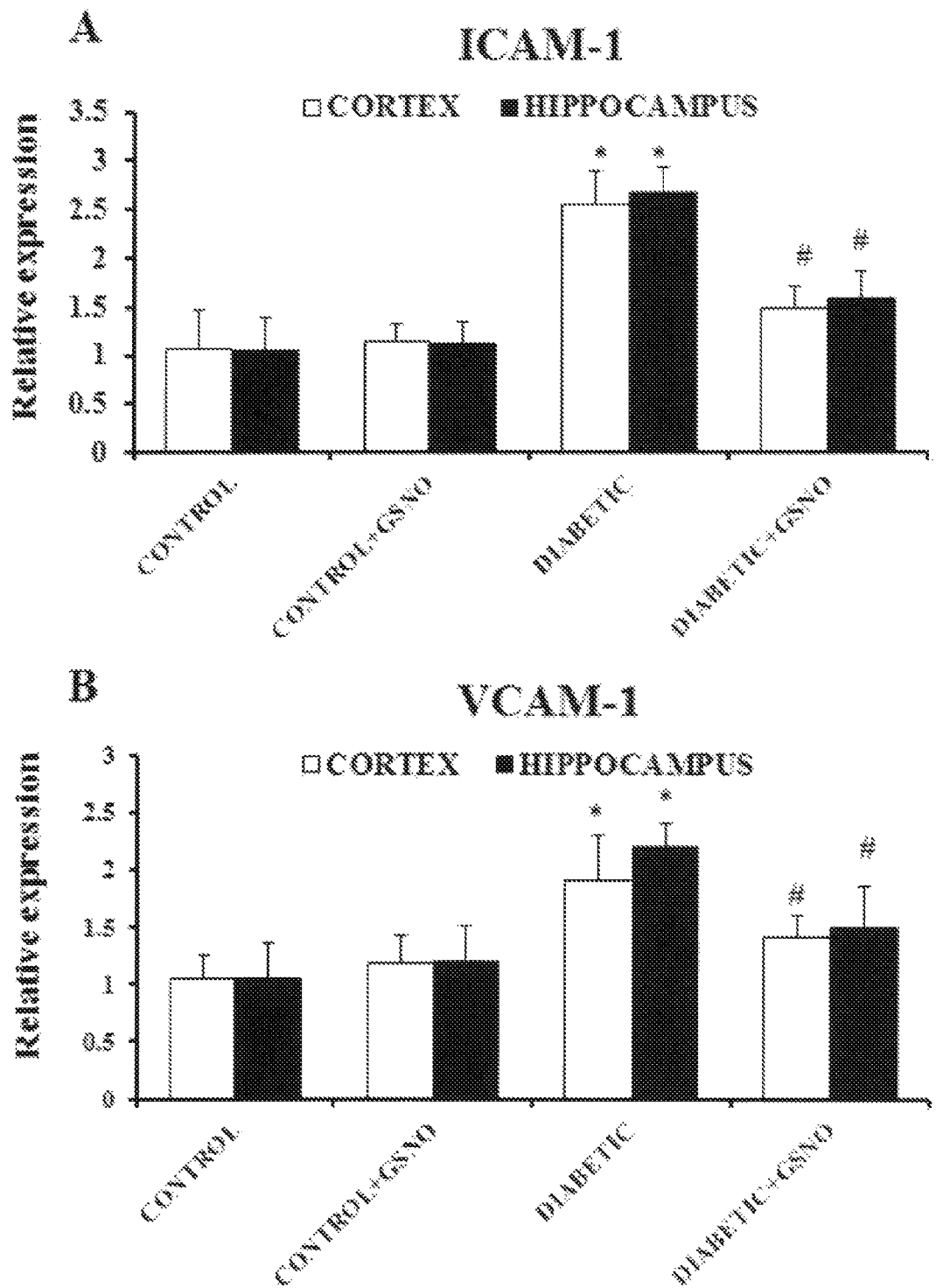
FIGS. 5A-5B: Effect of GSNO administration on relative mRNA expression of (A) ICAM-1 and (B) VCAM-1 in cortex and hippocampus after 8 weeks of induction of diabetes. * Significantly different from control group ($p<0.05$). # Significantly different from diabetic group ($p<0.05$). Values are expressed as mean±SD; n=6/group.

Effect of GSNO Supplementation on mRNA Expression of Cell Adhesion Molecules (ICAM-1 and VCAM-1):

mRNA expression for cell adhesion molecules (ICAM-1 and VCAM-1) was studied to understand their role in mediating BBB dysfunction at transcriptional level in diabetic condition. It was observed that mRNA expression of ICAM-1 and VCAM-1 was found to be significantly increased in cortex and hippocampus of diabetic animals by 2-fold as compared to control group. However, GSNO supplementation to diabetic animals was able to normalize the mRNA expression of ICAM-1 in both the regions comparable to control levels (FIG. 5).

Figures 6A, 6B:
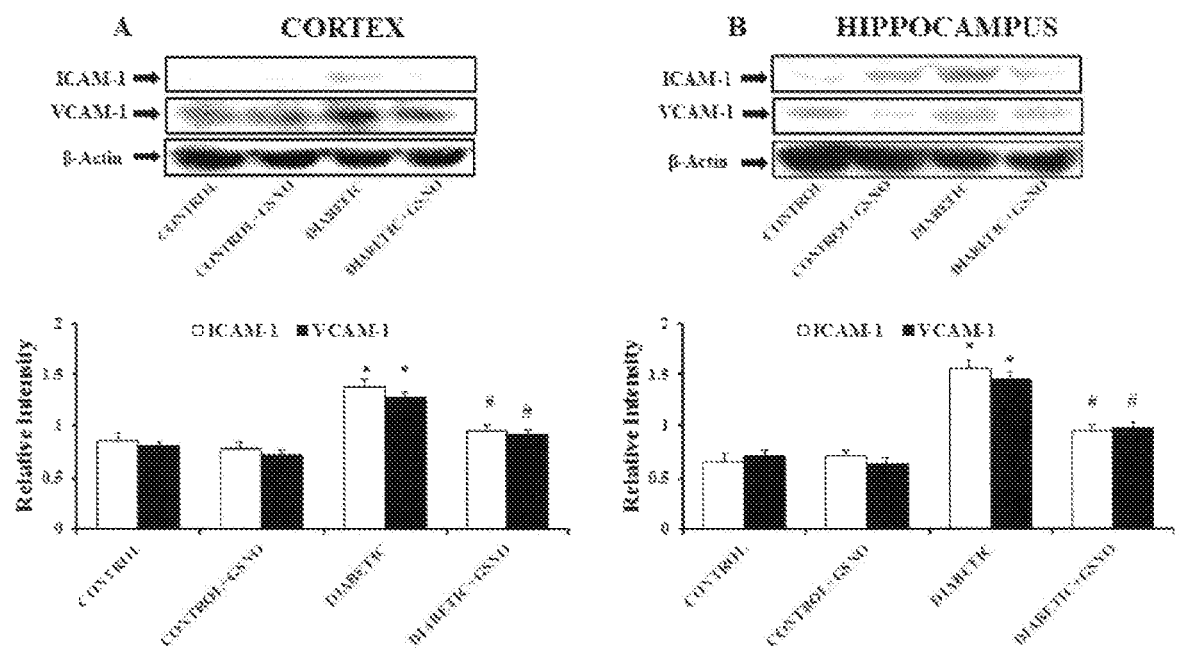
FIGS. 6A-6B: Effect of GSNO administration on relative protein expression of ICAM-1 and VCAM-1 in (A) Cortex and (B) Hippocampus after 8 weeks of induction of diabetes. (Top) Western blot bands depict ICAM-1 and VCAM-1 protein expression; (bottom) Densitometric analysis of ICAM-1 and VCAM-1 relative protein expression. Values are expressed as mean±SD: n=3. *Significantly different from control group ($p<0.05$); # Significantly different from diabetic group ($p<0.05$).

Effect of GSNO Supplementation on Protein Expression of Cell Adhesion Molecules (ICAM-1 and VCAM-1):

Changes in protein expression of ICAM-1 and VCAM-1 in isolated microvessels from cortex and hippocampus was determined to interpret its association with regulation of BBB permeability in diabetes. Protein expression of ICAM-1 and VCAM-1 was significantly increased in cortex and hippocampus of diabetic animals by 2 times as compared to control group. Whereas, GSNO administration was able to significantly mitigate its protein expression in both the regions as compared to untreated diabetic group (FIG. 6).

Effect of GSNO Supplementation on Ultrastructure of Microvessels:

Microvessel ultrastructure in the CNS consist of an endothelial cell layer, the basal lamina derived from the extracellular matrix (ECM), layers of smooth muscle cells encased in ECM surrounded by the astrocyte end-feet (del Zoppo & Mabuchi 2003). Studying ultrastructure of microvessels provide insight into the extent of damage caused by hyperglycemia to BBB. Transmission electron microscopy (TEM) was employed to detect the changes in cerebral microvessels in experimental model of diabetes.

TABLE 1

Sequences of primer pairs used in real-time PCR.

| Gene | Accession number | Forward Sequence (5'-3') | Reverse Sequence (3'-5') | Amplicon (bp) |
| --- | --- | --- | --- | --- |
| ICAM-1 | NM_010493 | CCGCAGGTCCAATTCACACT (SEQ ID NO: 1) | CAGAGCGGCAGAGCAAAAG (SEQ ID NO: 2) | 72 |
| VCAM-1 | NM_011693 | GGGAAGCTGGAACGAAGTATCC (SEQ ID NO: 3) | TCTGGAGCCAAACACTTGACTGT (SEQ ID NO: 4) | 119 |
| ZO-1 | NM_009386 | AAGCCAGCCTCTCAACAGAAAGCAG (SEQ ID NO: 5) | AGGCTGTGATGCGTGCGAGC (SEQ ID NO: 6) | 168 |
| Occludin | NM_008756 | GCTGTGATGTGTGTTGAGCT (SEQ ID NO: 7) | GACGGTCTACCTGGAGGAAC (SEQ ID NO: 8) | 71 |
| Claudin-5 | NM_013805 | CTGGACCACAACATCGTGAC (SEQ ID NO: 9) | GCCGGTCAAGGTAACAAAGA (SEQ ID NO: 10) | 198 |
| GAPDH | NM_00804 | ATGACATCAAGAAGGTGGTG (SEQ ID NO: 11) | CATACCAGGAAATGAGCTTG (SEQ ID NO: 12) | 176 |

Figures 7A, 7B:
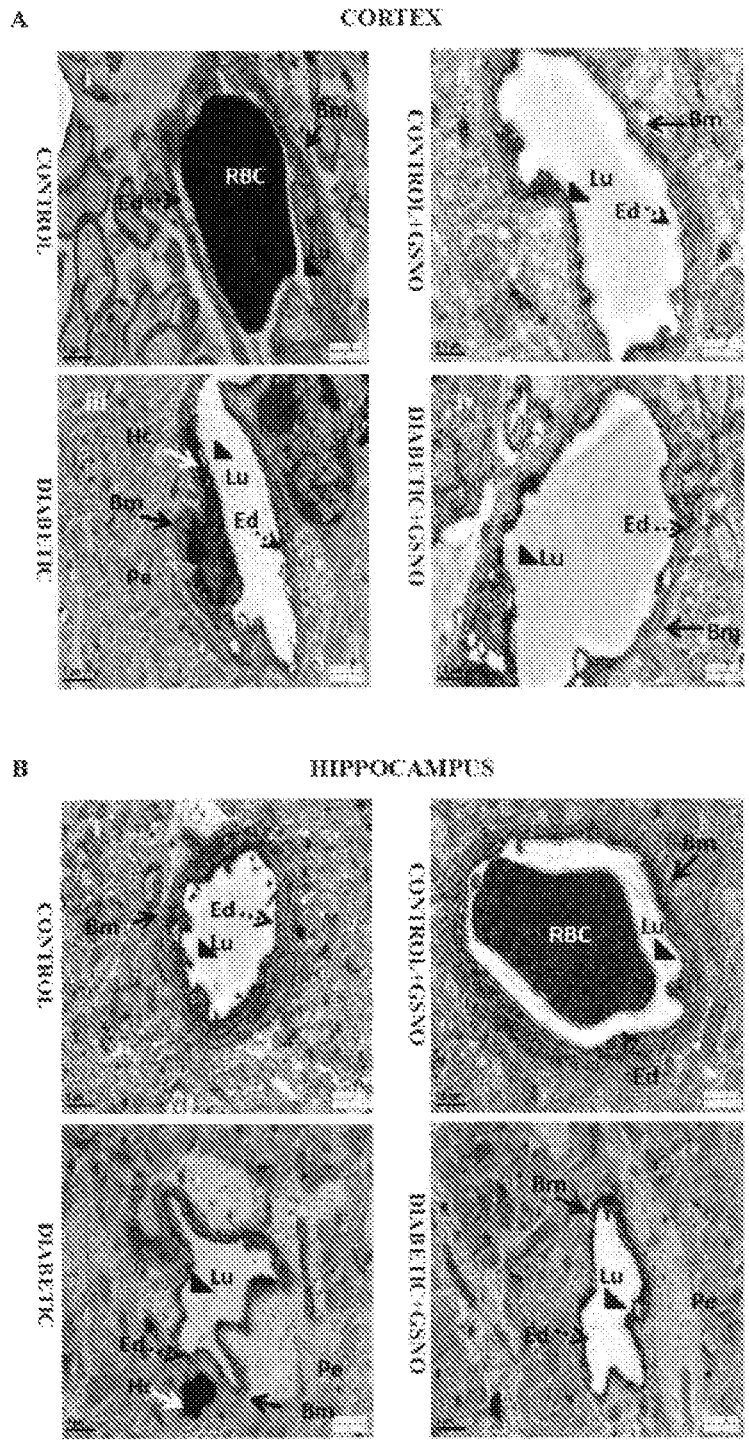
FIGS. 7A-7B: Images representing the effect of GSNO administration on ultrastructure of microvessels obtained from (A) Cortex (i, iii—Magnification=2550×, Scale bar=1 µm; ii, iv Magnification=5000×, Scale bar=0.5 µm) and (B) Hippocampus (i, iii, iv Magnification=2550×, Scale bar=1 µm; ii—Magnification=5000×, Scale bar=0.5 µm) subjected to transmission electron microscopy after 8 weeks of induction of diabetes. Black triangles indicate capillary lumen (Lu), black arrows indicate basement membrane (Bin), dotted black arrow (Ed) and white arrows indicate heterochromatin (He).

The microvessels of control and GSNO supplemented control mice obtained from cortex and hippocampus exhibited smooth and intact lumen (black triangle) with RBCs passing through them and continuous basement membrane with uniform electron density. Moreover, the endothelial cell layer (dotted black arrow) was found to be closely attached to the basement membrane (FIG. 7 Ai, Bi). On the other hand, after 8 weeks of diabetes induction microvessels of cortex and hippocampus appeared to show endothelial cell pyknosis, lumen stenosis (black triangle), basement membrane thickening (black arrow), perivascular edema (grey arrow) and heterochromatin (white arrow). Moreover, the endothelial cell layer (dotted black arrow) was found to be loosely attached to the basement membrane suggesting degradation of tight junction proteins (FIG. 7 Aiii, Biii). However, the ultrastructure of cerebral cortex microvessels in the GSNO supplemented diabetic animals exhibited a relatively unobstructed capillary lumen, clear pericytes, continuous basement membrane quite firmly attached to endothelial layer (FIG. 7 Aiv, Biv). These findings clearly implicated that ultrastructure of microvessels in cortex and hippocampus of diabetic animals was found to be aberrated thereby suggesting damaged neurovascular unit that comprise of BBB. GSNO administration to diabetic animals improved the ultrastructure of the damaged microvessels thereby improving BBB disruption.

Therefore, it was concluded that STZ induction in diabetic mice causes significant loss of tight junction proteins (ZO-1 and occludin) and upregulation of cell adhesion molecules (ICAM-1, VCAM-1) in cortex and hippocampus regions thereby forming aberrant BBB. GSNO supplementation was able to preserve BBB architecture by preventing the loss of these tight junction proteins and downregulating the expression of cell adhesion molecules. These findings suggest that administration of GSNO has a protective effect against hyperglycaemia associated CNS deficits suggesting its therapeutic potential in chronic diabetics.

Example 2—Materials and Methods

Chemicals:

All the chemicals were obtained from Sigma Chemical Co. (St. Louis, USA), Merck (Mumbai, India), Himedia (Mumbai, India) and Sisco Research Laboratories Pvt. Ltd. (Mumbai, India). Streptozotocin (STZ) and GSNO was obtained from Sigma Chemical Company, St Louis, USA and World Precision Instruments (Sarasota, USA). Primers were obtained from IDT (Coralville, USA) and SYBR Green was obtained from Roche Diagnostics (Mannheim, Germany). RevertAid® H minus first strand cDNA synthesis kit was procured from Thermo Scientific Inc. (Waltham, USA). Polyvinylidene Difluoride (PVDF) membrane was obtained from Immobilon™-P, Millipore (Darmstadt Germany). Primary antibodies for VCAM-1, ICAM-1, iNOS, occludin, ZO-1, claudin-5 and f-actin were purchased from Santa Cruz Biotechnology (Santa Cruz, USA). Secondary antibody HRP linked anti mouse IgG, anti-goat and anti-rabbit IgG were obtained from Sigma-Aldrich (St. Louis, USA).

Experimental Design:

Male laca mice weighing between 28-32 g were procured from the Central Animal House, Panjab University, Chandigarh. The animals were acclimatized and were fed with standard pellet diet and water ad libitum. The experimental protocols were approved by the Institutional Ethics Committee and were conducted according to Indian National Science Academy (INSA) guidelines for the use and care of experimental animals. The animals were divided into four groups: (i) Control animals received phosphate buffered saline (PBS) throughout the study; (ii) Control+GSNO animals were administered with GSNO 100 μg/kg body weight orally, dissolved in PBS after every 24 h for 8 weeks; (iii) Diabetic animals were injected with STZ at a dose of 40 mg/kg body weight intraperitoneally for 5 days dissolved in 0.1 mol/L citrate buffer, pH 4.5 and Diabetic+GSNO mice were administered GSNO 100 μg/kg body weight orally dissolved in PBS after every 24 h for 8 weeks after the induction of diabetes. Animals were assessed weekly for development of diabetic encephalopathy in terms of memory deficits. All experimental procedures were done on mice at the end of study.

Radial Arm Maze:

Radial arm maze was used to assess specific learning and memory in the radial arm maze (Veena et al., 2009). Its apparatus consisted of equally spaced arms (35×9×5 cm) radiating from an octagonal central platform, and the maze was kept 80 cm elevated from the ground. Prior to the acquisition, all the arms were baited and mice were allowed to explore the maze for 10 min and were subjected to two such acclimatization sessions on consecutive days. During acquisition period, the mouse was placed in the center of the octagon and was allowed to find the rewards in the four alternatively baited arms. An arm choice was recorded when the animal reached the end of an arm. An arm entry was counted when all four paws entered the arm. The trial continued until the mouse entered all the four baited arms or 5 min had elapsed. At the end of the trial, the mouse was returned to the home cage and was given the second trial after an interval of 1 h. Training was continued until the mice attained the criteria of 80% correct choice (at least 4 correct entries out of 5 entries). After acquisition period, animals were evaluated for retention of the task. Mice were given two trials and the average of the two trials was taken for analysis. The data were analyzed for the number of reference memory errors (exploring an arm never baited), working memory errors (exploring a baited arm already visited), total number of errors, memory retention and % correct choice.

Microvessel Isolation:

The microvessels were isolated by the method described by Brooks et al., (2005). Brain tissue was homogenized in microisolation buffer (103 mM NaCl, 4.7 mM KCl, 2.5 mM CaCb, 1.2 mM KH2PO$_4$, 1.2 mM MgSO$_4$, 15 mM HEPES, 2.5 mM NaHCO$_3$, 10 mM D-glucose, 1 mM sodium pyruvate and 10 g/L dextran (64,000 mol wt), pH 7.4) and equal amount of 26% (w/v) dextran was added. The sample was then centrifuged at 5600 g for 10 min and pellets obtained were resuspended in microisolation buffer. Then the suspension was filtered through 70 μm filter (BD Biosciences, Gurgaon, India). The filtered homogenates were then centrifuged at 3000 g for 10 min at 4° C. and the pellet was obtained.

Western Blotting:

Protein expression of tight junction proteins and cell adhesion molecules i.e. ZO-1, occludin, Claudin-5, ICAM-1 and VCAM-1 was studied in microvessels obtained from cortex and hippocampus regions of the brain (Towbin et al., 1992). The microvessel pellets were extracted with 6 M urea lysis buffer (6 M urea, 0.1% Triton X-100, 10 mM Tris-HCl, pH 8.0, 1 mM dithiothreitol, 5 mM MgCb, 5 mM EGTA, and 150 mM NaCl) with the protease inhibitor cocktail. Sample containing 50 μg of protein was separated on 10% sodium dodecyl sulfate-polyacrylamide gel along with pre-stained protein marker. The protein from the gel was transferred to the polyvinylidene difluoride membrane in an ice cold buffer (25 mM Tris HCl, 192 mM glycine, and 20% methanol) for 2 h. Non-specific binding of antibodies was blocked by incubating the membrane with 5% skim milk in PBS for 2 h at 25° C. After three consecutive washings with PBS and PBS-Tween, the membrane was probed with primary antibodies for ICAM-1 (1:1000), VCAM-1 (1:1000), ZO-1 (1:500), Occludin (1:500), Claudin-5 (1:1000) and P-actin (1:2000) in 2.5% skimmed milk in PBS with gentle shaking for 3 h. The membrane was again washed and incubated with the respective horse radish peroxidase conjugated secondary antibodies (1:5000) in 2.5% skimmed milk in PBS for 1 h. The proteins were visualized using chemiluminescence kit (Bio-Rad Laboratories, Hercules, Calif., USA). Finally, the protein bands were visualized using Gel documentation system and densitometric analysis was performed using Image J software.

Immunofluorescence:

Isolated microvessels were resuspended in PBS and allowed to attach to polylysine-coated slides for 30 min at 37° C. and fixed at 95° C. for 10 min. Then, it was followed by fixation with 4% formaldehyde in PBS for 10 min and permeabilized with 0.1% Triton X-100 in PBS for 5 min. Then, the slides were blocked for 2 h in PBS with 2% BSA and washed 3 times with PBS and PBS-Tween. Slides were then incubated with primary antibodies ZO-1 (1:200), occludin (1:100), and Claudin-5 (1:200) in PBS with 1% BSA overnight at 4° C. and were again washed 3 times with PBS and PBS-Tween. Slides were then incubated with FITC conjugated anti-rabbit (1:1000) or anti-mouse IgG (1:1000) in 1% BSA in PBS for 1 h. After placement and sealing of coverslips, photographs were taken with 40× objective on a Nikon TE-300 fluorescence microscope with a fluorescein filter (Schulze & Firth 1993).

Real Time:

PCR Total RNA was extracted from microvessels obtained from brain tissue using TriReagent®. To eliminate genomic DNA contamination, RNA samples were treated with DNase. To each sample, 1 μL of DNase and 1 μL of reaction buffer was added. The concentration of RNA obtained was determined by 260/280 nm ratio using a Nanodrop™ Spectrophotometer (Nanodrop™ 1000, Thermo Scientific®, Waltham, USA). The integrity and overall quality of RNA was evaluated using agarose gel electrophoresis. Further, cDNA synthesis was carried out from the purified total RNA (1 μg) using cDNA synthesis kit (Thermo Scientific® RevertAid® H Minus First Strand cDNA Synthesis Kit) in accordance with the manufacturer's instructions. The cDNA obtained was stored at −20° C. for amplification by Real-time PCR. For qRT-PCR, primers for various genes were chosen using Primer-BLAST tool (NCBI) and custom synthesized by IDT® (Coralville, Iowa, USA) as provided in Table 1. For Real-time PCR, 10 ng of cDNA was mixed with gene specific primers, SYBR Green 1 Master (2×) (Fast start Taq DNA polymerase, reaction buffer, dNTP mix, SYBR green 1 dye, MgCl$_2$) and subjected to PCR amplification (one cycle at 50° C. for 2 min, one cycle at 95° C. for 10 min, and 40 cycles at 95° C. for 10 s, 59° C. for 10 s, 72° C. for 10 s, and 60° C. for 1 min). The data obtained was analyzed by the LightCycler 480 Software, Version 1.5. To verify size and specificity of PCR reaction the resulting amplicon products were visualized on an agarose gel. Glyceraldehyde-3-phosphate dehydrogenase was used as the reference gene and the relative gene expression was determined using delta-delta Ct method as described by Pfaffl et al., (2002).

Transmission Electron Microscopy:

Transmission electron microscopy was carried out by the method described by Gao et al., (2005). Cerebral cortex and hippocampus were dissected and small blocks of about 1 mm3 were cut and fixed in Kamowsky fixative [2.5% (v/v) glutaraldehyde & 2% (v/v) paraformaldehyde in 0.1 M phosphate buffer, pH 7.4] for 24 h at 4° C. Post fixation of samples was carried out for 2 h at 4° C. in 1% osmium tetroxide in 0.1 M phosphate buffer, (pH 7.4). Thereafter, the samples were washed in 0.1 M phosphate buffer to remove extraneous traces of osmium tetroxide for 1 h followed by dehydration in ascending grades of acetone (30%, 50%, 70%, 90% and 100%) and washing with toluene. The samples were then processed for embedding using CY212 Araldite by passing them through a sequence of media

[Araldite:Toluene (1:3) for 1 h; Araldite:Toluene (1:1) for 1 h; Araldite:Toluene (3:1) for 1 h]. Tissue embedding was carried out in the araldite medium using beam capsule. To ensure complete polymerization the liquid araldite embedding medium was polymerized at 50° C. in an oven for 18 h followed by increasing the temperature to 60° C. for 36 h. Semi-thin sections of about 1 μm thickness were cut using very sharp glass knives and stained with 0.5% (w/v) to ludine blue made in 1% (w/v) borax solution for examination under light microscope. The area of interest was selected and the blocks were further trimmed to form ultra-thin sections of 60-80 nm thickness using ultra-microtome (Ultracut E, Reichert Jung, Austria). The ultra-thin sections were mounted on copper grids of 100-300 mesh size and were double stained in alcoholic uranyl acetate (10 min) as well as lead acetate (10 min). These sections obtained were finally viewed under transmission electron microscope (FEI Morgagni™ 268d, The Netherlands) being operated at 100 KV at Electron microscopy facility, All India Institute of Medical Science (AIIMS), New Delhi, India.

Protein Estimation:

Protein content was estimated according to the method of Lowry et al., (1951).

Statistical Analysis:

All values were expressed as mean±SD. Data was analyzed by one-way analysis of variance followed by Newman-Keuls test for multiple pair-wise comparisons, using SPSS 16 software. Values with $p \leq 0.05$ were considered statistically significant.

Example 3—GSNO Reductase Inhibitor for Treatment of Multiple Sclerosis

Figure 8A:
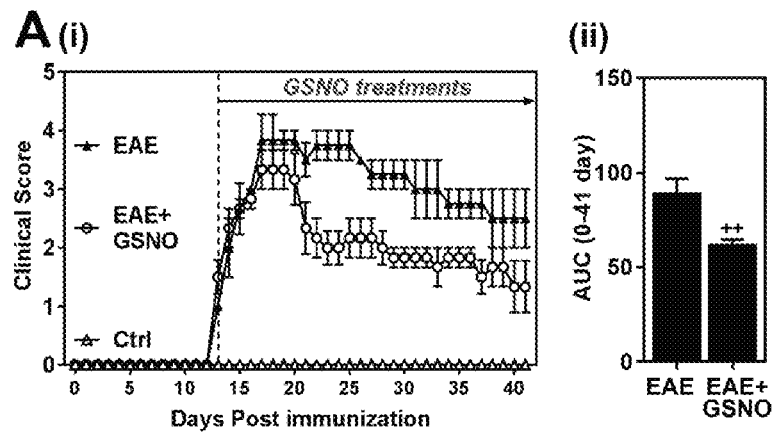
FIGS. 8A-8C: Exogenous GSNO attenuate EAE disease. A. C57BL\6 mice immunized with MOG peptide were treated with GSNO (1 mg/kg/day) on the day of disease onset (day 14 postimmunization). Following the immunization and GSNO treatment, clinical signs of EAE disease were assessed daily as described in materials and methods. B. At the peak of EAE disease, the spinal cord infiltration of mononuclear cells was analyzed by H&E staining. C. In addition, subset specific infiltration of CD4+ cells (TH1, TH2, TH17. FOXP3+ Treg, and FOXP3-Treg) were analyzed by flow-cytometry analysis
Figure 8B:
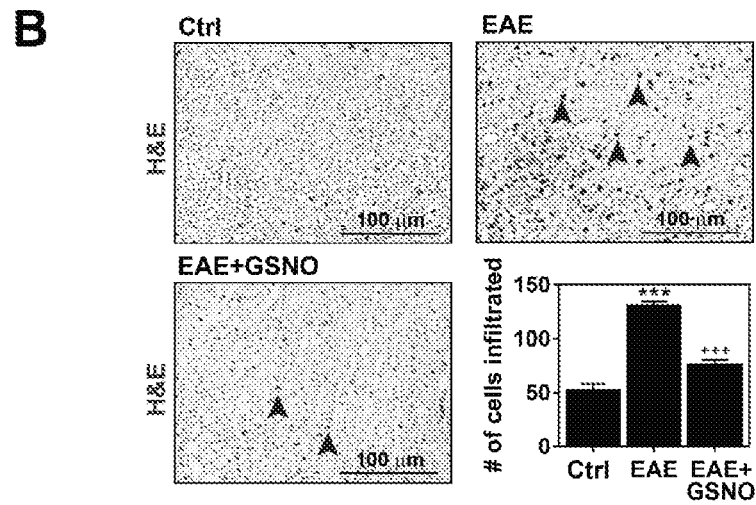

GSNO Treatment Attenuates EAE Disease Via Inhibiting the CNS Infiltration of TH17 Cells while Inducing the CNS Infiltration of CD4+CD25+ FOXP3− Treg Cells:

It was previously reported that GSNO treatment attenuated the EAE disease by inhibiting TH17 signaling pathways (STAT3/RORγt) but without affecting on TH1 (STAT4/T-bet) and TH2 (STAT6/GATA3) signaling pathways (Langrish et al., 2005). Accordingly, FIG. 8A shows that GSNO treatment of EAE mice significantly decreased EAE disease severity as shown by their clinical score [untreated EAE mice: 3.5±0.5. GSNO treated EAE mice: 3.1±0 76 at the peak of disease (day 21 of post immunization), untreated EAE mice: 2.5±0.5. GSNO treated EAE mice: 1.3±0.76 at the remission of disease (day 41 of post immunization)]. Accordingly, GSNO treatment also reduced mononuclear cell infiltration as shown by H&E staining (FIG. 8B).

Figure 8C:
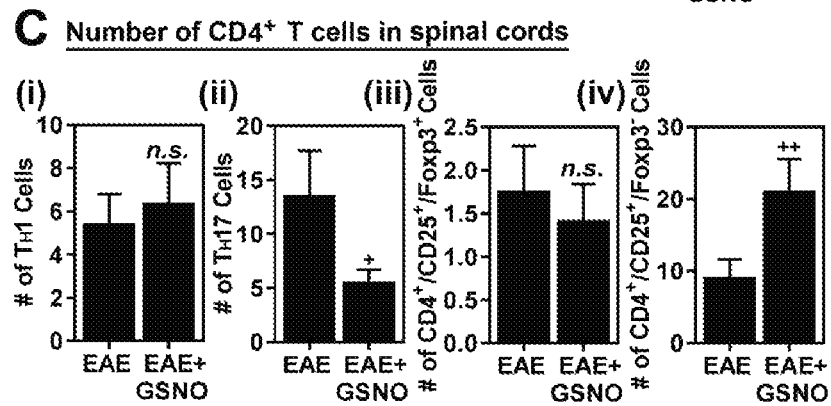

The degree of CNS infiltration of each subset of CD4+ T cells in EAE mice was next examined. Fluorescence flow cytometry analysis in FIG. 8C shows that GSNO treatment had no obvious effect on the numbers of CD4+ IFN-γ+ (TH1) cells but significantly decreased the number of $CD4^+$ IL-17 (TH17) cells in the spinal cords of EAE animals as reported previously (Langrish et al., 2005). In addition, GSNO treatment significantly increased the number of CD4+CD25+ FOXP3− Treg cells, which may represent 'NO-Treg' (Neidbala et al., 2007), without altering the number of CD4+CD25+ FOXP3+ Treg cells, which represent natural and/or inducible Tregs (nTreg and iTreg) (Curotto de Lataille and Lataille, 2009). Accordingly, the number of total Treg cells (CD4+CD25+) were increased in EAE mice treated with GSNO as compared to untreated EAE mice. These data indicate that GSNO treatment attenuates EAE disease via inhibiting the CNS infiltration of TH17 cells while inducing the CNS infiltration of CD4+CD25+ FOXP3− Treg cells.

Figures 9A, 9B:
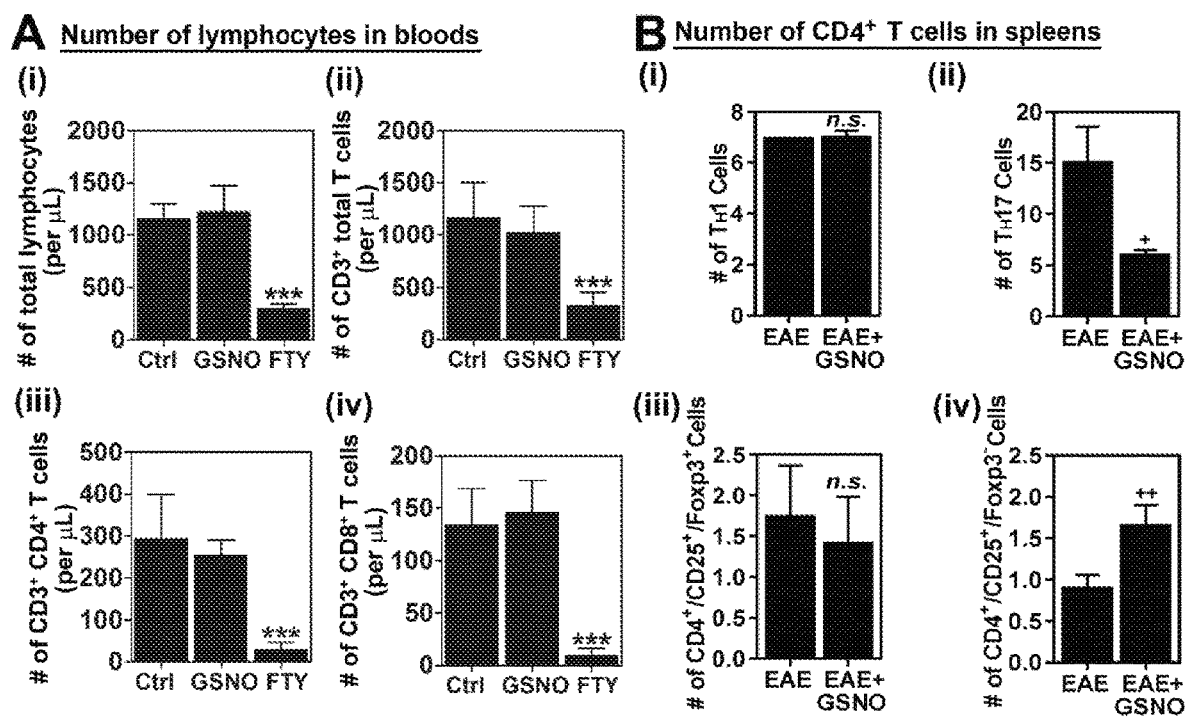
FIGS. 9A-9B: GSNO treatment differentially modulates subset specific polarization of CD4+ T cells in spleen without exhibiting lymphopenia-related effect. A. Normal mice (without EAE) were treated with saline (Ctrl). GSNO or FTY720 (FTY) for 19 days and the numbers of total lymphocytes (i), CD3+ T cells (ii). CD4+ T cells (iii), and CD8+ cells (iv) in bloods were analyzed. B. At the peak of disease. CD4+ T cells were isolated from the spleens of EAE mice treated with saline (EAE) or GSNO, re-stimulated with MOG peptide, and number of lineage specific CD4+ T cells, such as TH1 (i). TH17 (ii), total Treg (iii), FOXP3+ Treg (iv), and FOXP3- Treg (v), were counted by fluorescence flow-cytometry analysis.

GSNO Treatment Attenuates Subset Specific Polarization and Expansion of TH17 and CD4+CD25+ FOXP3− Tregs in Spleen without Exhibiting Global Lymphopenia-Related Effect:

To assess any potential lymphopenic effect of GSNO, normal C57BL\6 mice were treated with saline (Ctrl), GSNO (1 mg/kg/day/oral), or FTY720 (1 mg/kg/day/oral) as a positive drug control for 19 days and the numbers of total lymphocytes, CD3+ T cells, CD4+ T cells, and CD8+ cells in bloods were analyzed. FIG. 9A shows that GSNO treatment had no obvious effect on the numbers of these cells in blood while FTY720 (FTY) significantly reduced the numbers of those lymphocytes in blood, indicating that GSNO mediated reduction in spinal cord infiltration of mononuclear cells (FIG. 8B) and TH17 (FIG. 8C-ii) does not associate with lymphopenia-related effect. Next, the effect of GSNO treatment on the polarization/expansion of CD4+ T cells was investigated in the spleens of EAE mice. In accordance with the data of spinal cord infiltration (FIG. 8C), GSNO treatment had no obvious effect on the polarization/expansion of TH1 cells but significantly decreased the polarization/expansion of TH17 cells in the spleens of EAE animals. In addition, GSNO treatment significantly increased the polarization/expansion of $CD4^+$ $CD25^+$ $FOXP3^-$ Treg cells without altering the number of CD4+CD25+ FOXP3+ Treg cells. Accordingly, the polarization/expansion of total Treg cells (CD4+CD25+) were increased in EAE mice treated with GSNO as compared to untreated EAE mice. These data indicate that GSNO treatment attenuates EAE disease via inhibiting TH17 cells and/or inducing CD4+CD25+ FOXP3− Treg cells in their polarization, expansion, and CNS infiltration.

Figure 10A:
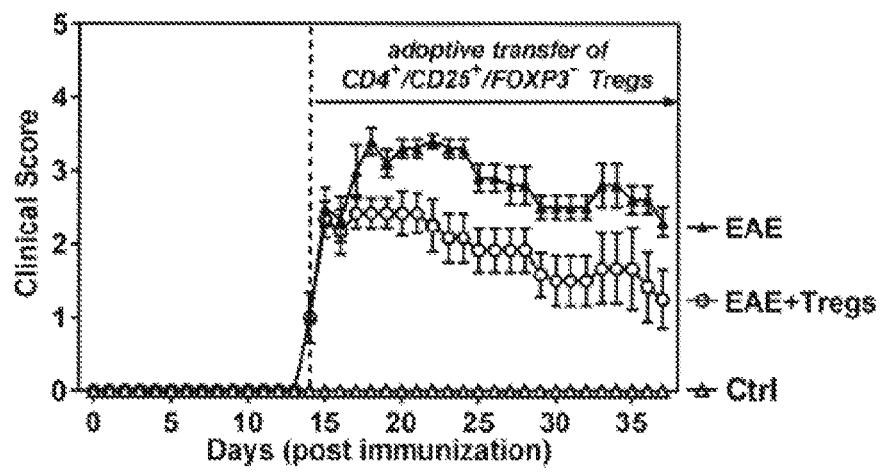
FIGS. 10A-10B: Immuno-modulatory role of CD4+/CD25+/FOXPJ- Treg in EAE disease. A. MOG specific CD4+CD25+ FOXP3- Treg cells induced by ex vivo treatment with GSNO were transferred to active EAE mice on the day of disease onset (day 14 post-immunization) and their clinical score were evaluated. B. At the peak of disease, expressions of IFN.
Figure 10B:
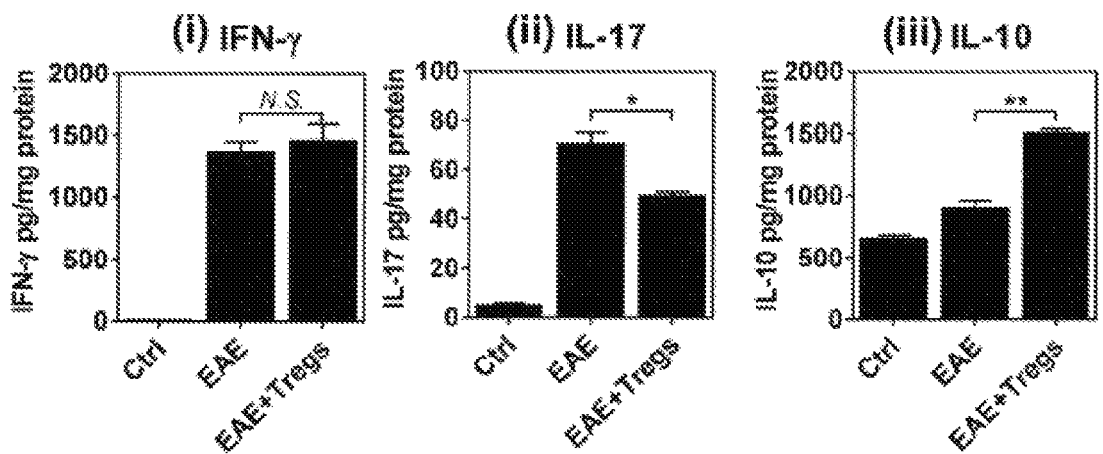

Immunomodulatory role of CD4+/CD25+/FOXP3− Treg in EAE disease: NO-inducible CD4+CD25+ FOXP3− Treg (NO-Treg) cells are known to attenuate EAE disease via inducing IL-10 production (Niedbala et al., 2007). To investigate a participation of GSNO inducible CD4+CD25+ FOXP3− Treg in immuno-modulation of EAE animals, CD4+CD25+ FOXP3− Treg cells induced in ex vivo by treatment with GSNO were transferred to active EAE mice on the day of disease onset (day 14 post-immunization). FIG. 10A show that transfer of GSNO-inducible CD4+CD25+ FOXP3− Treg cells significantly attenuated clinical signs of EAE disease. As expected. EAE mice treated with GSNO inducible CD4+CD25+ FOXP3− Treg cells, as compared to untreated EAE mice, expressed higher levels of IL-10, lower levels of IL-17, and comparable levels of IFN-γ in spinal cords (FIG. 10), CD4+CD25+ FOXP3− Treg is one of effector CD4+ T cells involved in GSNO-mediated anti-inflammation under EAE conditions. Taken together, these data suggest GSNO as a potential inducer of CD4+CD25+ FOXP3-Treg mediated anti-inflammatory responses and an inhibitor for TH17 mediated pro-inflammatory responses in EAE. GSNO is a thiol based NO carrier molecule but it does not release free NO molecule efficiently (He et al., 2016). Rather, it exerts its biological effect via modification of protein thiols, a process termed S-nitrosylation (Gaston et al., 2003). Cellular levels of GSNO is regulated not only by its synthesis but also by its degradation mediated by enzyme GSNOR (Gaston et al., 2003).

N6022 is a first-in-class compound that is a very potent, specific, and reversible inhibitor of GSNOR. In this study, it was observed that GSNO modulated polarization and expansion of CD4+ T cells (TH17 and Treg) in the spleen of EAE animals, thus it was next assessed the effect of exogenous GSNO treatment and induction of endogenous GSNO accumulation by N6022 treatment on the levels of protein associated S-nitrosothiols in spleens of EAE animals. It was observed that induction of EAE disease had no obvious effect on the levels of protein associated S-nitrosothiols in the spleens. As expected, treatment of EAE mice with GSNO increased spleen levels of protein-associated S-nitrosothiols as compared to control and EAE mice. In addition, treatment of EAE mice with N6022 also increased spleen levels of protein-associated S-nitrosothiols to the levels comparable to GSNO treated EAE mice. These data indicate that both GSNO and N6022 are seemingly effective in induction of protein S-nitrosylation in spleen cells under EAE disease condition.

Figure 13:
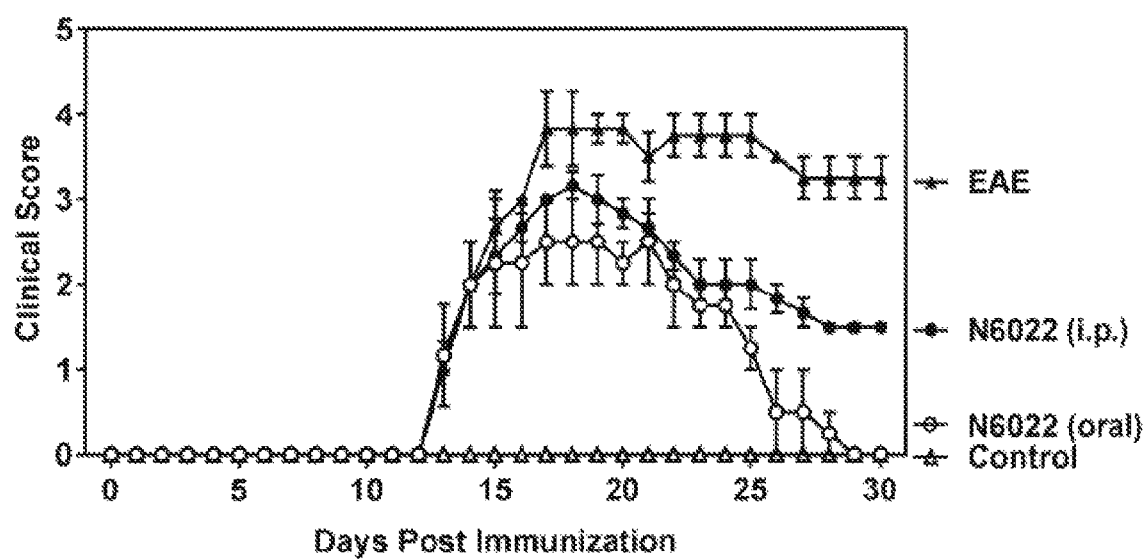
FIG. 13: A comparison of drug efficacy of N6022 (1 mg/kg/day) with different dosing routes (intraperitoneal treatment vs. oral treatment) in EAE mice.

GSNOR Inhibitor (N6022) Attenuates EAE Disease:

Although exogenous GSNO treatment showed significant improvement in EAE disease, GSNO has some disadvantages in clinical use, GSNO is a photolabile compound, and like other S-nitrosothiol compounds and has a short half-life in aqueous solution (Ramsay et al., 1995). Secondly, the distribution and clearance of GSNO are largely affected by cellular/tissue expression of GSNOR (Liu et al., 2004; Benhar et al., 2009). Thirdly. GSNO causes a feed-forward induction of GSNOR activity (Brown-Steinke et al., 2010) and thus chronic GSNO treatment could cause a GSNO resistance. It was observed that inhibition of GSNOR by treatment with N6022 efficiently increased the levels of S—NO proteins in EAE mice. Therefore, the efficacy of N6022 on EAE disease was evaluated. It was observed that N6022 (1 mg/kg/day/i.p.) treatment of EAE mice significantly decreased EAE disease severity as shown by their clinical score [untreated EAE mice: 3.5±0.5, N6022 treated EAE mice: 2.67±0.29 at the peak of disease (day 21 of post immunization); untreated EAE mice: 2.5±0.5, GSNO treated EAE mice: 0.3±0.29 at the remission of disease (day 41 of post immunization)]. In this experiment the efficacy of the same dose of FTY720 was evaluated (1 mg/kr/day/oral) as a positive drug control. Treatment of EAE mice with FTY720 also attenuated the progression of EAE disease (clinical score 3.0±0.87 at the peak of disease and 1.67±0.58 at the remission of disease) but was less effective as compared to the same dose of N6022 treatment. The efficacy of oral treatment with N6022 (1 mg/kg/day) was evaluated on EAE disease. Interestingly, it was observed that N6022 showed greater efficacy with oral route treatment than i.p. route treatment (FIG. 13).

Next, myelin status was assessed in the spinal cords of EAE mice treated with saline, N6022, or FTY720. The data of immunofluorescent staining of spinal cord sections for M8P and Western analysis for M8P and PLP indicate that N6022 treatment protects against the myelin loss in the spinal cords of EAE mice greater than FTY720 treatment. These data indicate a therapeutic potential of N6022 for attenuation of clinical disease as well as neurological disease of EAE.

Figures 11A, 11B, 11C:
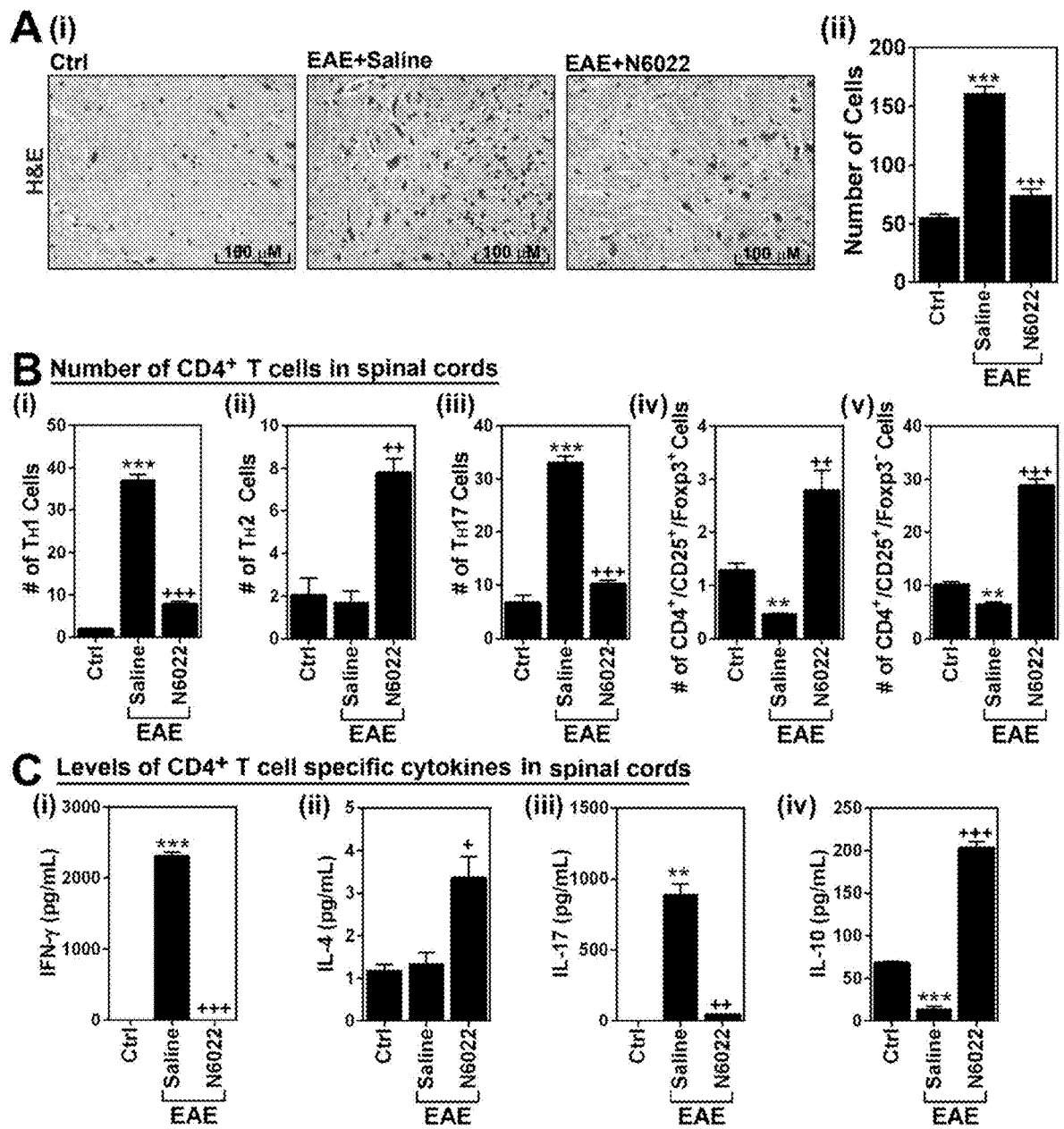
FIGS. 11A-11C: N6022 reduced CNS infiltration of peripheral mononuclear cells. A. At the peak of disease (day 20), spinal cord infiltration of mononuclear cells was analyzed by histological staining of spinal cord section by H&E method (i). The number of infiltrated cells in the H&E staining was manually counted and represented as number of cells per microscopic field (n=4). (ii). B. Next, total lymphocytes were isolated from spinal cords of control (ctrl), EAE mice, and EAE mice treated with N6022 and cultured under ex vivo conditions. Following the activation with MOG peptide, the number of CD4+ cell subsets, such as IFN-γ+TH1 (i), IL-4+TH2 (ii), IL-17+TH17 (iii), CD25+ FOXP3+ cells (iv), and CD25+ FOXP3- cells (v) were analyzed by fluorescence flow-cytometry analysis (n=4). C. From the culture media, the levels of CD4+ T cell subset specific cytokines, such as IFN-γ (i), IL-4 (ii). IL-17 (iii), and IL-10 (iv), were analyzed by ELISA (n=4). The graphs show mean±standard error of the mean (SEM):  $p<0.001$, * $p<0.0001$, compared to control (Ctrl) group; + $p<0.05$, ++ $p<0.001$, +++ $p<0.0001$ compared to EAE group.

N6022 Reduced CNS Infiltration of Peripheral Proinflammatory Immune Cells:

Next spinal cord infiltration of peripheral mononuclear cells was analyzed by H&E staining. FIGS. 11A and 11B show that treatment of EAE mice with N6022 significantly reduced the number of infiltration of mononuclear cells in the spinal cord. To assess the effect of N6022 treatment on the infiltration of each subset of CD4+ T cells into the spinal cords in EAE animals, fluorescence flow-cytometry analysis was performed for CD4+ IFN-γ+(TH1), CD4+IL-4+(TH2), CD4+IL-17+(TH17), CD4+CD25+ FOXP3+ Treg, and CD4+CD25+ FOXP3− Treg cells. FIGS. 11B-i and -iii show that N6022 treatment reduced EAE-induced spinal cord infiltration of TH1 and TH17 cells. Accordingly, N6022 treatment decreased effector functions of TH1 and TH17 cells in the CNS of EAE animals as shown by decreased levels of IFN-γ and IL-17 in the culture media of CNS derived lymphocytes (FIGS. 11C-i and iii). EAE mice had no obvious alteration in the number of TH2 cells in the CNS as compared to control mice but N6022 treatment increased the number of TH2 cells (FIG. 11B-ii) as well as their effector function (IL-4 release in FIG. 11C-ii) in EAE mice. EAE mice showed a reduction in numbers of $CD4^+$ $CD25^+$ $FOXP3^+$ Treg cells and $CD4^+$ $CD25^+$ $FOXP3^-$ Treg cells in the CNS (FIG. 11B-iv and v) as well as reduction in their expression of IL-10 (FIG. 11B-iv). However, treatment of the mice with N6022 increased the numbers of both Treg cells as well as their expression of IL-10 over the control levels. These data indicate that N6022 treatment of EAE mice inhibits infiltration and effector function of proinflammatory subsets of CD4+ T cells (TH1 and TH17) while restoring/inducing the infiltration and effector function of anti-inflammatory subsets of $CD4^+$ T cells (TH2 and Tregs).

Figure 12A:
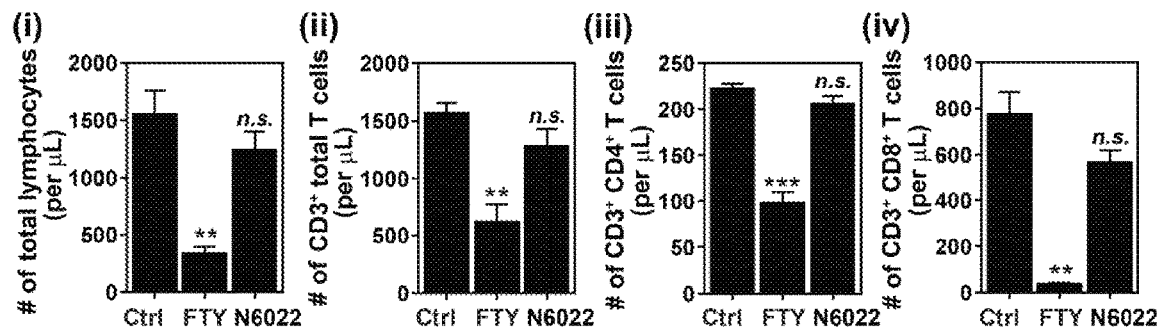
FIGS. 12A-C: N6022 treatment differentially modulates subset specific polarization of CD4+ T cells in spleen without exhibiting lymphopenia-related effect. A. Normal mice (without EAE) were treated with saline (Ctrl), GSNO or FTY720 (FTY) for 19 days and the numbers of total lymphocytes (i), CD3+ T cells (ii), CD4+ T cells (iii), and CD8+ cells (iv) in bloods were analyzed. B. At the peak of EAE disease, CD4+ T cells were isolated from the spleens of EAE mice treated with saline (EAE) or GSNO, re-stimulated with MOG peptide, and number of lineage specific CD4+ T cells, such as TH1 (i), TH17 (ii), total Treg (iii), CD25+ FOXP3+(iv), and CD25+ FOXP3-(v), were counted by fluorescence flow-cytometry analysis. C. From the culture media, the levels of CD4+ T cell subset specific cytokines, such as IFN-γ (i), IL-4 (ii), IL-17 (iii), and IL-10 (iv), were analyzed by ELISA The graphs show mean±standard error of the mean (SEM): * $p<0.05$,  $p<0.001$, * $p<0.0001$, compared to control (Ctrl) group; +$p<0.05$, ++$p<0.001$, +++$p<0.0001$ compared to EAE group; n.s.=not significant.

N6022 Treatment Differentially Modulates Subset Specific Polarization of CD4+ T Cells in Spleen without Exhibiting Lymphopenia-Related Effect:

Exogenous GSNO treatment attenuated EAE disease without affecting the numbers of circulating lymphocytes (FIG. 9). Accordingly, N6022 treatment also inhibited EAE disease but it did not affect numbers of circulating total lymphocytes (FIG. 12A-i) as well as CD3+ total T lymphocytes (FIG. 12Aii). CD3+; CD4+ TH cells (FIG. 12A-iii), and CD3+; CD8+ cytotoxic T cells (FIG. 12A-iv), which play pivotal role in normal immune surveillance. These data indicate that N6022 treatment and thus increased endogenous GSNO levels selectively inhibited infiltration and effector function of TH1 and TH17 in the CNS (FIG. 11) without causing any obvious lymphopenic effect which was observed in FTY720 treated mice (FIG. 9A).

Figure 12B:
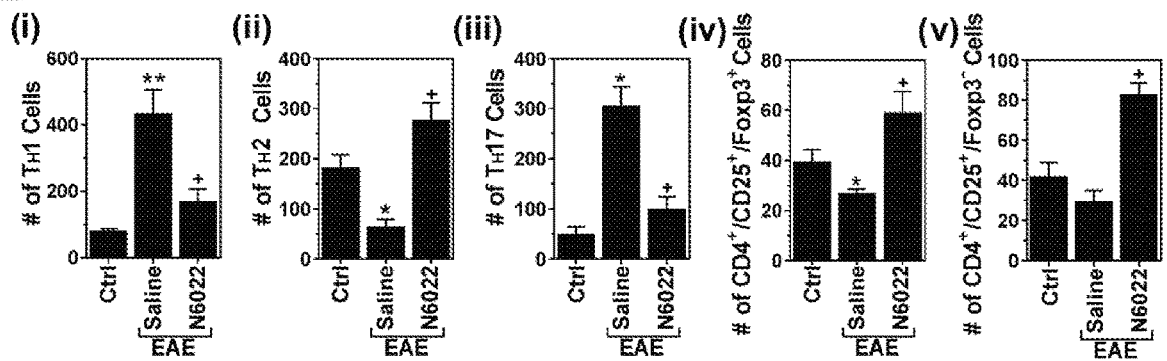
Figure 12C:
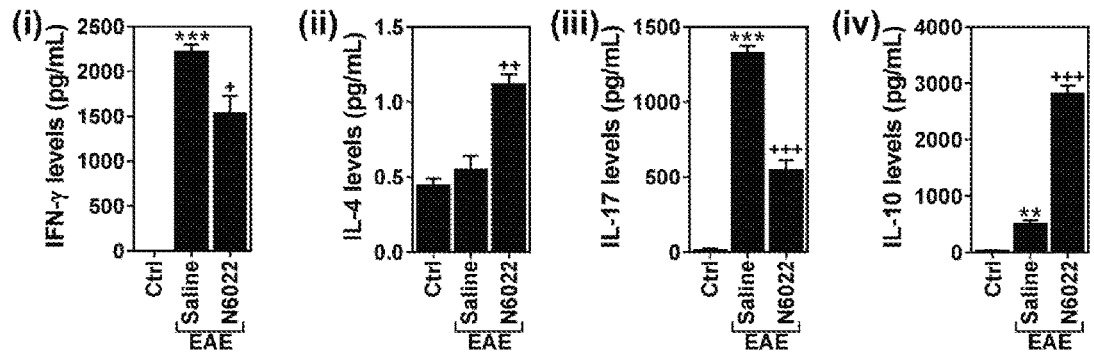

Next, the effects of N6022 were examined on the polarization/expansion of CD4+ T cells in the spleens of EAE mice. In accordance with the patterns of spinal cord infiltration (FIG. 11), N6022 treatments reduced EAE-induced polarization/expansion of spleen derived TH1 and TH17 cells in response to ex vivo MOG restimulation (FIG. 12B-i and -iii). Accordingly, N6022 treatment decreased the production of IFN-γ and IL-17 from these cells (FIG. 12C-i and -iii). In addition, N6022 treatment fully restored EAE-induced decrease in TH2 polarization/expansion (FIG. 12B-ii) as well as their IL-4 production (FIG. 12C-ii) to the control levels. Treatment of EAE mice with N6022 restored decreased polarization/expansion of CD4+CD25+ FOXP3+ Treg cells to the control levels (FIG. 12B-iv) and increased polarization/expansion of CD4+ CD25+ FOXP3− Treg cells over the control levels (FIG. 12B-iv). Accordingly. N6022 treatment enhanced IL-10 production from these cells (FIG. 12C-iv). These data document that N6022 treatment attenuates the CNS infiltration and effector function of the proinflammatory TH1 and TH17 cells but elevates the anti-inflammatory TH2 and Treg cells via modulation of their polarization in the spleen without producing any obvious lymphopenic effect which was observed in GSNOR knockout mice (Yang et al., 2010). Overall, the above studies document that treatment of EAE animals with inhibitor of GSNOR down regulate proinflammatory T cell response while upregulating the anti-inflammatory T cell responses as well as protection against the CNS disease of EAE.

In summary, this study describes the therapeutic advantage of GSNO-mediated mechanism for treatment of autoimmune disease of EAE and MS Previously, it was reported that GSNO treatment selectively modulates TH17, but not TH1 and TH2, mediated pro-inflammatory responses in EAE models (Nath et al., 2010). Here, the effect of N6022, a reversible GSNOR inhibitor with clinically proven safety, was evaluated on EAE disease and compared its efficacy with exogenous GSNO and FTY720, a nonspecific immune-suppressor. A single dose comparison of effects of N6022, GSNO, and FTY720 (1 mg/kg/day) on progressive EAE disease showed that N6022 was the most potent in inhibition of EAE disease. At the same doses, both N6022 and GSNO treatments increased comparable levels of protein-associated S-nitrosothiols in spleen, which reflect the tissue levels of GSNO, and seemingly inhibited TH17 and induced $CD4^+$ $CD25^+$ $FOXP3^-$ Treg. However, N6022 further inhibited TH1 and induced TH2 and $CD4^+$ $CD25'/FOXP3'$ Treg. N6022 may have different pharmacokinetics, pharmacodynamics, and cell-type specific activity in induction of cellular GSNO accumulation as compared to exogenous GSNO treatments. Therefore, exogenous GSNO and N6022 are expected to have different efficacies on EAE/MS disease, as observed in this study N6022 treatment did not caused any obvious lymphopenic effects as seen in FTY720 treatment, but exhibited superior efficacy on EAE disease at the same doses. Overall, the data in this study suggest that N6022 as a novel drug for MS/EAE that selectively downregulates proinflammatory subsets of CD4+ cells (TH1 and TH17) and upregulates anti-inflammatory subsets of $CD4^+$ cells (TH2 and Tregs).

Example 4—Materials and Methods

Induction of Active EAE and Drug Treatments:

Female C57BL/6 mice of 8-12 weeks of age, purchased from Jackson Laboratory, were provided with food and water ad libitum and were kept in pathogen free animal care facility of Medical University of South Carolina (MUSC) throughout the study. All procedures were conducted in accordance with accepted standards of humane care as approved by the Institutional Animal Care and Use Committee (Approved number: AR #1644). EAE was induced as described previously (Nath et al., 2009). Briefly, mice were immunized subcutaneously in the flank regions with $MOG_{35-55}$ peptide (MOG; 200 µg; Peptide International) emulsified (1:1) in 100 ul complete Freund's adjuvant (CFA) on day 0 and day 7. Additionally, 300 ng of Pertussis toxin (Sigma-Aldrich, St. Louis, Mo.) was given on day 0 and day 2 by i.p. injection. Pertussis toxin used as per the standardized protocol reported by us and other investigators for the induction of EAE (Nath et al., 2009). Similarly, healthy control group received subcutaneous injection of PBS and CFA emulsion on day 0 and day 7. Clinical signs of EAE were scored by examiners blinded to experimental treatments using the following scale: 0=no clinical signs of disease; 1=piloerection and sluggish; 2=limp tail (ataxia); 2.5=ataxia with partial hind limb paralysis; 3=full paralysis of hind limb; 3.5=full paralysis of hind limb with paralysis of one fore limb; 4=full paralysis of two limbs; 4.5=moribund stage; 5=death. After the onset of the disease (with clinical score between 1 and 2), the animals were given daily treatment with GSNO (1 mg/kg body weight oral), N6022 (1 mg/kg body weight i.p.; Axon Medchem, Reston, Va.), or FTY720 (1 mg/kg body weight; Cayman Chemical, Ann Arbor, Mich.). The drug treatments were continued till the termination of the study (day 41 post immunization). EAE animals without drug treatment received PBS. Likewise, healthy controls received vehicle.

Adoptive Transfer of GSNO-Inducible MOG Specific Treg Cells to Active EAE Mice:

At the peak of EAE disease, the mice were sacrificed and CD4+ T cells were purified from spleens by CD4+ T cell isolation kit (Miltenyi Biotec, Auburn, Calif.). The purified T cells ($2.5 \times 10^6$ cells/ml) were cultured in 96-well round-bottom microculture plates (Falcon Labware. Oxnard, Calif.) in 'complete RPMI-media' containing RPMI 1640 (Life Technologies, Gaithersburg, Md.), 10% FBS, (GE Healthcare Bio-Sciences, Pittsburgh, Pa. USA) and 100 µg/ml streptomycin and penicillin (Atlanta Biologicals Norcross, Ga.), 1 mM glutamine, 1 mM nonessential amino acids, and 50 µM 2-mercaptoethanol (Sigma-Aldrich, St. Louis, Mo.). For expansion of $CD4^+/CD25^+/FOXP3^-$ Treg cells, the cells were treated with 100 µM GSNO for 72 hours with refreshment every 24 hrs. Next, the cells ($20-30 \times 10^6$) collected in 300 µL of PBS were transferred to EAE mice at the day of disease onset.

Histological Analysis:

After remission of EAE disease (day 41 post immunization), control mice, EAE mice, and EAE mice treated with GSNO or N6022 were anesthetized and perfused first with saline and then 4% paraformaldehyde as described previously Nath et al., 2004. Tissue samples were embedded in paraffin block and sectioned transversely (5 µm-thick). Haemotoxylin and Eosin (H&E) staining was performed to assess infiltration of leukocyte and inflammation. For the quantitation of infiltrates, the digital images were analyzed by ImageJ (NIH, Bethesda, Md.). To assess the status of myelin, the sections were stained with antibody specific to myelin basic protein (MBP) and detected with immunofluorescent analysis. All digital images were taken using BX-60 microscope equipped with DP70 camera unit (Olympus, Tokyo, Japan).

Total Lymphocyte Count:

Normal female C57BL/6 mice were treated GSNO, N6022, or FTY720 for 19 days and then sacrificed for the collection of blood. The bloods collected in EDTA blood collection tubes (BD Biosciences) were analyzed by an automated hematology analyzer for counting total lymphocytes. For counting of each subset of lymphocytes, 50 µl of blood was mixed with staining buffer (20 µl) containing fluorescence labelled antibodies and red-blood-cells were lysed with FACS lysing solution (BD Biosciences) prior to fluorescence flow-cytometric analysis. For staining of CD3+, CD4+, and CD8+ cells, allophycocvanin (APC)-labeled anti-mouse CD3 (eBioscience clone 17A2), Fluorescein isothiocyanate (FITC)-labeled anti-mouse CD4 (eBioscience clone RM4-5), APC-labeled anti-mouse CD8 (eBioscience clone 53-6.7) and appropriate isotype matched controls.

Fluorescence Flow Cytometry Analysis of TH1, TH2, TH17, and Treg Cells in Spinal Cords and Spleens:

Fluorescence flow cytometry analysis for each subset of CD4+ T cells (TH1, TH2, TH17, CD4+CD25+ FOXP3+ Treg, and CD4+CD25+ FOXP3− Treg) were performed based on our previous report with modification (Nath et al., 2004). Briefly, control mice, EAE mice. EAE mice treated with GSNO. N6022, or FTY720 at the peak of disease (day 16 to day 19 post-immunization) were sacrificed for the collection of spinal cords and spleens. Following the preparation of single cell suspension, red blood cells were lysed with Pharma lyse buffer (BD Pharmingen™) and the remaining spleen cells were washed with RPMI 1640. The isolated CD4+ T cells were then resuspended with complete RPMI-media in 12-well plates (5×10⁶ cells' 2 ml per well) containing MOG peptide (25 µg/ml) for 48 hrs. Following the centrifugation, the resulted supernatants were collected for ELISA for CD4+ subset specific cytokines (see below). The cell pellets were washed with cell staining solution (ebioscience, Waltham, Mass. USA) and stained with fluorescence labeled antibody specific to IFN-γ for TH1. IL-4 for TH2, IL-17 for TH17, CD25+ for total Treg. CD25+ and FOXP3+ for FOXP3+ Treg, and CD25+ and FOXP3− for FOXP3-Tregs (ebioscience, Waltham, Mass., USA). The cells were counted and analyzed using Beackman Coulter instrument (Beckman Coulter, Inc., Brea, Calif., USA).

ELISA for Subset Specific CD4+ T Cell Cytokines in the Spinal Cords:

ELISA assay was performed for analysis of CD4+ T cell subset specific cytokines released from cultured cells or spinal cord tissues. For extraction of spinal cord lysates, the spinal cords isolated from animals at the peak of the EAE disease were homogenized in PBS containing complete protease inhibitor mixture (Roche Diagnostics, Mannheim, Germany). Following the centrifugation (10,000×g), the levels of protein in the supernatant were estimated by Lowry assay using DC protein assay kit (Bio-Rad, Hercules, Calif.). The equal amounts of proteins were analyzed for ELISA for IFN-γ. IL-4, IL-17, and IL-10. ELISA kits for IFN-γ, IL-17, and IL-10 were purchased from R&D systems (Minneapolis, Minn.) and ELISA kit for IL-4 were purchased from Biolegend (San Diego, Calif.).

Western Analysis:

After remission of EAE disease (day 41 post immunization), the spinal cord tissues were homogenized in 1×SOS-PAGE sample buffer (5×: 0.25 M Tris-Cl (pH 6.8), 50% (v/v) Glycerol, 5% (w/v) SDS, 0.05% (w/v) bromophenol blue, 0.25 M DTT) by sonication. Following the centrifugation (10,000×g), the levels of protein in the supernatant were estimated by Lowiy assay using DC protein assay kit (Bio-Rad). The equal amounts of proteins were resolved in 4-20% gradient SDS-PAGE (BioRad) and transferred to nitrocellulose membranes. The membranes were then blocked with blocking buffer (5% nonfat dry milk, 20 mM Tris, 500 mM NaCl, and 0.1% Tween20, pH 7.6) and incubated in blocking buffer containing primary antibody specific to myelin basic protein (MBP; Santa Cruz Biotech, Delaware Avenue, Calif.), proteolipid protein (PLP; Santa Cruz Biotech), or D-actin (Cell Signaling, Danvaers, Mass.). Following washing, the membranes were incubated with 1:10,000 diluted horseradish peroxidase (HRP) conjugated secondary antibody (Jackson ImmunoResearch Lab, West Grove, Pa.), washed and then incubated with ECL reagent (Amersham Life Science, Pittsburgh, Pa.), and exposed to ECL film.

Analysis of Protein S-Nitrosylation and Nitrotyrosine Formation:

Protein S-Nitrosylation was detected using the biotin-switch method with slight modification as described in our previous study (Kim et al., 2014). Spleens were homogenized in 250 mM HEPES, pH 7.7, 1 mM EDTA, 0.1 mM neocuproine, 1% Nonidet P-40, 150 mM NaCl, 1 mM PMSF, 20 µM methyl methanethiosulfonate (MMTS), 80 µM carmustine, protease inhibitor mixture (Sigma), and mixed with an equal volume of 25 mM HEPES. pH 7.7.0.1 mM EDTA, 10 µM neocuproine, 5% SOS, 20 µM MMTS and incubated at 50° C. for 20 min. After acetone precipitation, the precipitates were resuspended in 25 mM HEPES, pH 7.7, 1 mM EDTA, 10 µM neocuproine, 1% SOS and mixed with two volumes of 20 mM HEPES. pH 7.7, 1 mM EDTA, 100 mM NaCl, 0.5% Triton X-100. The S-nitrosylated proteins were then modified with biotin in 25 mM HEPES, pH 7.7, 0.1 mM EDTA, 1% SOS, 10 µM neocuproine, 10 mM ascorbate sodium salt, and 0.2 mM N-[6-(biotinamido)hexyl]-3'-(2'-pyridyldithio) propionamide (biotin-HPDP, Pierce). After acetone precipitation, biotinylated proteins were resolved by SOS-PAGE and visualized by Western analysis using antibody specific to biotin (Cell Signaling).

Statistical Analysis:

Clinical disease scores as average maximal scores over the treatment period (mean±SD) and analyzed using Kruskal-Wallis test. Statistics for proliferation and cytokine responses were analyzed with one-way multiple-range analysis of variance using Graph Pad Prism 3.0 software. Significances (p value) between groups were determined using the Newman-Keul test. A value of $p<0.05$* and above was considered significant.

Example 5—GSNO in EAE Model

Previously, it was reported that prophylactic and therapeutic efficacy of GSNO in progressive and relapsing-remitting models of active EAE (Nath et al., 2010). In both models, GSNO was reported to attenuate the EAE disease by inhibiting STAT3/RORγt and thus TH17 specific immune responses, but without altering TH1 (STAT4/T-bet) and TH2 (STAT6/GATA3) specific immune responses. Moreover, in ex vivo and in vitro T cell culture studies. GSNO treatment specifically inhibited IL-6 and TGF-β induced polarization and expansion of TH17 cells and their effector function (IL-17 production) induced by IL-23 (Nath et al., 2010) suggesting a role for GSNO mediated mechanisms in modulation of differentiation, expansion, and effector functions of TH17 cells.

Figures 14A, 14B, 14C:
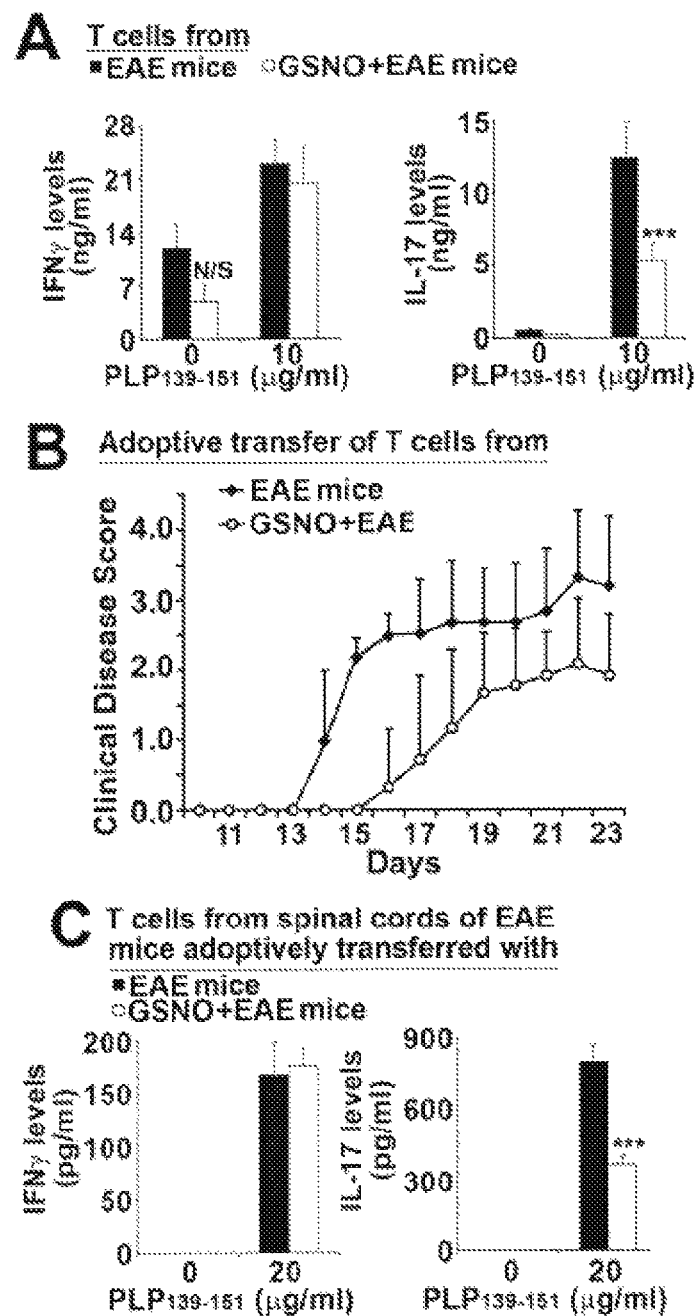
FIGS. 14A-14C: Effect of adoptive transfer of T cells isolated from EAE or GSNO treated EAE mice in development of passive EAE disease. PLP139-151 specific T cells isolated from spleens and lymph-nodes of EAE mice or GSNO treated EAE mice were cultured ex vivo and re-stimulated with PLP139-151 (10 µg/ml) under THO condition (IL-2). (A) For characterization of TH1 vs. TH17 differentiation, the media from cultured CD4+ cells from GSNO treated and untreated EAE mice were analyzed for IFN-γ or IL-17. (B) The cultured T cells stimulated with PLP139-151 were adoptively transferred to the naive host SJL mice and the development of passive EAE disease was monitored daily by blinded investigators. (C) At the peak of EAE disease, T cells were isolated from the spinal cord and release of IFN-γ and IL-17 were analyzed by ELISA in the presence or absence of ex vivo PLP139-151 stimulation.

In the present study, further evidence is provided supporting the role of GSNO in inhibition of TH17 cell differentiation and effector function by using murine passive-immunization model of EAE. PLP139-151 peptide-induced EAE model in SJL mice is a well-suited tool to experimentally address mechanisms that cause the remitting-relapsing autoimmune pathology of MS patients. Using this model, the regulatory role of GSNO was investigated in differentiation and effector functions of T cells associated with EAE disease. SJL mice were immunized with PLP139-151 peptide and treated with 1.0 mg/kg GSNO (denoted as "GSNO+ EAE group" hereafter) or the same volume of PBS (denoted as "EAE group" hereafter) daily starting on the day of immunization. At the peak of EAE disease (−day 10 post immunization), CD4+ T cells were isolated from the draining lymph nodes and spleens of the mice in both groups (EAE and GSNO+ EAE). The isolated T cells w ere cultured in ex vivo in the presence or absence of PLP139-151 peptide, then, lineage specific activation of T cells (TH17 vs. TH1) was analyzed by media levels of TH1 (IFN-γ) and TH17 (IL-17) cytokines FIG. 14A shows that T cells isolated from the EAE group or GSNO+ EAE group produced comparable levels of IFN-γ in response to PLP139-151 stimulation. However, T cells isolated from GSNO+ EAE group produced significantly lower levels of IL-17 as compared to those from T cells isolated from the EAE group.

To evaluate the role of GSNO-mediated mechanisms in immune responses of EAE, ex vivo cultured T cells were re-stimulated with PLP139-151 peptide and then adoptively transferred to naive SJL mice as passive immunization. Development of EAE disease was assessed by daily evaluation of mean clinical score. FIG. 14B show that the mice passively immunized with T cells from GSNO+ EAE group exhibited significantly delayed and milder disease than the mice passively immunized with T cells from EAE group. Next. TH17 vs TH1 lineage specific expressions of IL-17 vs. IFN-γ were investigated in spinal cords of the passively immunized EAE mice. FIG. 14C shows that the mice passively immunized with T cells from EAE group and GSNO+ EAE group expressed comparable levels of IFN-γ in the spinal cords. However, the mice passively immunized with T cells from GSNO+ EAE group expressed significantly lower levels of IL-17 than the mice passively immunized with T cells from EAE group (FIG. 14C). These data, along with the data from actively-immunized EAE model (21), indicate that GSNO attenuates EAE disease via modulation of TH17 differentiation without altering the TH1 lineage cell function (IFN-γ).

Figures 15A, 15B:
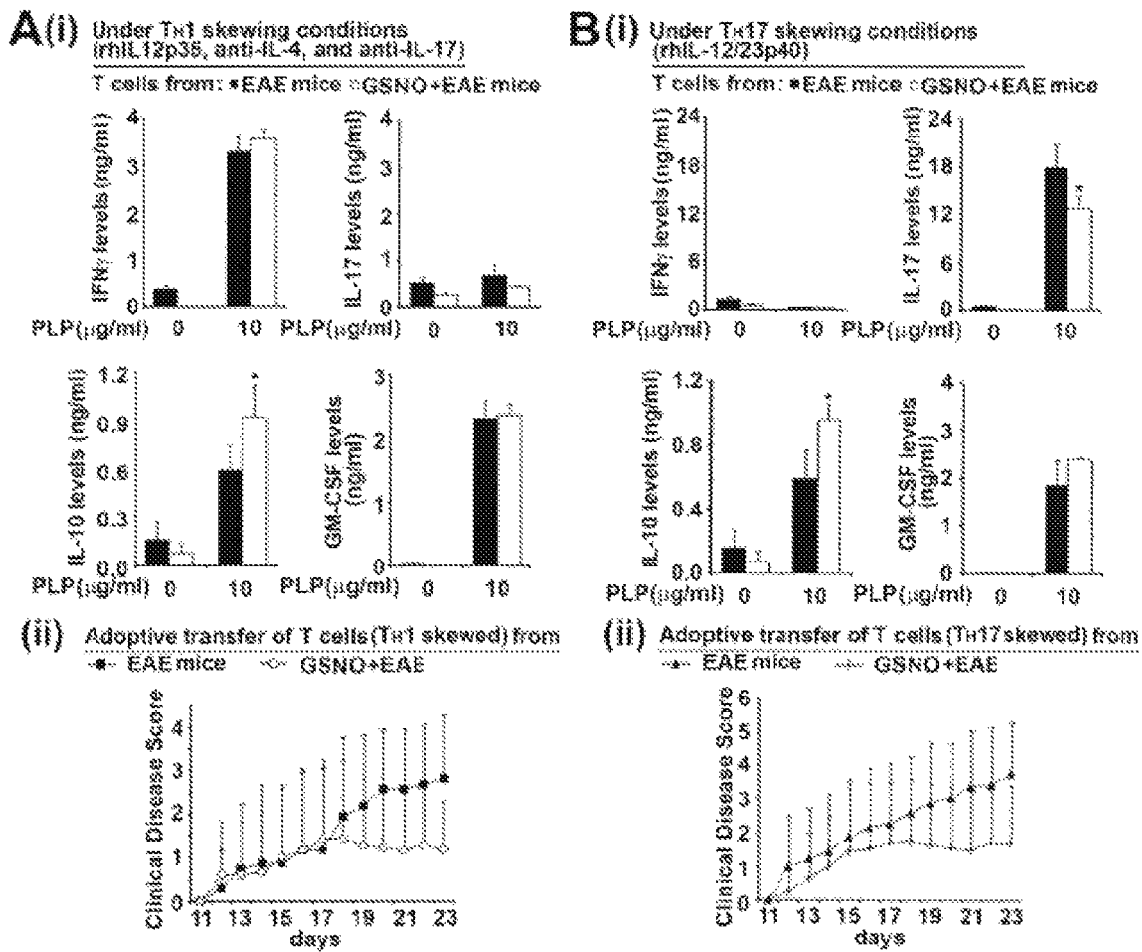
FIGS. 15A-15B: Development of passive EAE disease by adoptive transfer of TH1 or TH17 skewed T cells isolated from GSNO treated or untreated EAE mice T cells isolated from spleens and lymph nodes of GSNO treated or untreated EAE mice were cultured under TH1 (IL 12p35, anti-IL-4, and anti-IL-17) (A) or TH17 (IL 12/23p40) (B) skewing conditions in the presence or absence of PLP139-151 peptide. Then, release of IFN-γ, IL-17, IL-10, and GM-CSF were analyzed by ELISA (A-i and B-i). TH1 and TH17 skewed T cells were then adoptively transferred to naive host mice to induce passive EAE disease and clinical disease scores were analyzed daily as described experimental procedure (A-ii and B-ii).

To further evaluate the role of GSNO in lineage specific inhibition of TH1 vs. TH17 differentiation during the immunization, T cells isolated from EAE or GSNO+ EAE group of mice were skewed under TH1 (IL-2, rhIL-12p35, and anti-IL-4) or TH17 (IL-2, rhIL-12/23p40, anti-IFN-γ, and anti-IL-4) cytokine conditions for lineage specific expansion in the presence or absence of PLP139-151 peptide. FIG. 15A-1 shows that T cells isolated from mice of EAE and GSNO+ EAE groups produced comparable amounts of IFN-γ, but not IL-17 under TH1 skewing conditions. On the other hand, T cells isolated from EAE group produced higher levels of IL-17 than T cells isolated from GSNO+ EAE group under TH17 skewing conditions, while T cells from both groups did not produce any IFN-γ under the same TH17 skewing conditions (FIG. 15B-i). T cells isolated from both EAE and GSNO+ EAE groups produced similarly increased levels of GM-CSF, a non-lineage specific cytokine, under both TH1 and TH17 skewing conditions (FIGS. 15A-i and B-i). Again, these data indicate a lineage specific inhibitory action of GSNO on TH17 differentiation during the development of EAE disease. Interestingly. T cells isolated from GSNO+ EAE group produced significantly higher amounts of IL-10 than the T cells isolated from EAE group under both TH1 and TH17 skewing conditions (FIGS. 15A-i and B-i). Accordingly, adoptive transfer of both TH1 and TH17 skewed T cells from GSNO treated EAE mice expressing high levels of IL-10, as compared to T cells from untreated EAE mice, produced significantly milder EAE disease (FIGS. 15A-ii and 15B-ii). IL-10 is an anti-inflammatory cytokine and its potential on the attenuation of EAE disease was shown in transgenic mice expressing IL-10 in T cells (Bettelli et al, 1998). Therefore, this study, for the first time, reports the role of GSNO-mediated mechanisms in induction of IL-10 expression under both TH1 and TH17 skewing conditions and its potential participation in attenuation of EAE disease. IL-10 is known to inhibit immune responses mediated by both TH1 and TH17 cells (Florentino et al., 1991; Huber et al., 2011). Therefore, GSNO-induced IL-10 production under TH1 and TH17 skewing conditions should inhibit effector functions of both TH1 and TH17 cells. However, GSNO inhibited only TH17 pathway without affecting TH1 pathway (FIGS. 15A-i and B-i) and the underlying mechanism for GSNO mediated selective inhibition of TH17 is not well understood at present.

NO induced IL-10 production via induction of specific lineage of regulatory T (Treg) cells was described previously (Niedbala et al., 2007). These cells expressed cell surface markers for Treg (e g. CD4 and CD25) but not FOXP3 and thus are distinguished from neutral and inducible Tregs (nTreg and iTreg; CD4+/CD25+/FOXP3+). In addition, these cells were IL-10-independent m their induction and thus distinguished from TH1 (CD4+/CD25+/FOXP3−) (22).

Figures 16A, 16B:
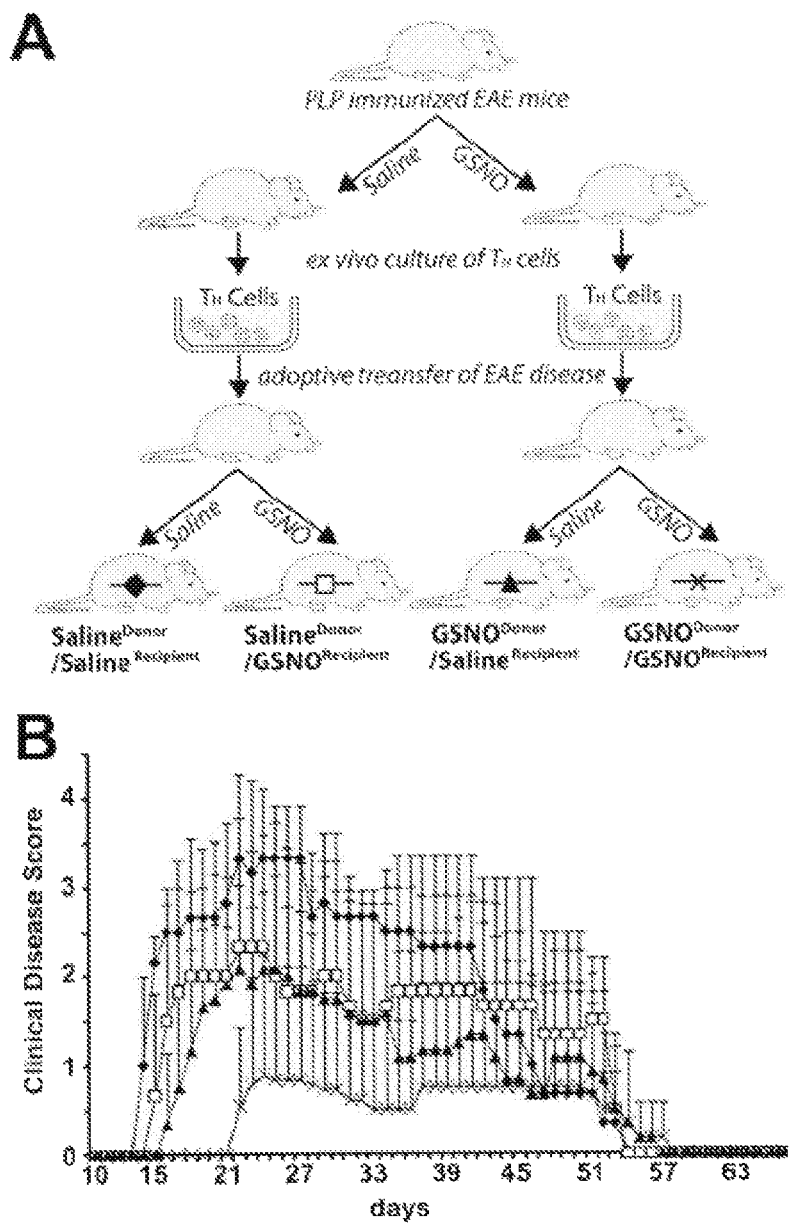
FIGS. 16A-16B: Effect of GSNO treatment in T cell differentiation and effector function in adoptive transfer EAE disease. The PLP-immunized T cells from spleens and lymph-nodes of EAE mice or GSNO treated EAE mice were transferred to naive SJL mice. On the day of passive immunization, the recipient mice were further treated vehicle (saline) or GSNO during the course of the disease (A). Following immunization, the severity of EAE disease was analyzed as described in materials and methods (B). Each group denotes saline treated recipient mice immunized with T cells from saline treated EAE mice (line with sold diamonds), GSNO treated recipient mice immunized with T cells from saline treated EAE mice (line with open squares), saline treated recipient mice immunized with T cells from GSNO treated EAE mice (line with solid triangles), or GSNO treated recipient mice immunized with T cells from GSNO treated EAE mice (line with cross marks).

These NO-inducible CD4+CD25+ FOXP3− cells, coined as 'NO-Treg', had a potent immunomodulatory effect by producing anti-inflammatory IL-10 in the active EAE mouse model (22). According to this report, GSNO-mediated mechanisms may contribute to inhibition of TH17 immune response and EAE disease via inducing NO-Treg (Niedbala et al., 2007). However, the observed induction of high levels of IL-10 by T cells from GSNO treated EAE mice under both TH1 and TH17 skewing conditions (FIGS. 15A-i and B-i) also indicate the role of TH1/TH17 cell produced IL-10 in immunomodulation of EAE. GSNO is known for its anti-inflammatory activity in various disease conditions (see Corti et al., 2014, for review). Under EAE conditions. GSNO was reported to inhibit CNS infiltration of peripheral immune cells via inhibiting endothelial expression of proinflammatory adhesion molecules (eg. ICAM and VCAM) (Prasad et al., 2007). At molecular levels, GSNO is known to inhibit activities of a series of transcription factors (eg. NF-KB, AP-1, GREB, and STAT3) via S-nitrosylation mechanisms (Corti et al., 2014; Prasad et al., 2007; Won et al., 2013). It is of interest to note that some of these transcription factors also play critical roles in IL-23 mediated TH17 effector function (e g STAT3) (Cho et al., 2008) as well as IL-17 mediated inflammatory reaction (e.g. NFKB and AP-1) (Song et al., 2013). Therefore, GSNO may exert its efficacy on EAE disease not only via regulating the T cell differentiation, but also via regulating effector functions of polarized T cells and thus neuroinflammation. To further investigate the efficacy of GSNO on the TH17 cell effector function in EAE disease, SJL naive mice were passively immunized by adoptive transfer of T cells isolated from EAE or GSNO+ EAE group and further received daily GSNO treatment during the course of the disease (FIG. 16A). FIG. 16B shows that passive immunized mice with the T cells isolated from GSNO treated EAE mice, but without receiving GSNO during the disease, exhibited milder disease (solid triangles) and the disease severity was further reduced when these mice were treated with GSNO during the disease (cross markers). On the other hand, passive immunized mice with T cells from untreated EAE mice exhibited the severest EAE disease (solid diamonds) and GSNO treatment of these mice during the disease also reduced the EAE disease (blank squares). These observations indicate that GSNO-mediated modulation of T cell differentiation as well as T cell effector function participate in attenuation of EAE disease. However, the mechanisms of GSNO induced IL-10 in EAE disease (FIGS. 15A and B) are not well understood at present.

The present study documents that GSNO selectively modulates TH17 cell differentiation during the development of EAE disease, but without altering the induction of other lineages of T cells (e.g. TH1 and TH2). In addition to the previous cell culture studies documenting the effect of GSNO in inhibition of TH17 expansion and effector function (Nath et al., 2010), this study also provides in vivo evidence that GSNO attenuates EAE disease by inhibiting effector function of T cells (e.g. T cells producing IL-17 and IL-10). This study, for the first time, reports the role of GSNO-mediated mechanism in induction of IL-10 expression under both TH1 and TH17 skewing conditions and its potential participation in attenuation of EAE disease. Overall, these studies document the prophylactic and therapeutic potential of GSNO for the treatment of autoimmune disease mediated by TH17 cells such as MS and rheumatoid arthritis.

Example 6—Materials and Methods

Mice: 7 Female SJL and C57BU6 mice, purchased from the Jackson Laboratory (Stock #000686; Bar Harbor, Me.), were housed in the animal care facility of Medical University of South Carolina and received standard laboratory food and water ad libitum. Paralyzed mice were provided with Transgel (Charles River Laboratories, Wilmington, Mass.) as an alternate food/water source. All animal protocols were in accordance with the animal experiment guidelines of the Medical University of South Carolina and National Institute of Health.

Induction of EAE Disease:

EAE disease was induced in 8- to 10-week-old female SJL mice by immunization with an emulsion (100 μl, subcutaneous) of proteolipid protein peptide (PLP139-151; Peptide International. Louisville, Ky.) and 200 μg of killed *Mycobacterium tuberculosis* H37Ra (Difco, Detroit, Mich., USA) followed by booster on day 7 as described previously (Nath et al., 2010). The mice additionally received pertussis toxin (Sigma-Aldrich, St. Louis, Mo.; 200 ng/300 μl PBS, intravenous) on day 0 and 3 post-immunization. On the day of immunization, one group of mice received 100 μl phosphate buffered saline (PBS) and the second group of mice received daily GSNO (1.0 mg/kg, 100 μl/PBS) via oral route GSNO was purchased from World Precision Instruments (Sarasota, Fla.) and its concentration was adjusted spectrophotometrically at 334 nm. Individual animals were observed daily for clinical disease severity by an investigator, blinded to experimental treatments, on a 0-5 scale as follows: 0=no abnormality; 1=piloerection, sluggish, 2=limp tail; 2.5=hind limb weakness (legs slip through cage top); 3=hind limb paralysis, 4=hind and forelimb paralysis; and 5=moribund.

Ex Vivo Culture of PIP 139-151 Immunized T Cells and Characterization of CD4+ T Cell Lineages:

At the peak of EAE disease, the mice were sacrificed and CD4+ T cells were purified from draining lymph nodes (DLN) and spleens by CD4+ T cell isolation kit (Miltenyi, Auburn. Calif.). The purified T cells ($2.5 \times 10_6$ cells/ml) were cultured in 96-well round-bottom microculture plates (Falcon Labware, Oxnard, Calif.) in RPMI-complete media containing RPMI 1640 (Life Technologies, Gaithersburg, Md.), 10% FBS, and 100 μg/ml streptomycin and penicillin (Atlanta Biologicals Norcross, Ga.), 1 mM glutamine, 1 mM nonessential amino acids, and 50 μM 2-mercaptoethanol (Sigma-Aldrich). For skewing of different CD4+ T cell subsets and their expansion, the isolated CD4+ T cells were stimulated with PLP139-151 (5 μg/ml) with IL-2 (10 ng/ml) for TH0, IL-2 (10 ng/ml), rhIL-12p35 (10 ng/ml), and anti-IL-4 (1 μg/ml) for TH1, or recombinant mouse IL-12/23p40 homodimer (10 ng/ml), anti-IFN-γ 1 (μg/ml), anti-IL-4 (1 μg/ml) for TO 17. All cytokines and antibodies were purchased from BD Biosciences (San Diego, Calif.). Following stimulation, the cells were harvested for adoptive transfer of EAE disease and the culture supernatants were collected for analysis of IFN-γ, IL-17, and IL-10 expression by ELISA (Biolegend Cat #430802, 432505, and 431411; San Diego, Calif.).

Adoptive Transfer Model of EAE Cultured T Cells ($20-30 \times 10^6$ T cells in 300 μl RPMI media per mouse) were injected to naive SJL female mice (8-10 week old) via intraperitoneal route. The recipient mice were also given two doses of pertussis toxin (200 ng/300 μl of PBS/i.p.) on day 0 and 2 of post immunization. Clinical EAE disease was measured as describe above.

Statistical Analysis

Clinical disease scores are presented as average maximal scores over the treatment period (mean+SD) and analyzed using a nonparametric Kruskal-Wallis test. Statistical significance was set at 0.05. Statistics for proliferation and cytokine responses were analyzed with a one-way multiple-range analysis of variance (ANOVA). All analyses were conducted using Graph Pad Prism 3.0 software. Significances (p-value) between groups were determined using the Newman-Keul test. A value of $p<0.05*$ and above was considered significant Example 7—Regulation of Endothelial Barrier Integrity by Redox-Dependent Nitric Oxide Signaling Thrombin Induced Cell Signaling for Endothelial F-Actin Stress Fiber Formation and Barrier Disruption in Cultured hBMVECs.

Figures 17A, 17B, 17C, 17D:
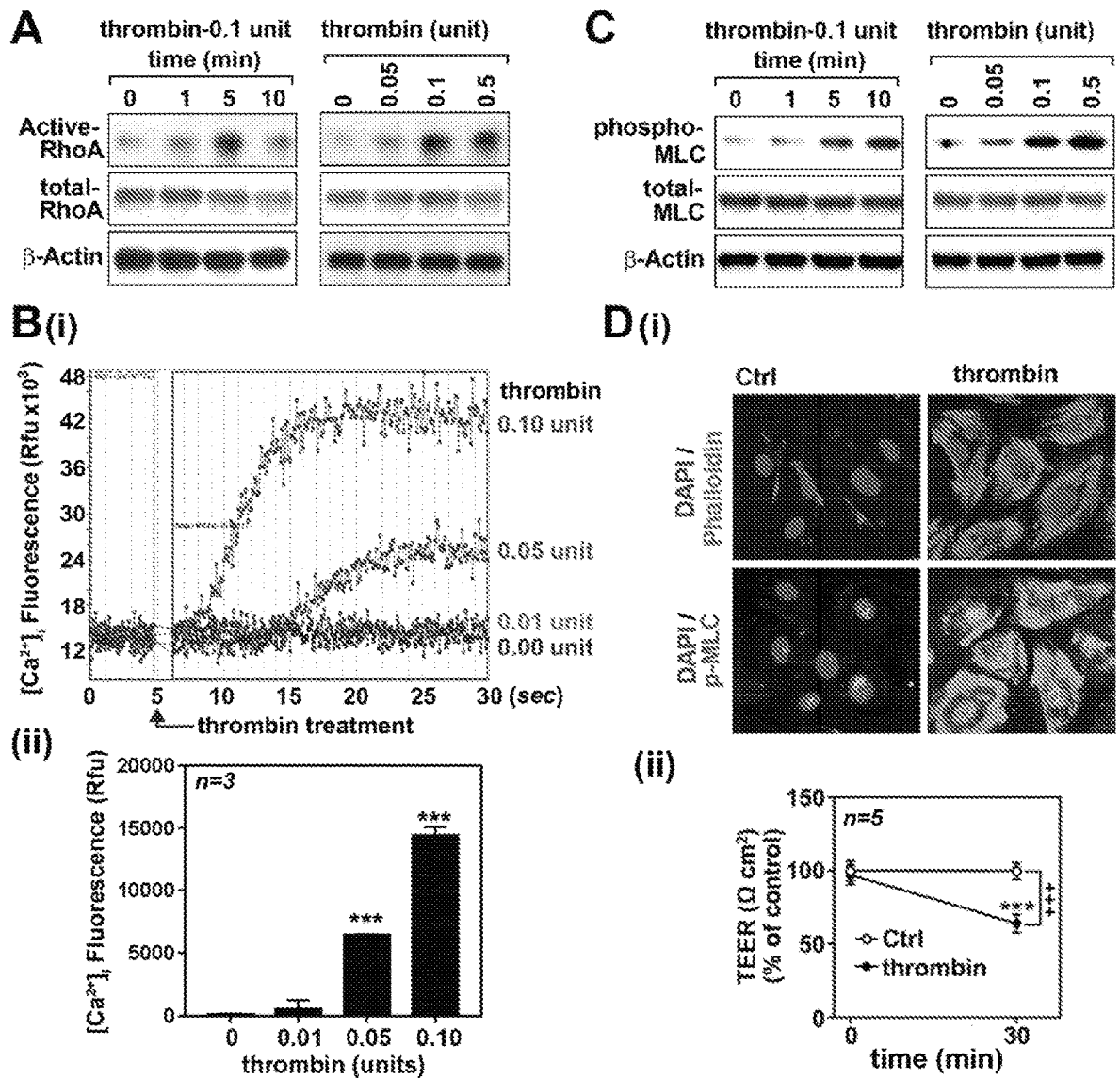
FIGS. 17A-17D: Thrombin induces cell signaling for endothelial barrier disruption in cultured hBMVECs. Human brain microvessel endothelial cells (hBMVECs) were treated with thrombin (0.1 unit/ml) and time dependent activation of RhoA activity was analyzed (left panel). The cells were also treated with various concentrations of thrombin and a dose dependent activation of RhoA activation was analyzed at 5 min following the treatment as described in method section (A). hBMVECs were treated with various concentrations of thrombin and intracellular $Ca^{2+}$ ($[Ca^{2+}]_i$) influx was analyzed by fluorometric assay as described in method section (B-i). Twenty five seconds following thrombin treatment, the increased $[Ca^{2+}]_i$ influxes were represented by bar graph (B-ii). In another set of experiment, thrombin time and concentration dependent phosphorylation of myosin light chain (Ser19) was analyzed in hBMVECs by Western analysis. β-actin was used for internal loading control for Western analysis (C). hBMVECs were treated with thrombin (0.1 unit/ml for 30 min) and development of F-actin stress fiber was analyzed by immunofluorescent staining of F-actin bundles by Phalloidin (red) and phosphorylated MLC (p-MLC; green). Nuclei were stained by DAPI (blue) (D-i). For endothelial barrier study, hBMVECs cultured on transwell plates were analyzed for transendothelial electric resistance (TEER) in the absence or presence of thrombin (0.1 unit/ml for 30 min) treatment (D-ii). The vertical bars (B-ii) and dots (D-ii) are means of individual data set (n=3) and T-bars are standard error mean. *** $p \leq 0.001$ as compared to control group. All experiments were repeated at least three times and representative data are shown.

RhoA/ROCK activation and $[Ca^{2+}]_i$ influx leading to MLC phosphorylation is a critical event in thrombin-induced F-actin stress fiber formation and actomyosin contraction in endothelial cells (van Nieuw Amerongen et al., 2000). FIG. 17A shows time- and concentration-dependent activation of RhoA by thrombin treatment in hBMVECs, where 0.1 unit of thrombin increased maximum activity of RhoA at 5 min after treatment. FIG. 17B shows time lapse (i) and cumulative value (ii) of $[Ca^{2+}]_i$ influx where thrombin increased $[Ca^{2+}]_i$ influx in a concentration dependent manner in hBMVECs. Along with the inductions of $[Ca^{2+}]_i$ influx and RhoA activation, thrombin also induced cellular levels of phospho-MLC ($Ser^{19}$) in time- and concentration-dependent manners (FIG. 17C). Accordingly, thrombin treatment induced the formation of robust long F-actin filaments (phalloidin staining), which contained higher amount of phospho-MLC, so called stress fibers (FIG. 17D-i) and decreased transendothelial electrical resistance (TEER) indicating endothelial barrier disruption (FIG. 17D-ii).

Thrombin Activated eNOS Causes Increased Protein Nitration (3-Nitrotyrosine) but not Protein-Associated S-Nitrosothiols in hBMVECs.

Figures 18A, 18B, 18C:
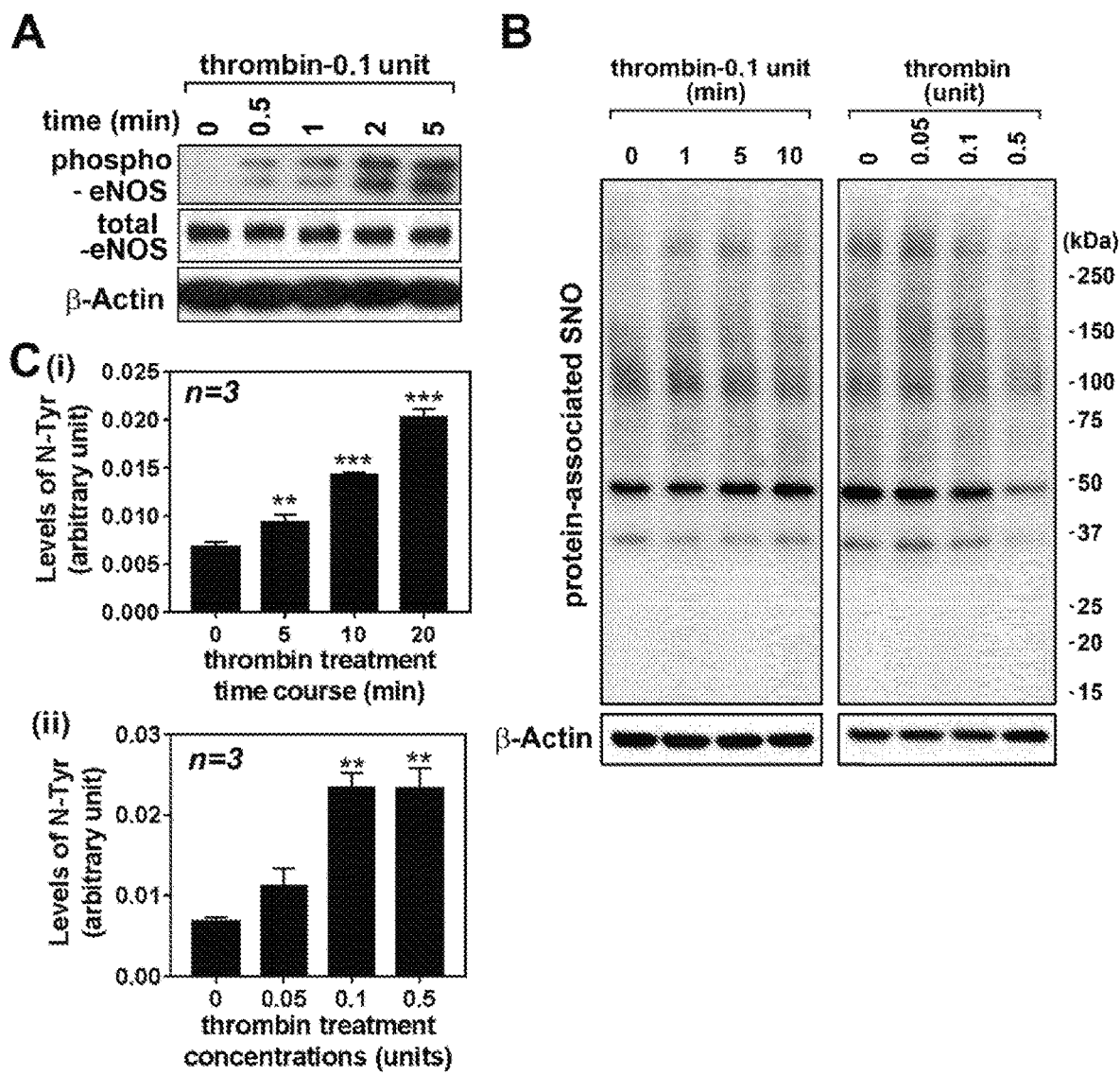
FIGS. 18A-18C: Effect of thrombin on endothelial eNOS activity and NO metabolism in hBMVECs. (A) Human brain microvessel endothelial cells (hBMVECs) were treated with thrombin (0.1 unit/ml) and time course activation of eNOS was analyzed by Western analysis using antibody specific to phospho (Ser1177) eNOS. β-actin was used for internal loading control. hBMVEC were treated with thrombin and time and concentration dependent accumulation of protein-associated S-nitrosothiols (B) or protein-associated 3-nitrotyrosine (N-Tyr) (C) or were analyzed by biotin switch assay or ELISA, respectively. The vertical columns represent means of individual data set and T-bars are standard error mean.  $p \leq 0.01$ and * $p \leq 0.001$ as compared to the control group. All experiments were repeated at least three times and representative data are shown.

Thrombin is known to activate eNOS activity in human umbilical vein endothelial cells (Thors et al., 2004). Accordingly, thrombin treatment of hBMVECs also caused activation eNOS via increasing phosphorylation at $Ser^{1177}$ (FIG. 18A). NO is a short-lived molecule and its longer effect can be achieved by formation of secondary redox metabolites, such as GSNO and ONOO⁻, and subsequent modifications of protein thiols (S-nitrosylation) or tyrosines (tyrosine nitration) (Gaston et al., 2003; Pacher et al., 2007). FIG. 17 shows that 0.1 unit of thrombin is effective for activation of cell signaling for endothelial barrier disruption. However, the same concentration of thrombin treatment had no effect on the cellular levels of protein-associated S-nitrosothiol (Pr-SNO), which is in dynamic equilibrium with cellular levels of GSNO (Broniowska et al., 2013), while higher concentrations of thrombin (0.5 unit) slightly reduced cellular levels of Pr-SNO (FIG. 18B). On the other hand, thrombin treatment resulted in increased cellular levels of protein-associated 3-nitrotyrosine (FIG. 18C) formed by nitration of protein tyrosine residues by ONOO⁻. Therefore, these data indicate that thrombin induces eNOS activation for de novo synthesis of ONOO⁻ instead of GSNO.

Thrombin-Induced eNOS Activation for ONOO⁻ Production is Involved in Endothelial Barrier Disruption in hBMVECs.

Figures 19A, 19B, 19C, 19D, 19E:
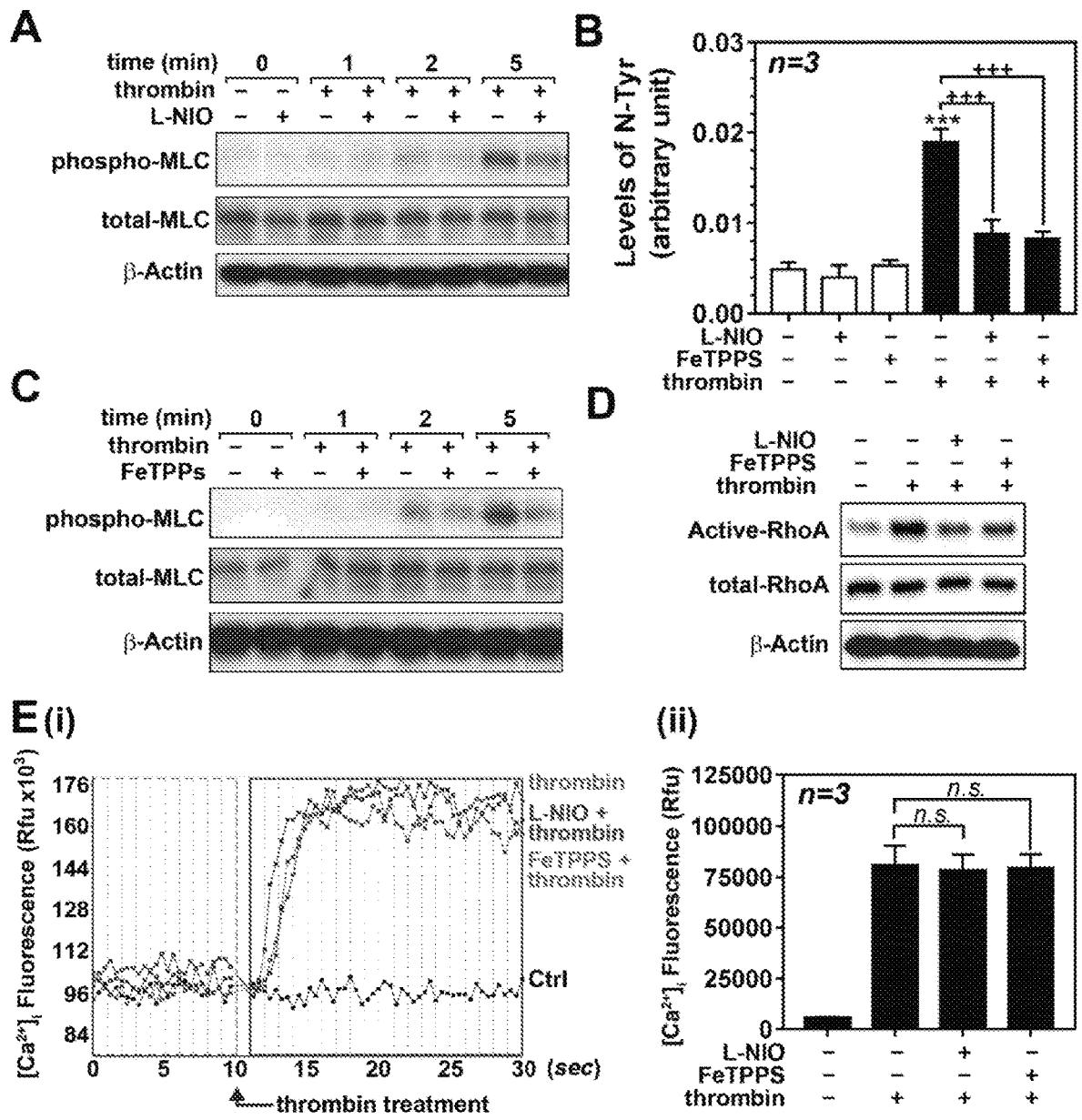
FIGS. 19A-19E: Effects of eNOS inhibitor and peroxynitrite scavenger on thrombin-induced cell signaling for endothelial barrier disruption in hBMVECs. (A) Human brain microvessel endothelial cells (hBMVECs) in the presence or absence of NOS inhibitor L-NIO (10 μM; pretreated for 30 min) were treated with thrombin (0.1 unit/ml for 5 min) and MLC phosphorylation (Ser19) was analyzed by Western analysis with β-actin as internal loading control. B. hBMVECs were treated with thrombin (0.1 unit/ml for 20 min) in the presence or absence of L-NIO (10 μM; pretreated for 30 min) or ONOO⁻ scavenger FeTTPS (10 μM; pretreated for 30 min) and cellular levels of protein-associated 3-nitrotyrosine (a protein adduct formed by ONOO⁻) was analyzed by ELISA. hBMVECs were treated with thrombin (0.1 unit/ml for 5 min) in the presence or absence of FeTPPS or L-NIO and MLC phosphorylation (C), RhoA activity (D), and intracellular $Ca^{2+}$ ($[Ca^{2+}]_i$) influx (E) were analyzed. The vertical bars are means of individual data and T-bars are standard error mean. *** $p \leq 0.001$ as compared to the control group. +++ $p \leq 0.001$ as compared to thrombin treated group. All experiments were repeated at least three times and representative data are shown.

Next, the role of thrombin-induced eNOS activation and ONOO⁻ production in cell signaling pathways for MLC phosphorylation was investigated. FIG. 19A shows that inhibition of thrombin-induced eNOS activation by NOS inhibitor L-NIO (10 μM) inhibited thrombin-induced induction of MLC phosphorylation. In addition, L-NIO treatment also attenuated thrombin-induced production of 3-nitrotyrosine (FIG. 19B). Next, the role of ONOO⁻ in thrombin-induced phosphorylation of MLC by treatment of the cells with ONOO⁻ scavenger FeTPPS (10 µM) was assessed. As shown in FIGS. 19B and C, FeTTPS treatment inhibited thrombin-induced increases in 3-nitrotyrosine levels (ONOO⁻) and MLC phosphorylation, indicating the role of eNOS-mediated ONOO⁻ production in thrombin-induced MLC phosphorylation. Next, the effects of L-NIO and FeTPPS on thrombin-induced RhoA activation and $[Ca^{2+}]_i$, influx were examined. FIG. 19D shows that treatment of hBMVECs with either L-NIO or FeTPPS decreased thrombin-induced RhoA activation. However, L-NIO and FeTTPs treatment had not effect on thrombin-induced intracellular $Ca^{2+}$ influx, a critical step for activation of eNOS (Fleming and Busse, 1999). These data indicate that thrombin-induced $Ca^{2+}$ influx is an upstream event to eNOS activation and ONOO⁻ synthesis, RhoA activation, and subsequent MLC phosphorylation.

Opposing Roles of GSNO Vs. ONOO⁻ in Thrombin-Induced Cell Signaling for Endothelial Barrier Disruption in hBMVECs.

Figures 20A, 20B, 20C, 20D:
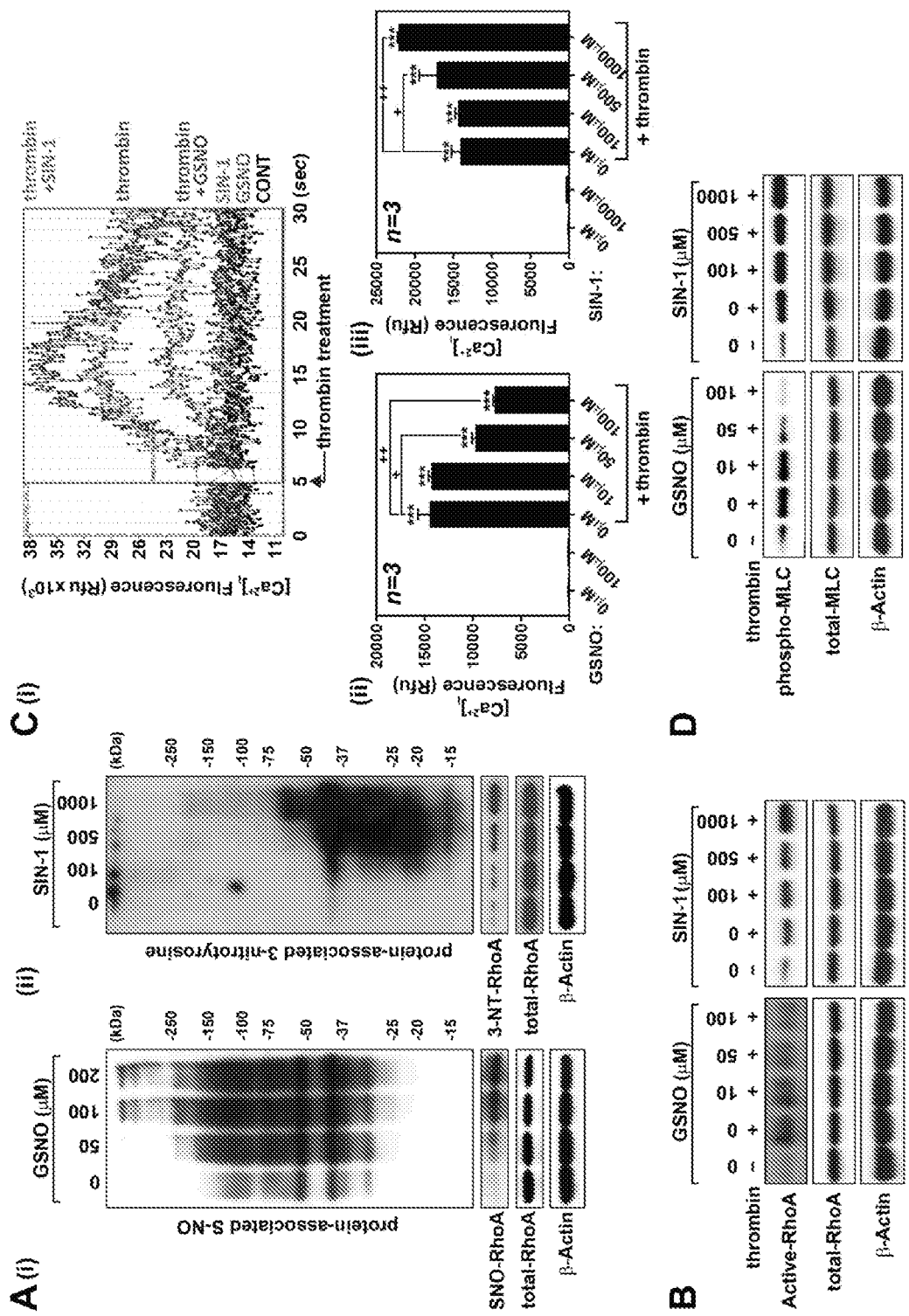
FIGS. 20A-20D: Opposing roles of GSNO vs. ONOO⁻ in thrombin-induced cell signaling for endothelial barrier disruption in hBMVECs. Human brain microvessel endothelial cells (hBMVECs) were treated with various concentrations of GSNO or SIN-1 (ONOO⁻ donor), incubated for 2 hr, and cellular levels of S-nitrosylated proteins and RhoA (A-i) and tyrosine-nitrated proteins and RhoA (A-ii) were analyzed as described in method section. hBMVECs were treated with thrombin (0.1 unit/ml for 5 min), in the presence or absence of various concentrations GSNO or SIN-1 (pretreated for 2 hr), and RhoA activity was analyzed as described in method section (B). hBMVECs were treated with thrombin (0.1 unit/ml) in the presence or absence of various concentrations GSNO or SIN-1 and intracellular $Ca^{2+}$ ($[Ca^{2+}]_i$) influx was analyzed (C). hBMVECs were treated with thrombin (0.1 unit/ml for 5 min), in the presence or absence of various concentrations GSNO or SIN-1, and MLC phsophorylation was analyzed by Western analysis (D). β-actin was used for internal loading control for Western analysis. The vertical bars are means of individual data and T-bars are standard error mean. *** $p \leq 0.001$ as compared to the control group. + $p \leq 0.05$ and ++ $p \leq 0.01$ as compared to thrombin treated group. All experiments were repeated at least three times.

Next the role of GSNO vs. ONOO⁻ treatments on thrombin-induced cell signaling for endothelial barrier disruption was assessed. FIG. 20A shows that GSNO treatment of hBMVECs increased the cellular levels of protein-associated S-nitrosothiols, while SIN-1 (a donor of ONOO⁻) treatment increased the cellular levels of protein-associated 3-nitrotyrosine. In addition, GSNO also increased RhoA S-nitrosylation while SIN-1 increased RhoA tyrosine nitration. RhoA activity is reported to be regulated by S-nitrosylation (inhibition) and 3-nitrotyrosinylation (increase) in an opposing manner (Chen et al., 2017; Di Lorenzo et al., 2013; Rafikov et al., 2014). Accordingly, GSNO treatment inhibited the thrombin-induced RhoA activation (FIG. 20B-i) while SIN-1 treatment enhanced the thrombin-induced RhoA activation (FIG. 20B-ii). Interestingly, thrombin-induced $[Ca^{2+}]_i$ influx in hBMVECs was also inhibited by GSNO treatment while it enhanced by SIN-1 treatment (FIG. 20C). Accordingly, thrombin-induced MLC phosphorylation was attenuated by GSNO treatment but enhanced by SIN-1 treatment (FIG. 20D).

Figures 21A, 21B, 21C:
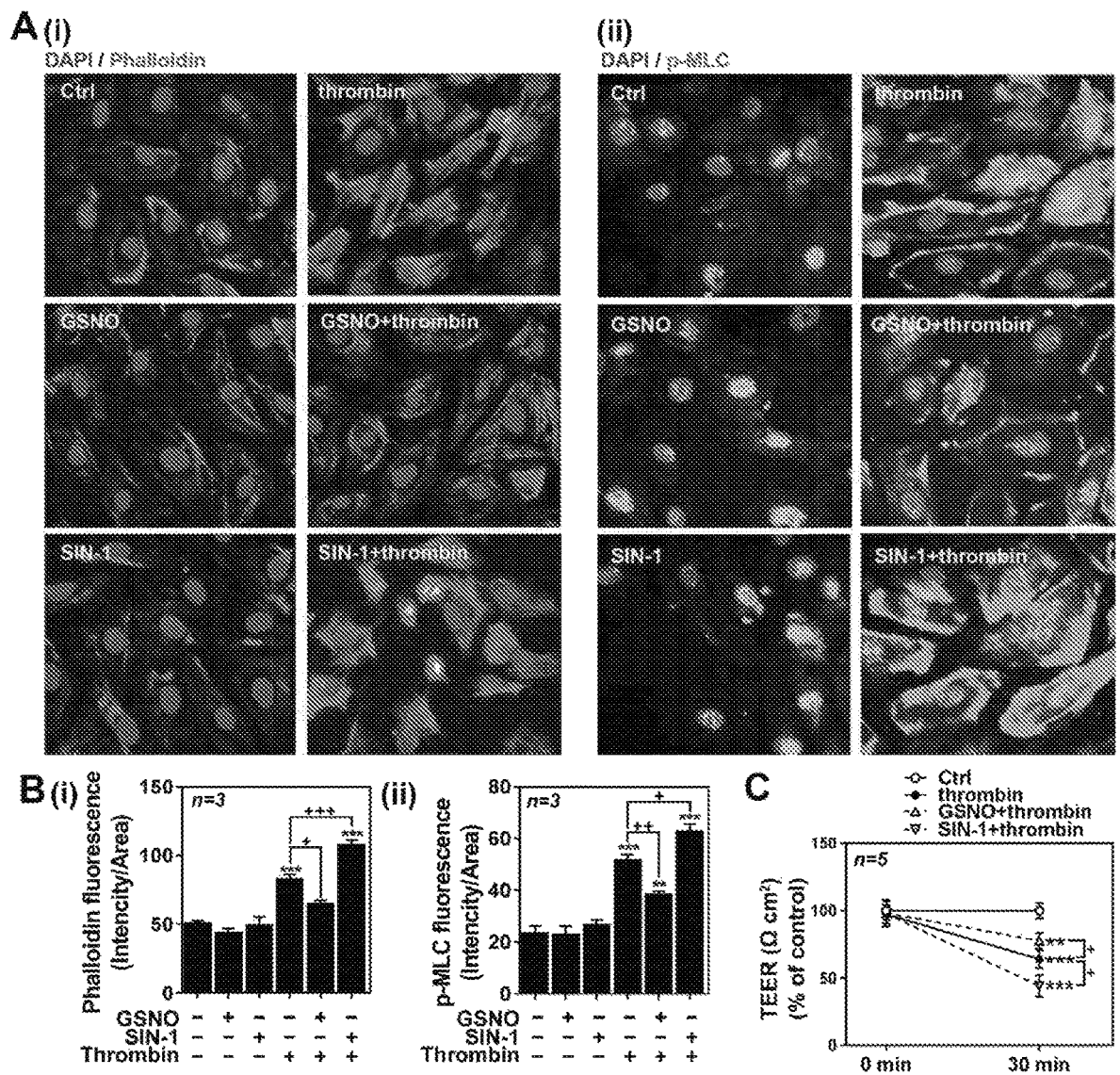
FIGS. 21A-21C: Opposing roles of GSNO vs. ONOO⁻ in thrombin-induced cell signaling for endothelial barrier disruption in hBMVECs. (A) Human brain microvessel endothelial cells (hBMVECs) were treated with thrombin (0.1 unit/ml for 30 min) in the presence or absence of GSNO (100 μM; pretreated for 2 hr) or SIN-1 (100 μM; pretreated for 2 hr) and development of F-actin stress fiber was analyzed by immunofluorescent staining of F-actin bundles by Phalloidin (red-i) and phosphorylated MLC (p-MLC; green-ii). Nuclei were stained by DAPI (blue). (B) The resulting digital images were used for quantification of fluorescence and the data is represented by RFU (relative flurescence unit). (C) hBMVECs were cultured on transwell plates and transendothelial electric resistance (TEER) was analyzed. The cells were treated with thrombin (0.1 unit/ml for 5 min) in the absence or presence of GSNO (100 μM; pretreated for 2 hr) or SIN-1 (500 μM; pretreated for 2 hr). The vertical bars and dotted lines are means of individual data and T-bars are standard error mean.  $p \leq 0.01$ and * $p \leq 0.001$ as compared to the control group. $^+$ $p \leq 0.05$, $^{++}$ $p \leq 0.01$, and $^{+++}$ $p \leq 0.001$ as compared to thrombin treated group. All experiments were repeated at least three times.

Next, the effect of GSNO vs. SIN-1 (ONOO⁻) on thrombin-induced F-actin stress fiber formation and endothelial barrier disruption was investigated. FIGS. 21A and B describe that GSNO treatment inhibited thrombin-induced development of F-actin stress fiber formation (phalloidin staining and MLC-phosphorylation) as well as thrombin-induced loss of TEER (FIG. 21C). On the other hand, SIN-1 (ONOO⁻) treatment enhanced the thrombin-induced development of F-actin stress fiber formation and loss of TEER. Taken together, these data document regulation of endothelial barrier by different redox-dependent NO metabolites (GSNO vs. ONOO⁻) in an opposing signaling mechanisms.

Roles of GSNO Vs. ONOO⁻ in Regulation of Endothelial Barrier Function in TBI Model.

TBI commonly involves blood vessel injuries producing various forms of hemorrhage (Chodobski et al., 2011). Thrombin controls the loss of blood at the sites of TBI (Xi et al., 2003), but it also induces vascular inflammation and endothelial barrier disruption, leading to BBB leakage, edema formation, and neuronal and tissue damages (Popovic et al., 2012). Based on the observed opposing effects of GSNO vs. ONOO⁻ in thrombin-induced endothelial barrier disruption, the roles of GSNO vs. ONOO⁻ in regulation of vascular pathology leading to edema in rat model of TBI were investigated.

Figure 22A:
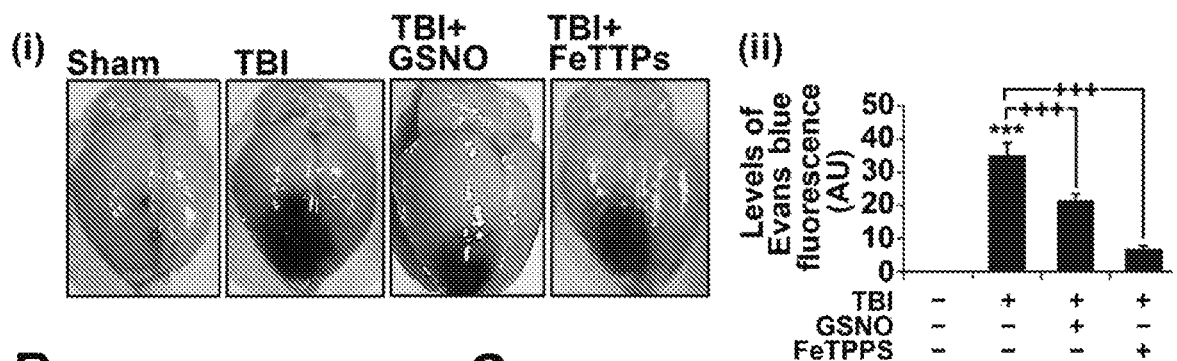
FIGS. 22A-22C: Roles of GSNO and FeTPPS on BBB leakage, edema and the expression of 3-NT in TBI rat model. (A) Photographs showing Evan's blue (EB) extravasations in brain starting at 4 hr after TBI. Animals were sacrificed at 24 hr, the brain was photographed (i) and the intensity of EB (ii) was determined by spectrofluorometric estimation. EB extravasations were not observed in sham brain. (B) Edema (tissue water content) was measured at 24 hr after TBI. (C) The levels of nitrotyrosine (N-Tyr) as an index of ONOO$^-$ was also measured at 24 hr in the traumatic penumbra region using Western and its quantitation by densitometry. Data are expressed as mean±SD from five different experiments for Evan's blue and edema each and three different experiments for western blot. * $p \leq 0.05$, *** $p \leq 0.001$ vs. Sham and $^+$ $p \leq 0.05$, $^{++}$ $p \leq 0.01$, and $^{+++}$ $p \leq 0.001$ vs. TBI.
Figure 22B:
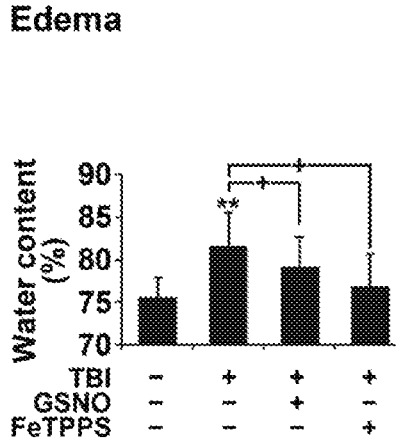
Figure 22C:
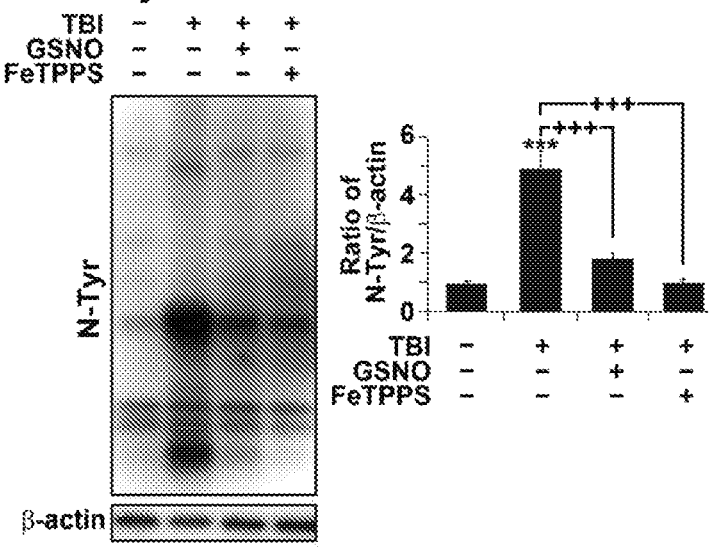

TBI was induced by controlled cortical impact in adult male rats. GSNO (0.05 mg/kg/i.v./day) or FeTPPS (ONOO⁻ scavenger; 3 mg/kg/i.v./day) was administered at right after the impact. Next day, BBB leakage and degree of edema were assessed by Evan's blue extravasation and brain water content. FIGS. 22A and 22B show that TBI-induced increases in Evan's blue extravasation and degree of brain water content were reduced with GSNO as well as FeTTPS treatment, indicating the opposing roles of different redox dependent NO metabolites (GSNO vs. ONOO⁻) in post-traumatic BBB leakage and edema formation. It is of interest to note that GSNO treatment, in addition to FeTTPs treatment, reduced the brain levels of 3-nitrotyrosine in rat brains with TBI (FIG. 22C), indicating that GSNO-mediated mechanisms also protect cerebrovascular nitrosative stress under TBI conditions.

Figures 23A, 23B, 23C, 23D, 23E:
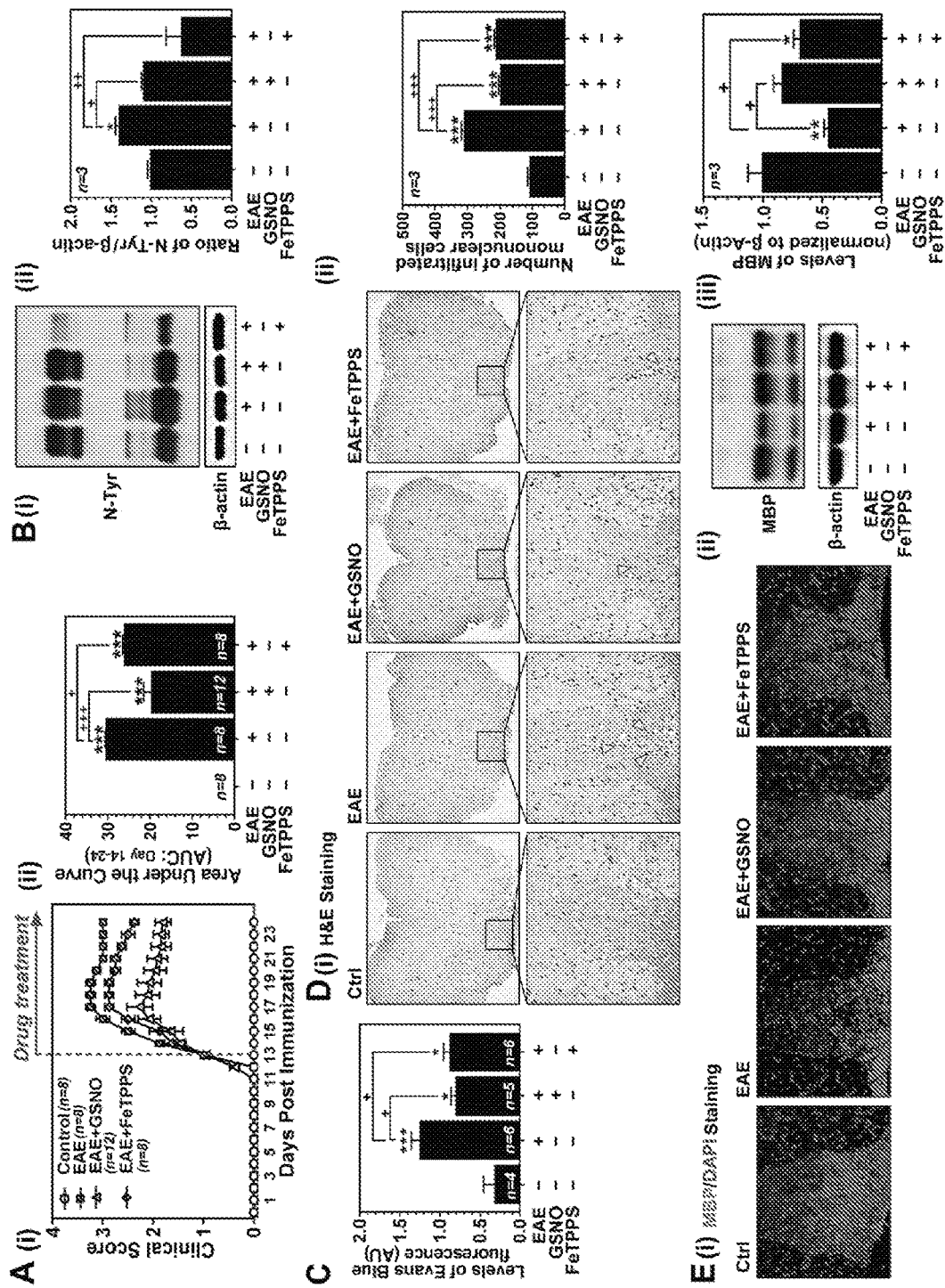
FIGS. 23A-23E: Roles of GSNO and FeTPPS on clinical disease, expression of 3-nitrotyrosine, BBB leakage, and spinal cord demyelination in mouse EAE model. (A) Clinical score of control C57BL/6 mice (Ctrl: n=8), C57BL/6 mice immunized with MOG35-55 peptide (EAE: n=8), EAE mice treated with 1 mg/kg/day of GSNO (EAE+GSNO: n=12) or 30 mg/kg/day of FeTPPS (EAE+FeTPPS: n=8) was determined daily as described in Materials and Methods (i). All drugs were administered starting at the day of disease onset (day 13 post-immunization) via intraperitoneal routes. The area under the curve (AUC) between post immunization day 14 and 24 of the overall disease severity was calculated and represented as bar graph (ii). (B) At 24 day post-immunization, the mice (n=4) were sacrificed and the levels of 3-nitrotyrosine (N-Tyr), as an index of ONOO$^-$, were measured by Western (i) and densitometry analysis (ii). (C) In addition, another set of mice (n=4) were injected with Evans blue for analysis of BBB leakage. (D) Spinal cord infiltration of mononuclear cells was analyzed by H&E staining of paraffin-embedded spinal cord section (i). The number of mononuclear cells (dark-brown nuclei aggregates indicated by yellow triangles) was counted manually and represented by bar graph (ii). (E) The spinal cord sections and tissue lysates were also subjected to immunofluoresence staining (i) and Western analysis for MBP (ii and iii) for degree of demyelination. Data are expressed as mean±standard error mean (SEM). * $p \leq 0.05$,  $p \leq 0.01$, * $p \leq 0.001$ vs. control and $^+$ $p \leq 0.05$, $^{++}$ $p \leq 0.01$, and $^{+++}$ $p \leq 0.001$ vs. EAE.

Roles of GSNO Vs. ONOO⁻ in Regulation of Endothelial Barrier Function in EAE Model:

MS is induced by peripheral activation of myelin specific autoreactive lymphocytes and their CNS infiltration across the BBB leading to encephalitogenic inflammatory disease (Compston and Coles, 2002). There is growing evidence that thrombin activation participates in the disease process of MS (Brass, 2003; Langer et al., 2012; Shapiro, 1991). In addition, BBB disruption has been regarded as one of the key consequences of the thrombin activation in MS and EAE (Davalos et al., 2014; Stolz et al., 2017). To investigate the role of GSNO vs ONOO⁻ in endothelial barrier disruption, EAE mice were treated with daily dose of GSNO (1 mg/kg/i.p./day) or FeTPPS (30 mg/kg/i.p./day) at the onset of disease with clinical score between 1 and 2 (day 13 post immunization) (FIG. 23A). Similar to our previous study (Nath et al., 2010), GSNO treatment provided great efficacy against clinical disease of EAE (FIGS. 23A-i and -ii). FeTTPS treatment also provided significant efficacy but to a lower degree than GSNO treatment (FIGS. 23A-i and -ii).

Next, degree of tissue levels of ONOO⁻ (protein nitrotyrosine levels in FIG. 23B), BBB leakage (Evan's blue extravasation assay in FIG. 23C), peripheral mononulcear cell infiltration (H&E staining in FIGS. 23D-i and ii), and spinal cord demyelination (myelin basic protein/MBP staining in FIG. 23E-i and Western analysis in FIGS. 23E-ii and iii) were analyzed. Consistent with effects on clinical disease, GSNO and FeTPPS treatments also significantly decreased the EAE-induced nitrotyrosine levels in spinal cords as well as extravasation of Evan's blue dye and peripheral mononuclear cells into the CNS. Accordingly, both treatments also protected myelin in the spinal cord from EAE disease.

Taken together, in vitro cell culture studies and in vivo studies with animal models of TBI and EAE document that redox-dependent metabolites of eNOS produced NO (GSNO vs. ONOO⁻) pity critical roles in cell signaling pathways for endothelial barrier integrity (e.g. RhoA/ROCK, intracellular $Ca^{2+}$ influx, and MLC phosphorylation) and thus BBB disruption under traumatic and inflammatory neurological disease conditions.

BBB disruption, a characteristic feature of numerous neurological disease conditions (Neuwelt et al., 2011), causes brain edema as well as greater influx of blood-borne cells and substances into brain parenchyma, thus exacerbating neuroinflammation and brain injuries (Nishikawa and Suzuki, 2017). Although the precise mechanism underlying BBB disruption is poorly understood at present, (1) $Ca^{2+}$ influx and RhoA/ROCK mediated induction of MLC phosphorylation for F-actin stress fiber formation, (2) and followed endothelial cell contraction and disassembly of tight junctional complex, (3) and further disruption of weakened endothelial barrier by matrix metalloproteases (MMPs) have been proposed as key sequential processes (Shi et al., 2016). Recent studies report that early BBB permeability may be partially reversible (Kaur et al., 2009; Neumann-Haefelin et al., 2000; Olah et al., 2000), thus making early events of BBB permeability (e.g. F-actin stress fiber formation and junctional protein redistribution) as a rational target for therapeutic interventions (Kaur et al., 2009). Here, it is reported that early events of BBB permeability, especially endothelial F-actin stress fiber formation, is regulated by eNOS-derived NO metabolites (ONOO$^-$ and GSNO) in opposing manners, thus highlighting the potential therapeutic importance of redox dependent NO metabolism for BBB protection. These conclusions are supported by in vitro mechanistic studies and studies with animal models of TBI and MS.

In this study, thrombin-treated hBMVECs were used as an in vitro disease model for early event in BBB disruption. Thrombin plays an essential role in blood coagulation and it is also known to induce non-hemostatic cell signaling involved in BBB disruption and subsequent edema formation and neuroinflammation (Bogatcheva et al., 2002; Xi et al., 2003). Recently, thrombin has been implicated in various neurological disease conditions, such as TBI, MS, Alzheimer's disease, Parkinson's disease, and stroke (Cannon et al., 2007; Chen et al., 2010; Chodobski et al., 2011; Davalos et al., 2014; Grammas and Martinez, 2014). Thrombin induces non-hemostatic cell signaling pathways via activation of PAR$_1$ and subsequent induction of intracellular Ca$^{2+}$ influx and activation of RhoA/ROCK (van Nieuw Amerongen et al., 2000). As a result, the activated MLC kinase and inactivated MLC phosphatase increase phosphorylation of MLC and induce actomyosin stress fiber formation (van Nieuw Amerongen et al., 2000) and thus alteration in endothelial cell shape, adhesion, and intercellular permeability (Bogatcheva et al., 2002). Accordingly, it was observed that thrombin-induced RhoA activity, intracellular Ca$^{2+}$ influx, and MLC phosphorylation, and consequently, endothelial F-actin stress fiber formation and loss of endothelial barrier in hBMVEC culture (FIG. 17). Thrombin treatment also induced eNOS activity and resulted in increased de novo synthesis of ONOO$^-$, as observed by increased cellular levels of protein-associated 3-nitrotyrosine (FIGS. 18A and B). Thrombin is also reported to induce O$_2^-$ production by activation of NADPH oxidase (Holland et al., 1998). Therefore, these observations indicate that thrombin-induced activation of NADPH oxidase for O$_2^-$ synthesis shifts the metabolism of NO, produced by eNOS, towards ONOO$^-$ synthesis. On the other hand, thrombin treatment had no effect on cellular synthesis of GSNO, as observed by unaltered/decreased cellular levels of protein-associated S-nitrosothiols (FIG. 18C). These data suggest that thrombin activity hampers GSNO de novo synthesis by inducing ONOO$^-$ synthesis in hBMVECs.

Previous studies reported that tyrosine nitration of RhoA$^-$ (Tyr34) enhances RhoA activity and accelerates endothelial barrier disruption (Rafikov et al., 2014). On the other hand, S-nitrosylation of RhoA (Cys16, 20, and 159) is reported to inhibit its activity in endothelial cells (Chen et al., 2017). Accordingly, using hBMVECs, it was observed that exogenous GSNO treatment increased the S-nitrosylation of RhoA and inhibited its thrombin induced activation (FIGS. 20A and B). In addition, treatment of hBMVECs with SIN-1 (ONOO$^-$ donor) increased the tyrosine nitration of RhoA and enhanced its thrombin induced activation (FIGS. 20A and B). Thrombin-induced intracellular Ca$^{2+}$ influx was not affected by eNOS inhibition by L-NIO or ONOO$^-$ scavenging by FeTTPS (FIG. 19E). However, thrombin-induced intracellular Ca$^{2+}$ influx was enhanced by SIN-1 (ONOO$^-$ donor) pretreatment while inhibited by GSNO pretreatment (FIG. 20C). At present, mechanisms underlying ONOO$^-$ or GSNO dependent regulation of intracellular Ca$^{2+}$ influx are not well understood but similar observations were made with smooth muscle cells in another study (Pan et al., 2004). In smooth muscle cells, ONOO$^-$ was reported to induce intracellular Ca$^{2+}$ influx via acting on L-type voltage-gated calcium channels (Pan et al., 2004) while GSNO was reported to inhibit intracellular Ca$^{2+}$ influx via inhibiting inositol-1,4,5-trisphosphate (IP$_3$) (Nalli et al., 2014). In addition to RhoA activity and intracellular Ca$^{2+}$ influx, thrombin-induced MLC phosphorylation (FIG. 20D) and endothelial F-actin stress fiber formation and barrier disruption (FIG. 21) were also increased by SIN-1 treatment while inhibited by GSNO treatment. These data describe importance of redox mediated balance of NO metabolism (ONOO$^-$ vs. GSNO) in thrombin-mediated non-hemostatic cell signaling pathways for brain endothelial barrier disruption under the pathological conditions.

The brain edema, especially vasogenic edema caused by BBB disruption, is a significant challenge facing clinicians managing TBI during the acute period of diseases. If edema reaches a critical point, it leads to severe morbidity or death if left untreated. Currently, therapies being in use for management of post-traumatic edema formation include osmotherapy, diuretics, corticosteroids, barbiturates, propofol, and/or hyperventilation. However, endothelial mechanism underlying the vasogenic brain edema is still elusive and thus no specific mechanism-based-therapy is currently available. Our laboratory has reported the efficacy of GSNO treatment during the acute disease of stroke and TBI to attenuate brain endothelial barrier disruption, abnormal BBB permeability, edema formation, and vascular inflammation in rat models (Khan et al., 2012; Khan et al., 2009). Later, it was also reported that GSNO treatment attenuates neurodegeneration and accelerates neovascularization and neurorepair and thus improved functional outcome in TBI animals (Khan et al., 2016a; Khan et al., 2016b; Khan et al., 2011). This study has demonstrated the opposing roles of redox-dependent NO metabolites (ONOO$^-$ vs. GSNO) in regulation of RhoA activation and intracellular Ca$^{2+}$ influx and thus MLC phosphorylation leading to endothelial stress fiber formation and barrier disruption in hBMVECs. Accordingly, it was observed that treatment of TBI animals with GSNO or ONOO$^-$ scavenger (FeTPPs), which shifts the endothelial balance of NO metabolites (GSNO vs. ONOO$^-$) toward GSNO, ameliorated TBI-induced BBB leakage and edema formation (FIG. 22).

In MS, CNS infiltration of myelin specific autoreactive lymphocytes across the disrupted BBB is the critical pathological events leading to inflammatory demyelination (Compston and Coles, 2002). Brain imaging studies have shown that patients with relapsing-remitting MS (RRMS), the most common type of MS (>80%), have generally increase in BBB permeability (Cramer et al., 2014; Stone et al., 1995). It is of interest to note that MS patients and EAE animals also have increased thrombin activity (Brass, 2003; Langer et al., 2012; Shapiro, 1991), which participates in BBB disruption during the course of the disease (Davalos et al., 2014; Stolz et al., 2017). In this study, it was observed that treatment of EAE animals with GSNO or ONOO$^-$ scavenger (FeTPPs) ameliorated EAE-induced BBB leakage and CNS infiltration of mononuclear cells (FIG. 23), documenting the role of GSNO vs. ONOO⁻ in BBB permeability during the course of EAE disease.

In summary, the present study demonstrates the role of redox-based NO metabolites (ONOO⁻ vs. GSNO) in endothelial barrier disruption leading to vasogenic edema formation and peripheral immune cell infiltration under traumatic and inflammatory neurological disease conditions. ONOO⁻ accelerates endothelial barrier disruption via enhancing cell signaling (e.g. RhoA activation and intracellular $Ca^{2+}$ influx) for MLC phosphorylation and endothelial stress fiber formation whereas GSNO inhibits endothelial barrier disruption via inhibiting these cell signaling mechanisms. This study documents that ONOO⁻ and GSNO levels mechanistically antagonize each other in endothelial barrier disruption. Thrombin induces endothelial barrier disruption via inducing eNOS activity for ONOO⁻ synthesis. Therefore, modulation of redox dependent endothelial NO metabolism (decreasing ONOO⁻ synthesis and increasing GSNO synthesis) is critical for protection of endothelial barrier in brain pathologies of traumatic and inflammatory brain injuries. Thrombin-mediated endothelial barrier disruption has been also implicated in various neurological disorders, such as Alzheimer's disease, Parkinson's disease, and stroke (Cannon et al., 2007; Chen et al., 2010; Grammas and Martinez, 2014). Therefore, regulation of redox-dependent NO metabolism (ONOO⁻ vs. GSNO) is also relevant as therapeutic target for other neurological disorders.

The present study shows that thrombin-induced endothelial eNOS activation for NO synthesis and synthesis of ONOO⁻ enhances thrombin-induced intracellular $Ca^{2+}$ influx, RhoA activation, and thus MLC phosphorylation for endothelial stress fiber formation associated with endothelial barrier disruption. On the other hand, exogenous GSNO inhibits thrombin-induced cell signalings for MLC phosphorylation and endothelial stress fiber formation thus barrier disruption. These observations underscore an importance of redox-dependent NO metabolism (ONOO⁻ vs. GSNO) in cell signalings for endothelial barrier integrity. Accordingly, this study also shows that BBB disruption in animal model of TBI and EAE are inhibited by ONOO⁻ scavenger (FeTPPS) or GSNO treatment and thus identifying redox-dependent NO metabolites (ONOO⁻ vs. GSNO) as a potential therapeutic targets for neurovascular integrity in neurological disorders.

Example 8—Materials and Methods

Reagents:

Thrombin was purchase from Sigma-Aldrich (Cat #: T4393, St. Louis, Mo.). L-NIO [$N^5$-(1-Iminoethyl)-L-omithine dihydrochloride] and SIN-1 (3-morpholinosydnonimine chloride) were purchase from Tocris (Cat #: 0546 and 0756, respectively, Minnellis, Minn.). FeTPPS [5,10,15,20-Tetrakis(4-sulfonatophenyl)porphyrinato Iron (III), Cl] was purchase from Millipore-Calbiochem (Cat #: 341492, Billerica, Mass.). S-nitrosoglutathione (GSNO) was purchase from World precision instruments (Cat #: GSNO-100, Sarasota, Fla.). The effective concentration of the GSNO was calculated from the optical absorbance at 338 nm and the reported molar extinction coefficients as described previously (Gordge et al., 1998).

Cell culture: Primary human brain microvascular endothelial cells (hBMVECs) were purchased from Angio-Proteomie (Cat #: cAP-0002, Atlanta, Ga.). The cells were cultured in cell culture flasks or plates precoated with Quick Coating Solution (Angio-Proteomie; Cat #: cAP-01) and maintained in Endothelial Growth Medium (Angio-Proteomie; Cat #: cAP-02) at 37° C. under 5% $CO_2$/95% air. When the cells were almost confluent, the medium was replaced with endothelial basal medium (Angio-Proteomie; Cat #: cAP-03) containing 0.5% fetal bovine serum (FBS; Life Technologies, Grand Island, N.Y.) about 8-12 hours before the experiment. No institutional approval was required for this study. The study was not pre-registered.

Assay of Trans-Endothelial Electrical Resistance (TEER):

For evaluation of the endothelial barrier function, hBMVECs were plated on fibronectin-coated polycarbonate filters (Transwell system, Corning, Midland, N.C.) containing Endothelial Growth Medium (Angio-Proteomie Cat #: cAP-02). The medium was renewed every other day. Five days after seeding, the medium was replaced with Endothelial Basal Medium (Angio-Proteomie Cat #: cAP-03) containing 0.5% FBS and incubated for 2 days. Following drug treatments, transendothelial electrical resistance (TEER) was measured by EVOM2 (Word Precision Instruments) as described previously (Li et al., 2006).

RhoA Activity Assay:

RhoA activity in hBMVECs was analyzed by RhoA Activation Assay Kit (Abeam Cat #: ab211164, Cambridge, Mass.). Briefly, following drug treatments, the cells were lysed with 1× Assay buffer provided in the kit. Lysates were centrifuged (14,000×g for 10 sec), and supernatants were incubated with agarose beads coupled to GST-Rhotekin-Rho binding domain (RBD) for 2 h at 4° C. Beads were then washed with 1× Assay buffer and GTP-bound RhoA was eluted with 2×SDS-PAGE sample buffer. Amounts of active (GTP-bound) RhoA were determined by Western blot analysis using antibody specific to RhoA (Abeam).

Assay for F-actin stress fiber development and endothelial cell contraction: hBMVECs were cultured on fibronectin-coated chamber slides (BD Bioscience). Following drug treatments, the cells were fixed with 4% (wt/vol) paraformaldehyde, permeabilized by the addition of 0.25% Triton X-100, and blocked by 2% bovine serum albumin (BSA) in phosphate buffered saline (PBS). The slides were immunostained for phospho-MLC ($Ser^{19}$) as well as stained with Phalloidin for F-actin (F-actin Visualization Biochem kit, Cytoskeleton, Inc, Cat #: BK005, Denver, Colo.) and DAPI for nucleus (4',6-diamidino-2-phenylindole; ThermoFisher Scientific, Houston, Tex.). The cells were imaged by BX60 Olympus fluorescent/light microscope equipped with DP-70 digital camera (Olympus, Tokyo, Japan). The density of fluorescence was analyzed by ImageJ (NIH, Bethesda, Md.).

Assay for Intracellular $Ca^{2+}$ Influx:

Intracellular $Ca^{2+}$ concentration ($[Ca^{2+}]_i$) was measured with Fluo-4 Direct Calcium Assay Kit (Thermo Fisher Scientific, Cat #: F10471, Grand Island, N.Y.). Briefly, culture medium in the 96-well plate was replaced with a $Ca^{2+}$ sensitive dye Fluo-4 in an endothelial basal medium. After 30 min incubation, the dye was removed and cells were incubated with the original medium with or without the drugs at 37° C. for 15 min. Following thrombin treatment, time course changes of fluorescent intensity were quantified using a CLARIOstar multi-well fluorometer (BMG Labtech, Cary, N.C.).

Western Blot Analysis:

Western immunoblot analysis was performed by standard method using 50 μg of cell lysates. Following the SDS-PAGE electrophoresis, proteins were transferred from the gel onto the Polyvinylidene fluoride membrane (GE Healthcare Life Sciences, Marlborough, Mass.). Membranes were blocked with non-fat dry milk (Santa Cruz Biotechnology)

or I-Block™ (ThermoFisher Scientific, Waltham, Mass.) for detection of phospho-proteins and incubated with primary antibodies, such as MBP (Santa Cruz Biotech Cat #: sc13914; RRID: AB_648798), phospho-(Ser$^{19}$) MLC (Abcam, Cat #: ab2480; RRID: AB_303094), MLC (Abcam, Cat #: ab79935; RRID:AB_1952220), β-actin (Santa Cruz Biotechnology, Cat #: sc-47778; RRID:AB_2714189), phospho-eNOS (Ser$^{1177}$) (Cell Signaling, Cat #: 9571; RRID: AB_329837, Danvers, Mass.), eNOS (Cell Signaling, Cat #: 32027), RhoA (Santa Cruz Biotechnology; Cat #: sc418; RRID: AB_628218) or 3-nitrotyrosine (Abcam, Cat #: ab61392; RRID: AB_942087). Following washing, the membranes were incubated with horseradish peroxidase conjugated secondary antibody (Jackson Immunoresearch Lab, West Grove, Pa.), washed and then incubated with ECL reagent (Amersham Life Science, Pittsbrugh, Pa.), and exposed to Amersham Hyperfilm ECL film Assay for Protein-Associated Nitrotyrosine:

Cellular levels of protein-associated 3-nitrotyrosine were analyzed by ELISA Kit (Abcam, Cat #: ab116691) and Western blot analysis using antibody specific to 3-nitrotyrosine (Abcam, Cat #: ab61392). For the ELISA, hBMVECs were lysed in extraction buffer provided with the kit followed by centrifugation at 16,000×g 4° C. The cell lysate supernatants were subjected to protein quantification with Bio-Rad DC protein assay kit (Bio-Rad, Hercules, Calif.) and the equal amounts of proteins (500 μg) were loaded onto 96 well microplate coated with 3-nitrotyrosine capture antibody and followed by incubation with biotin-conjugated 3-nitrotyrosine detector antibody. Following washing, the plates were incubated with HRP-conjugated streptoavidin and the levels of 3-nitrotyrosine were measured by incubation with 3,3',5,5'-tetramethylbenzidine solution and colorimetric analysis at 600 nm using SpectraMax 190 Microplate Reader (Molecular Devices, Sunnyvale, Calif.). For analysis of degree of RhoA tyrosine nitration, the cell lysates were immunoprecipitated with antibody specific to 3-nitrotyrosine (Abcam) and the levels of tyrosine nitrated RhoA were analyzed by Western analysis for RhoA.

Assay for protein-associated S-nitrosylation: Protein S-Nitrosylation was analyzed by using biotin-switch method as described in our previous reports (Kim et al., 2014; Prasad et al., 2007). hBMVECs were lysed in 250 mM HEPES, pH 7.7, 1 mM EDTA, 0.1 mM neocuproine, 1% Nonidet P-40, 150 mM NaCl, 1 mM phenylmethanesulfonylfluoride, 20 mM methyl methanethiosulfonate (MMTS), 80 μM carmustine, protease inhibitor mixture (Sigma-Aldrich), and mixed with an equal volume of 25 mM HEPES, pH 7.7, 0.1 mM EDTA, 10 μM neocuproine, 5% SDS, 20 mM MMTS and incubated at 50° C. for 20 min. Following acetone precipitation, the precipitates were resuspended in 25 mM HEPES, pH 7.7, 0.1 mM EDTA, 10 μM neocuproine, 1% SDS and mixed with two volumes of 20 mM HEPES, pH 7.7, 1 mM EDTA, 100 mM NaCl, 0.5% Triton X-100. The S-nitrosylated proteins were then modified with biotin in 25 mM HEPES, pH 7.7, 0.1 mM EDTA, 1% SDS, 10 μM neocuproine, 10 mM ascorbate sodium salt, and 0.2 mM N-[6-(biotinamido)hexyl]-30-(20-pyridyldithio) propionamide (biotin-HPDP, Pierce). Following acetone precipitation, biotinylated (S-nitrosylated) proteins were analyzed by Western analysis. For detection of S-nitrosylated RhoA, the biotinylated proteins were pull down with neutravidin-agarose and followed by Western analysis for RhoA.

Controlled Cortical Impact (CCI) Rat Model of Focal TBI:

All animals used in this study received humane care in compliance with the Medical University of South Carolina's (MUSC) guidance and the National Research Council's criteria for humane care. Animal procedures were approved by the institutional animal care and use committee of MUSC (AR #2703). For generation of CCI model of TBI, young adult male (~3-4 months old) Sprague Dawley rats weighing between 260-300 g were randomly divided into four groups: 1) TBI animals treated with vehicle (TBI; n=13), 2) TBI with GSNO (0.05 mg/kg body weight/i.v.) treatment (TBI+GSNO; n=13), 3) TBI with FeTPPS (3 mg/kg body weight, i.v.) treatment (TBI+FeTPPS; n=13), 4) sham-operated treated with vehicle (Sham; n=13). The group size was determined by power analysis based on our previous data (Khan et al., 2016b; Khan et al., 2009). Ketamine (90 mg/kg body weight) and xylazine (10 mg/kg body weight) as surgical anesthesia were administered intraperitoneally. Analgesic buprenorphine was administered pre-emptively to alleviate pain following surgery. Utilizing aseptic techniques, CCI injury was produced as previously described from our laboratory (Khan et al., 2016b; Khan et al., 2009) and others (Kline et al., 2008; Kline et al., 2007). A cortical contusion was produced on the exposed cortex using a controlled impactor device as described in our previous TBI studies (Khan et al., 2016b; Khan et al., 2009). Immediately after injury, the skin incision was closed with nylon sutures. Lidocaine jelly (2%) was applied to the lesion site to minimize any possible infection/discomfort. Sham animals had no cortical impact but underwent the same procedure otherwise.

Evaluation of BBB Disruption by Evans Blue (EB) Extravasation:

BBB leakage was assessed as previously described from our laboratory (Khan et al., 2016b; Khan et al., 2009). The rats received 100 μl of a 5% solution of EB in saline administered intravenously 4 hours following CCI. At 24 hours, cardiac perfusion was performed under deep anesthesia with 200 ml of saline to clear the cerebral circulation of EB. The brain was removed, photographed, and sliced. The brain tissues were homogenized in 750 μl of N, N-dimethylformamide (DMF) and centrifuged at 10,000×g for 25 minutes, and EB content in supernatant was fluorimetrically analyzed ($\lambda_{ex}$ 620 nm, $\lambda_{em}$ 680 nm).

Measurement of Edema (Brain Water Content):

At 24 h following CCI, animals were euthanized to determine brain water content (edema) as described earlier (Hoda et al., 2009; Khan et al., 2009). The cortices, excluding the cerebellum, were quickly removed, and the contralateral and ipsilateral hemispheres separately weighed. Each hemisphere was dried at 60° C. for 72 hours, and the dry weight was determined. Water content was calculated in ipsilateral hemisphere as: water content (%)=(wet weight−dry weight)/wet weight×100.

EAE Induction:

EAE was induced as described previously (Nath et al., 2009). Animal procedures were approved by the institutional animal care and use committee of MUSC (AR #1644). Briefly, female C57BL/6J mice of 8-12 weeks of age weighing 18-22 g (The Jackson Laboratory, Bar Harbor, Me., USA) were randomly divided into four groups: 1) EAE animals treated with vehicle (EAE; n=8), 2) EAE with GSNO (1 mg/kg body weight per day; i.p.) treatment (EAE+GSNO; n=12), 3) EAE with FeTPPS (30 mg/kg body weight per day; i.p.) treatment (EAE+FeTPPS; n=8), 4) control with vehicle (Ctrl; n=8). The group size was determined by power analysis based on our previous data (Nadi et al., 2009). Then, the mice were immunized subcutaneously in the flank regions with MOG$_{35-55}$ peptide (MOG; 200 ug; Peptide International) emulsified (1:1) in 100 ul complete Freund's adjuvant (CFA) CHI day 0 and day 7. Additionally, 200 ng of Pertussis toxin (PTX; Sigma-Aldrich, St Louis, Mo.) was given on dry 0 and dry 2 by i.p. injection. PTX used as per the standardized protocol reported by us and other investigators for the induction of EAE (Nath et al., 2009). Similarly, control group received subcutaneous injection of CFA emulsion and PTX. Clinical signs of EAE were scored in animal facility in a blinded fashion to experimenter between 2 and 4 pm daily by examiners blinded to experimental treatments using the following scale: 0=no clinical signs of disease; 1=limp tail or waddling gait with tail tonicity; 2=waddling gait with limp tail (ataxia); 2.5=ataxia with partial limb paralysis; 3=full paralysis of one limb; 3.5=full paralysis of one limb with partial paralysis of second limb; 4=full paralysis of two limbs; 4.5=moribund stage; 5=death. Starting the day of disease onset (with clinical score between 1 and 2), the animals were given daily treatment with drugs and vehicle (phosphate buffered saline).

Histological and Immuno-Histological Analysis:

Animals were anesthetized and fixed with cardiac perfusion of 4% paraformaldehyde (Nath et al., 2004). Tissue samples (lumbar spinal cords) were paraffin-embedded and sectioned transversely (4-µm-thick). Haemotoxylin and Eosin (H&E) staining was performed to assess infiltration of mononuclear cells. To assess the status of myelin, the sections were stained with antibody specific to MBP and detected with secondary antibody conjugated with immunofluorescent analysis. DAPI (4',6-Diamidino-2-Phenylindole, Dihydrochloride) was used for staining of nuclei. All digital images were taken using BX-60 microscope equipped with DP70 camera unit (Olympus, Tokyo, Japan).

Statistical analysis: Statistical analysis was performed with Graph pad Prism5. Values are expressed as mean±standard error mean (SEM). Comparisons among means of groups were made with a two-tailed Student's t-test for unpaired variables. Multiple comparisons were performed using one-way ANOVA followed by Bonferroni test. A value of $p<0.05$ was considered statistically significant.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abbott et al., Structure and function of the blood-brain barrier. Neurobiol Dis, 37, 13-25, 2010.
Aggarwal et al., S-nitrosoglutathione prevents blood-brain barrier disruption associated with increased matrix metalloproteinase-9 activity in experimental diabetes. J Neurochem, 132, 595-608, 2015.
Altannavch et al., Effect of high glucose concentrations on expression of ELAM-1, VCAM-1 and ICAM-1 in HUVEC with and without cytokine activation. Physiol Res, 53, 77-82, 2004.
Bauer et al., The dual role of zonula occludens (ZO) proteins. J Biomed Biotechnol, 2010, 402593, 2010.
Bettelli et al., IL-10 is critical in the regulation of autoimmune encephalomyelitis as demonstrated by studies of IL-10- and IL-4-deficient and transgenic mice, J Immunol 161, 3299-3306, 1998.
Cho et al., 2008.
Citi, et al., Cingulin, paracingulin, and PLEKHA7: signaling and cytoskeletal adaptors at the apical junctional complex. Ann NY Acad Sci, 1257, 125-132, 2012.
Corti et al., Mechanisms and targets of the modulatory action of S-nitrosoglutathione (GSNO) on inflammatory cytokines expression, Arch Biochem Biophys 562, 80-91, 2014.
Dandona et al., Cerebral blood flow in diabetes mellitus: evidence of abnormal cerebrovascular reactivity. Br Med J, 2, 325-326, 1978.
del Zoppo and Mabuchi, Cerebral microvessel responses to focal ischemia. J Cereb Blood Flow Metab, 23, 879-894 2003.
Ding, et al., Diabetes increases expression of ICAM after a brief period of cerebral ischemia. J Neuroimmunol, 161, 61-67, 2005.
Ennis and Keep, Effect of sustained-mild and transient-severe hyperglycemia on ischemia-induced blood-brain barrier opening. J Cereb Blood Flow Metab, 27, 1573-1582, 2007.
Fanning and Anderson, Zonula occludens-1 and -2 are cytosolic scaffolds that regulate the assembly of cellular junctions. Ann N Y Acod Sci, 1165, 113-120, 2009.
Fiorentino et al., IL-10 acts on the antigen-presenting cell to inhibit cytokine production by Th1 cells, J Immunol 146, 3444-3451, 1991.
Furuse et al., Occludin: a novel integral membrane protein localizing at tight junctions. J Cell Biol, 123, 1777-1788, 1993.
Gao et al., In vivo molecular and cellular imaging with quantum dots. Curr Opin Biotechnol, 16, 63-72, 2005.
Giebel et al., Matrix metalloproteinases in early diabetic retinopathy and their role in alteration of the blood-retinal barrier. Lab Invest, 85, 597-607, 2005.
Greenwood et al., Lymphocyte migration into the central nervous system: implication of ICAM-1 signalling at the bloodbrain barrier. Vascul Pharmacol, 38, 315-322, 2002.
Hammes et al., Pericytes and the pathogenesis of diabetic retinopathy. Diabetes, 51, 3107-3112, 2002.
Harhaj and Antonetti, Regulation of tight junctions and loss of barrier function in pathophysiology, Int J Biochem Cell Biol, 36, 1206-1237, 2004.
Hawkins et al., Increased blood-brain barrier permeability and altered tight junctions in experimental diabetes in the rat: contribution of hyperglycaemia and matrix metalloproteinases. Diabetologia, 50, 202-211, 2007.
He and Frost, Direct measurement of actual levels of nitric oxide (NO) in cell culture conditions using soluble NO donors. Redox Bio.; 9:1-14. doi: 10.101 6/j.redox.2016.05.002. PubMed PMID: 27236086; PubMed Central PMCID: PMCPMC4899081, 2016.

Huber et al., Th17 cells express interleukin-10 receptor and are controlled by Foxp3(−) and Foxp3+ regulatory CD4+ T cells in an interleukin-10-dependent manner, Immunity 34, 554-565, 2011.

Joussen et al., Retinal vascular endothelial growth factor induces intercellular adhesion molecule-1 and endothelial nitric oxide synthase expression and initiates early diabetic retinal leukocyte adhesion in vivo. Am J Pathol, 160, 501-509, 2002.

Khan et al., Administration of S-nitrosoglutathione after traumatic brain injury protects the neurovascular unit and reduces secondary injury in a rat model of controlled cortical impact. J Neuroinflammation, 6, 32, 2009.

Khan et al., S-Nitrosoglutathione reduces inflammation and protects brain against focal cerebral ischemia in a rat model of experimental stroke. J Cereb Blood Flow Metab, 25, 177-192 2005.

Khan et al., S-nitrosoglutathione reduces oxidative injury and promotes mechanisms of neurorepair following traumatic brain injury in rats. J Neuroinflammation, 8, 78, 2011.

Kim J, Won J S, Singh A K, Sharma A K, Singh I. STAT3 regulation by S-nitrosylation: implication for inflammatory disease. Antioxid Redox Signal, 20(16):2514-27. doi: 10.1089/ars.2013.5223. Pub Med PMID: 24063605; PubMed Central PMCID: PMCPMC4026100, 2014.

Langrish et al., 2005.

Mogi and Horiuchi, Neurovascular coupling in cognitive impairment associated with diabetes mellitus. Circ J, 75, 1042-1048, 2011.

Morita et al., Expression of claudin-5 in dermal vascular endothelia. Exp Dermatol, 12, 289-295, 2003.

Nath et al., S-nitrosoglutathione a physiologic nitric oxide carrier attenuates experimental autoimmune encephalomyelitis, J Neuroimmune Pharmacol 5 (2010) 240-251, 2010.

Nath N, Giri S, Prasad R, Singh A K, Singh I. Potential targets of 3-hydroxy-3-methylglutaryl coenzyme A reductase inhibitor for multiple sclerosis therapy. J Immunol. 172(2): 1273-86. Epub 2004 Jan. 7. PubMed PMID: 14707106, 2004.

Nath N, Khan M, Paintlia M K, Singh I, Hoda M N, Giri S. Metformin attenuated the autoimmune disease of the central nervous system in animal models of multiple sclerosis. J Immunol. 182(12):8005-14. Epub 2009 Jun. 6. doi: 10.4049/jimmunol.0803563. PubMed PMID: 19494326; PubMed Central PMCID: PMC2965405, 2009.

Nath N, Morinaga O, Singh I. S-nitrosoglutathione a physiologic nitric oxide carrier attenuates experimental autoimmune encephalomyelitis. J Neuroimmune Pharmacol, 5(2):240-51. doi: 10.1007/s11481-009-9187-x. PubMed PMID: 20091246; PubMed Central PMCID: PMCPMC2965418, 2010.

Niedbala et al., Nitric oxide induces CD4+CD25+ Foxp3 regulatory T cells from CD4+CD25 T cells via p53, IL-2, and OX40. Proc Natl Acad Sci USA. 2007; 104(39): 15478-83. doi: 10.1073/pnas.0703725104. PubMed PMID: 17875988; PubMed Central PMCID: PMCPMC1978217, 2007.

Niedbala et al., 2007.

Nitta et al., Size-selective loosening of the blood-brain barrier in claudin-5-deficient mice. J Cell Biol, 161, 653-660, 2003.

Ohtsuki et al., Exogenous expression of claudin-5 induces barrier properties in cultured rat brain capillary endothelial cells. J Cell Physiol, 210, 81-86, 2007.

Pfaffl et al., Relative expression software tool (REST) for group-wise comparison and statistical analysis of relative expression results in real-time PCR. Nucleic Acids Res, 30, e36, 2002.

Phillips et al., Oxidant stress and constrictor reactivity impair cerebral artery dilation in obese Zucker rats. Am J Physiol Regul Integr Comp Physiol, 288, R522-530, 2005.

Prasad et al., GSNO attenuates EAE disease by Snitrosylation-mediated modulation of endothelial-monocyte interactions, Glia 55, 65-77, 2007.

Rauhala et al., Neuroprotective properties of nitric oxide and Snitrosoglutathione. Toxicol Appl Pharmacol, 207, 91-95, 2005.

Song and Qian, IL-17 family cytokines mediated signaling in the pathogenesis of inflammatory diseases, Cell Signal 25, 2335-2347, 2013.

Starr et al., Increased blood-brain barrier permeability in type II diabetes demonstrated by gadolinium magnetic resonance imaging. J Neural Neurosurg Psychiatry, 74, 70-76, 2003.

Veena et al., Enriched environment restores hippocampal cell proliferation and ameliorates cognitive deficits in chronically stressed rats. J Neurosci Res, 87, 831-843, 2009.

Won et al., Protective role of S-nitrosoglutathione (GSNO) against cognitive impairment in rat model of chronic cerebral hypoperfusion, J Alzheimers Dis 34, 621-635, 2013.

Yang et al., J Immunol., 185(11): 6664-9, 2010.

Zampolli et al., Inhibition of endothelial cell activation by nitric oxide donors. J Pharmacol Exp Ther, 295, 818-823, 2000.

Zlokovic, B. V., The blood-brain barrier in health and chronic neurodegenerative disorders.

Neuron, 57, 178-201, 2008.

Bogatcheva et al., Biochemistry, 67:75-84, 2002.

Brass, Chest, 124:18S-25S, 2003.

Cannon et al., Behav Brain Res., 183: 161-8, 2007.

Chen et al., Stroke. 41: 2348-52, 2010.

Chen et al., Biochem Pharmacol., 127: 34-45, 2017.

Chodobski et al., Transl Stroke Res., 2: 492-516, 2011.

Compston and Coles, Lancet, 359: 1221-31, 2002.

Cramer et al., Neuroimage Clin., 4: 182-9, 2014.

Davalos et al., Ann Neurol. 75: 303-8, 2014.

Di Lorenzo et al., J Cell Sci., 126: 5541-52, 2013.

Gaston et al., Mol Interv., 3: 253-63, 2003.

Gordge et al., Br J Pharmacol., 124: 141-8, 1998.

Grammas and Martinez, J Alzheimers Dis., 42 Suppl 4: S537-44, 2014.

Holland et al., Endothelium, 6: 113-21, 1998.

Kaur et al., Int J Stroke, 4: 159-68, 2009.

Khan et al., Behav Brain Res., 2016a.

Khan et al., Brain Res., 1630: 159-70, 2016b.

Khan et al., J Neurochem, 123 Suppl 2: 86-97, 2012.

Khan et al., J Neuroinflammation., 6: 32, 2009.

Khan et al., J Neuroinflammation, 8: 78, 2011.

Kim et al., Antioxid Redox Signal, 20: 2514-27, 2014.

Kline et al., Neurosci Lett., 448: 263-7, 2008.

Kline et al., Behav Brain Res., 177: 186-94, 2007.

Langer et al., Circ Res., 110: 1202-10, 2012.

Li et al., FEBS Lett., 580: 4252-60, 2006.

Nath et al., J Immunol., 172: 1273-86, 2004.

Nath et al., J Immunol., 182: 8005-14, 2009.

Nath et al., J Neuroimmune Pharmacol., 5: 240-51, 2010.

Neumann-Haefelin et al., Stroke, 31: 1965-72; discussion 1972-3, 2000.

Neuwelt et al., Nat Rev Neurosci., 12: 169-82, 2011.
Nishikawa and Suzuki, Neural Regen Res., 12: 1982-1984, 2017.
Olah et al., J Cereb Blood Flow Metab., 20: 1474-82, 2000.
Pacher et al., Physiol Rev., 87: 315-424, 2007.
Pan et al., Redox Rep., 9: 49-55, 2004.
Popovic et al., Mol Cell Biochem., 359: 301-13, 2012.
Prasad et al., Glia, 55: 65-77, 2007.
Rafikov et al., J Biol Chem., 289: 4710-22, 2014.
Shapiro, J Am Acad Dermatol., 24: 665, 1991.
Stolz et al., J Neuroinflammation, 14: 152, 2017.
Stone et al., Neurology, 45: 1122-6, 1995.
Thors et al., FEES Lett., 573: 175-80, 2004.
van Nieuw Amerongen et al., Circ Res., 87: 335-40, 2000.
Won et al., J Alzheimers Dis., 34: 621-35, 2013.
Xi et al., J Neurochem., 8: 3-9, 2003.

What is claimed is:

1. A method of treating a neurological deficit in a subject comprising administering an effective amount of a GSNO reductase inhibitor to the subject.

2. The method of claim 1, wherein the GSNO reductase inhibitor is N6022.

3. The method of claim 1, wherein treating the neurological deficit comprises restoring blood brain barrier (BBB) integrity, decreasing neurological inflammation, decreasing brain edema, improving ultrastructure of microvessels, and/or improving cognition.

4. The method of claim 3, wherein restoring BBB integrity is further defined as increasing expression of a tight junction protein and/or decreasing expression of a cell adhesion molecule.

5. The method of claim 3, wherein the BBB disruption is a stroke.

6. The method of claim 4, wherein the increase or decrease in expression is at least 2-fold as compared to expression before administering the GSNO reductase inhibitor.

7. The method of claim 6, wherein the expression is measured in the cortex and/or hippocampus.

8. The method of claim 1, wherein the subject has diabetes.

9. The method of claim 8, wherein the subject has hyperglycemia associated with diabetes.

10. The method of claim 1, wherein the subject has an autoimmune disease.

11. The method of claim 10, wherein the autoimmune disease is multiple sclerosis (MS).

12. The method of claim 1, wherein the GSNO reductase inhibitor is administered orally, intravenously, intraperitoneally, intratracheally, intratumorally, intramuscularly, endoscopically, intralesionally, percutaneously, subcutaneously, regionally, or by direct injection or perfusion.

13. The method of claim 1, wherein the GSNO reductase inhibitor is administered orally.

14. A method of treating an autoimmune disease in a subject comprising administering an effective amount of a GSNO reductase inhibitor to the subject and at least a second therapy.

15. The method of claim 14, wherein the autoimmune disease is multiple sclerosis, rheumatoid arthritis, systemic lupus erythematosis, type 1 diabetes mellitus, Crohn's disease, psoriasis, eczema, or dermatitis.

16. The method of claim 14, wherein the second therapy is an anti-inflammatory, immunosuppressive agent, or immunomodulatory agent.

17. The method of claim 14, wherein the second therapy is interferon-β, glatiramer acetate, teriflunomide, dimethyl fumarate, natalizumab, fingolimod, alemtuzumab, mitoxantrone, and/or simvastatin.

18. The method of claim 5, wherein the subject is suffering from a stroke.

19. The method of claim 10, wherein the autoimmune disease is rheumatoid arthritis.

20. The method of claim 3, wherein the BBB disruption is cerebral ischemia.

21. The method of claim 3, wherein the BBB disruption is a traumatic brain injury, or spinal cord injury.

22. The method of claim 3, wherein the BBB disruption is a spinal cord injury.

* * * * *

UNITED STATES PATENT AND TRADEMARK OFFICE
CERTIFICATE OF CORRECTION

| | | |
|---|---|---|
| PATENT NO. | : 10,925,858 B2 | Page 1 of 1 |
| APPLICATION NO. | : 16/336984 | |
| DATED | : February 23, 2021 | |
| INVENTOR(S) | : Inderjit Singh and Avtar K. Singh | |

It is certified that error appears in the above-identified patent and that said Letters Patent is hereby corrected as shown below:

In the Specification

Column 1, Lines 11-15, delete the entire contents and replace with --The invention was made with government support under Grant No. NS72511 awarded by the National Institutes of Health and Grant Nos. BX002829, RX001257 and RX2090 awarded by the U.S. Department of Veterans Affairs. The government has certain rights in the invention.-- therefor.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial sequence
<220> FEATURE:
<223> OTHER INFORMATION: Synthetic primer

<400> SEQUENCE: 1
ccgcaggtcc aattcacact                                              20

<210> SEQ ID NO 2
<211> LENGTH: 19
<212> TYPE: DNA
<213> ORGANISM: Artificial sequence
<220> FEATURE:
<223> OTHER INFORMATION: Synthetic primer

<400> SEQUENCE: 2
cagagcggca gagcaaaag                                               19

<210> SEQ ID NO 3
<211> LENGTH: 22
<212> TYPE: DNA
<213> ORGANISM: Artificial sequence
<220> FEATURE:
<223> OTHER INFORMATION: Synthetic primer

<400> SEQUENCE: 3
gggaagctgg aacgaagtat cc                                           22

<210> SEQ ID NO 4
<211> LENGTH: 23
<212> TYPE: DNA
<213> ORGANISM: Artificial sequence
<220> FEATURE:
<223> OTHER INFORMATION: Synthetic primer

<400> SEQUENCE: 4
tctggagcca aacacttgac tgt                                          23

<210> SEQ ID NO 5
<211> LENGTH: 25
<212> TYPE: DNA
<213> ORGANISM: Artificial sequence
<220> FEATURE:
<223> OTHER INFORMATION: Synthetic primer

<400> SEQUENCE: 5
aagccagcct ctcaacagaa agcag                                        25

<210> SEQ ID NO 6
<211> LENGTH: 20
<212> TYPE: DNA
<213> ORGANISM: Artificial sequence
<220> FEATURE:
```

```
<223> OTHER INFORMATION: Synthetic primer

<400> SEQUENCE: 6
aggctgtgat gcgtgcgagc                                              20

<210> SEQ ID NO 7
<211> LENGTH: 20
<212> TYPE: DNA
<213> ORGANISM: Artificial sequence
<220> FEATURE:
<223> OTHER INFORMATION: Synthetic primer

<400> SEQUENCE: 7
gctgtgatgt gtgttgagct                                              20

<210> SEQ ID NO 8
<211> LENGTH: 20
<212> TYPE: DNA
<213> ORGANISM: Artificial sequence
<220> FEATURE:
<223> OTHER INFORMATION: Synthetic primer

<400> SEQUENCE: 8
gacggtctac ctggaggaac                                              20

<210> SEQ ID NO 9
<211> LENGTH: 20
<212> TYPE: DNA
<213> ORGANISM: Artificial sequence
<220> FEATURE:
<223> OTHER INFORMATION: Synthetic primer

<400> SEQUENCE: 9
ctggaccaca acatcgtgac                                              20

<210> SEQ ID NO 10
<211> LENGTH: 20
<212> TYPE: DNA
<213> ORGANISM: Artificial sequence
<220> FEATURE:
<223> OTHER INFORMATION: Synthetic primer

<400> SEQUENCE: 10
gccggtcaag gtaacaaaga                                              20

<210> SEQ ID NO 11
<211> LENGTH: 20
<212> TYPE: DNA
<213> ORGANISM: Artificial sequence
<220> FEATURE:
<223> OTHER INFORMATION: Synthetic primer

<400> SEQUENCE: 11
atgacatcaa gaaggtggtg                                              20

<210> SEQ ID NO 12
<211> LENGTH: 19
<212> TYPE: DNA
<213> ORGANISM: Artificial sequence
<220> FEATURE:
<223> OTHER INFORMATION: Synthetic primer

<400> SEQUENCE: 12
cataccagga aatgagctg                                               19
```